US008147800B2

(12) United States Patent
McBride et al.

(10) Patent No.: US 8,147,800 B2
(45) Date of Patent: *Apr. 3, 2012

(54) METHODS AND COMPOSITIONS FOR F-18 LABELING OF PROTEINS, PEPTIDES AND OTHER MOLECULES

(75) Inventors: William J. McBride, Boonton, NJ (US); Christopher A. D'Souza, Pomona, NY (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/163,145

(22) Filed: Jun. 17, 2011

(65) Prior Publication Data

US 2011/0280801 A1 Nov. 17, 2011

Related U.S. Application Data

(60) Division of application No. 12/343,655, filed on Dec. 24, 2008, now Pat. No. 7,993,626, which is a continuation-in-part of application No. 12/112,289, filed on Apr. 30, 2008, now Pat. No. 7,563,433, which is a continuation-in-part of application No. 11/960,262, filed on Dec. 19, 2007, now Pat. No. 7,597,876.

(60) Provisional application No. 60/884,521, filed on Jan. 11, 2007.

(51) Int. Cl.
*A61K 51/00* (2006.01)
*A61M 36/14* (2006.01)

(52) U.S. Cl. ............... 424/1.89; 424/1.65; 424/1.81; 424/1.85; 424/9.4

(58) Field of Classification Search ............... 424/1.11, 424/1.49, 1.53, 1.65, 1.69, 1.73, 1.81, 1.85, 424/1.89, 9.1, 9.3, 9.4, 9.5, 9.6, 9.7, 9.8
See application file for complete search history.

(56) References Cited

U.S. PATENT DOCUMENTS

| 5,256,395 | A | 10/1993 | Barbet et al. | |
|---|---|---|---|---|
| 5,446,147 | A | 8/1995 | Kung et al. | |
| 6,056,939 | A | 5/2000 | Desreux et al. | |
| 6,207,858 | B1 | 3/2001 | Chinn et al. | |
| 6,605,615 | B2 | 8/2003 | Medina et al. | |
| 6,838,073 | B1 | 1/2005 | Collins et al. | |
| 6,953,567 | B2 | 10/2005 | Griffiths et al. | |
| 7,011,816 | B2 | 3/2006 | Griffiths et al. | |
| 7,081,452 | B2 | 7/2006 | Brechbiel et al. | |
| 7,163,935 | B2 | 1/2007 | Brechbiel et al. | |
| 7,563,433 | B2 * | 7/2009 | McBride et al. | 424/1.89 |
| 7,597,876 | B2 * | 10/2009 | McBride et al. | 424/1.89 |
| 7,993,626 | B2 * | 8/2011 | McBride et al. | 424/1.89 |
| 2002/0006379 | A1 | 1/2002 | Hansen et al. | |
| 2003/0064523 | A1 | 4/2003 | Popov et al. | |
| 2005/0136001 | A1 | 6/2005 | McBride et al. | |
| 2006/0140858 | A1 | 6/2006 | Goldenberg et al. | |
| 2006/0228050 | A1 | 10/2006 | Chang et al. | |
| 2008/0027220 | A1 | 1/2008 | Stossel et al. | |
| 2008/0038191 | A1 | 2/2008 | Perrin et al. | |
| 2008/0089838 | A1 | 4/2008 | Hansen et al. | |
| 2008/0170989 | A1 | 7/2008 | McBride et al. | |

FOREIGN PATENT DOCUMENTS

| WO | 2007027385 | 3/2007 |
|---|---|---|
| WO | 2008088648 | 7/2008 |

OTHER PUBLICATIONS

Cai et al., "Chemistry with [18F]Fluoride Ion" Eur. J. Org. Chem. 2008, pp. 2853-2873.
Clark et al., "The Preparation of Fluorine-18 Labelled Compounds Using a Recirculatory Neon Target" Radiochem. Radioanal. Letters 14(2):101-108 (1973).
Imahori et al., "Fluorine-18-Labeled Fluoroboronophenylalanine PET in Patients with Glioma" J Nucl Med 1998; 39:325-333.
Karacay et al., "18F labeling of a peptide for PET imaging of receptor-expressing tumors" Abstract # 1567, 2009 SNM Annual Meeting Scientific Abstracts 50(Suppl. 2), p. 318P, May 2009.
Mamat et al., "Recent Applications of Click Chemistry for the Synthesis of Radiotracers for Molecular Imaging" Mini-Reviews in Organic Chemistry, 2009, vol. 6, pp. 21-34.
Marik et al., "Click for PET: rapid preparation of [18F]fluoropeptides using CuI catalyzed 1,3-dipolar cycloaddition" Tetrahedron Letters 47 (2006) 6681-6684.
McBride et al., "A new method of labeling peptides and proteins with F-18 via a metal ligand" Abstract #384, J Nucl Med. 2008; 49 (Supplement 1):97P.
McBride et al., "A new method of labeling peptides and proteins with F-18 via a metal ligand", PowerPoint Presentation, 55th SNM Annual Meeting, New Orleans, LA, Jun. 17, 2008.
McBride et al., "A New Method of Labeling Peptides with F-18 Via a Metal Ligand", Abstract #04, Cancer Biother Radiopharm Aug. 2008; 23(4): 514.
McBride et al., "A New Method of Labeling Peptides with F-18 Via a Metal Ligand" Abstract #68, 19th Winter Fluorine Conference (Jan. 11-16, 2009) Abstract Book, p. 32.

(Continued)

*Primary Examiner* — D L Jones
(74) *Attorney, Agent, or Firm* — Richard A. Nakashima

(57) ABSTRACT

The present application discloses compositions and methods of synthesis and use of F-18 labeled molecules of use, for example, in PET imaging techniques. The labeled molecules may be peptides or proteins, although other types of molecules may be labeled by the described methods. Preferably, the F-18 may be conjugated to a targeting molecule by formation of a metal complex and binding of the F-18-metal complex to a chelating moiety. Alternatively, the metal may first be conjugated to the chelating group and subsequently the F-18 bound to the metal. In other embodiments, the F-18 labeled moiety may comprise a targetable construct used in combination with a bispecific or multispecific antibody to target F-18 to a disease-associated antigen, such as a tumor-associated antigen. The F-18 labeled targetable construct peptides are stable in serum at 37° C. for a sufficient time to perform PET imaging analysis.

22 Claims, 15 Drawing Sheets

OTHER PUBLICATIONS

McBride et al., "A New Method of Labeling Peptides with F-18 Via a Metal Ligand" PowerPoint Presentation, 19th Winter Fluorine Conference, St. Pete Beach, FL, Jan. 13, 2009.

McBride et al., "A novel method of radiolabeling peptides with aluminium-fluoride-18 (AlF-18) using various NOTA derivatives" Abstract # 202, 2009 SNM Annual Meeting Scientific Abstracts 50(Suppl. 2), pp. 52P-53P, May 2009.

Miller et al., "Synthesis of 11C, 18F, 15O, and 13N Radiolabels for Positron Emission Tomography" Angew. Chem. Int. Ed. 2008, vol. 47, pp. 8998-9033.

Murata et al., "Formation of the Stable Myosin-ADP-Aluminum Fluoride and Myosin-ADP-Beryllium Fluoride Complexes and Their Analysis Using 19F NMR", J. Biol. Chem. 268(10):7093-7100 (1993).

Schirrmacher et al., "Recent Developments and Trends in 18F-Radiochemistry: Syntheses and Applications" Mini-Reveiws in Organic Chemistry, 2007, vol. 4, pp. 317-329.

Schoffelen et al., "Pretargeted immunoPET for imaging colorectal cancer in a mouse model" Abstract # 381, 2009 NM Annual Meeting Scientific Abstracts 50(Suppl. 2), pp. 100P, May 2009.

Ting et al., "Toward [18F]-Labeled Aryltrifluoroborate Radiotracers: In Vivo Positron Emission Tomography Imaging of Stable Aryltrifluoroborate Clearance in Mice" J. Am. Chem. Soc. 2008, 130, 12045-12055.

Ting et al., "Arylfruoroborates and Alkylfluorosilicates as Potential PET Imaging Agents: High-Yielding Aqueous Biomolecular 18F-Labeling" J. Am. Chem. Soc. 2005, 127, 13094-13095.

Wagner, Henry N., "Advancing a Molecular Theory of Disease", J Nulc Med 49(8):15N-34N. (2008).

Wester et al., "Fluorine-18 Labeling of Peptides and Proteins", Review, Ernst Schering Res. Found. Workshop 62:79-111 (2007).

International Patent Appl. No. PCT/US08/62108 titled "Improved Methods and Compositions for F-18 Labeling of Proteins, Peptides and Other Molecules" filed Apr. 30, 2008.

* cited by examiner

Synthesis of tetra *tert*-butyl *C*-NETA-succinyl

Detailed Synthesis of tetra *tert*-butyl *C*-NETA-succinyl

FIG. 6 Synthesis of Bis-t-butyl NOTA

IMP 449   NOTA-bn-NH-CS-D-Ala-D-Lys(HSG)-D-Tyr-D-Lys(HSG)-NH$_2$   MH$^+$ 1459

IMP 461  NOTA-D-Ala-D-Lys(HSG)-D-Tyr-D-Lys(HSG)-NH$_2$  MH$^+$ 1294

IMP 462   NOTA-D-Asp-D-Lys(HSG)-D-Tyr-D-Lys(HSG)-NH$_2$   MH$^+$ 1338

FIG. 10  IMP 468

Synthesis of tetra *tert*-butyl *L*-NETA

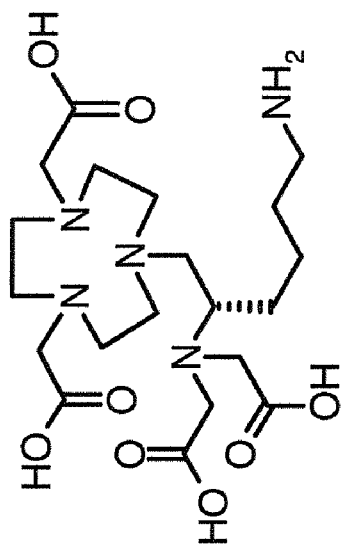
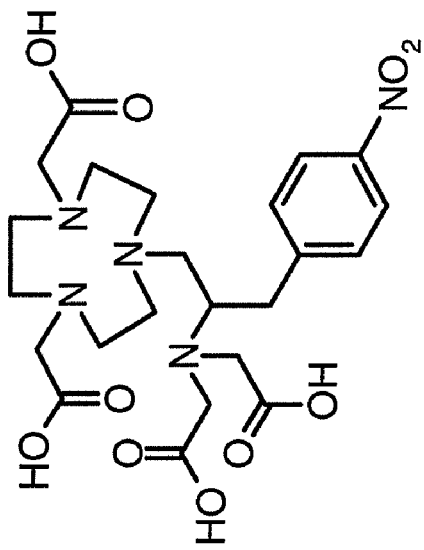
FIG. 12

IMP-465
GG23-026-8

Al-NOTA-D-Ala-D-Lys(HSG)-D-Tyr-D-Lys(HSG)-NH₂

Molecular Weight =1318.44
Exact Mass =1318
Molecular Formula =C58H86AlN18O16

US 8,147,800 B2

METHODS AND COMPOSITIONS FOR F-18 LABELING OF PROTEINS, PEPTIDES AND OTHER MOLECULES

RELATED APPLICATIONS

This application is a divisional of U.S. patent application Ser. No. 12/343,655, filed Dec. 24, 2008, now U.S. Pat. No. 7,993,626 which was a continuation-in-part of U.S. patent application Ser. No. 12/112,289 (now issued U.S. Pat. No. 7,563,433), filed Apr. 30, 2008, which was a continuation-in-part of U.S. patent application Ser. No. 11/960,262 (now issued U.S. Pat. No. 7,597,876), filed Dec. 19, 2007, which claimed the benefit under 35 U.S.C. §119(e) of Provisional U.S. Patent Application No. 60/884,521, filed Jan. 11, 20072006, each of which is incorporated herein by reference in its entirety.

FIELD

In certain embodiments, the present invention concerns a simple method of labeling peptides or other molecules with F-18, which are of use for in vivo imaging. Preferably, the F-18 is attached as a conjugate with aluminum or another metal, which may be bound to a protein, peptide or other molecule via a chelating moiety. The preferred specific activity of the F-18 labeled peptide/molecule would be about 1,000 to 2,000, more preferably 1000 to 5000 Ci/mmol at the time of administration to the patient. Specific activities that are in the range of 100 to tens of thousands of Ci/mmol would also be of use. Although higher specific activities are preferred for certain imaging applications, in other alternative embodiments a lower specific activity of a metal-F-18 complex with NOTA (1,4,7-triaza-cyclononane-N,N',N''-triacetic acid) or another chelating moiety could be of use, for example, as a renal flow imaging agent or for heart and brain imaging agents to image blood flow. Preferably, F-18 labeling is accomplished without need for a purification step to separate unlabeled from labeled peptide/molecule. More preferably, F-18 labeled peptides or other molecules are stable under in vivo conditions, such as in human serum, for at least several hours.

BACKGROUND

Positron Emission Tomography (PET) has become one of the most prominent functional imaging modalities in diagnostic medicine, with very high sensitivity (fmoles), high resolution (4-10 mm) and tissue accretion that can be adequately quantitated (Volkow et al., 1988, Am. J. Physiol. Imaging 3:142). Although [F-18]2-deoxy-2-fluoro-D-glucose ([F-18]FDG) is the most widely used functional imaging agent in oncology (Fletcher et al., 2008, J. Nucl. Med. 49:480), there is a keen interest in developing other labeled compounds for functional imaging to complement and augment anatomic imaging methods (Torigian et al., 2007, CA Cancer J. Clin. 57:206), especially with the hybrid PET/computed tomography systems currently in use. Thus, there is a need to have facile methods of conjugating positron-emitting radionuclides to various molecules of biological and medical interest.

Peptides or other small molecules can be labeled with the positron emitters $^{18}$F, $^{64}$Cu, $^{66}$Ga, $^{68}$Ga, $^{76}$Br, $^{94m}$Tc, $^{86}$Y, and $^{124}$I to name a few. The positron emitted from the nucleus of the isotope is ejected with different energies depending on the isotope used. When the positron reacts with an electron two 511 keV gamma rays are emitted in opposite directions. The energy of the ejected positron controls the average distance that a positron travels before it is annihilated by hitting an electron. The higher the ejection energy the further the positron travels before the collision with an electron. A low ejection energy for a PET isotope is desirable to minimize the distance that the positron travels from the target site before it generates the two 511 keV gamma rays that are imaged by the PET camera. Many isotopes that emit positrons also have other emissions such as gamma rays, alpha particles or beta particles in their decay chain. It is desirable to have a PET isotope that is a pure positron emitter so that any dosimetry problems will be minimized.

The half-life of the isotope is also important, since the half-life must be long enough to attach the isotope to a targeting molecule, analyze the product, inject it into the patient, and allow the product to localize, clear from non-target tissues and then image. If the half-life is too long the specific activity may not be high enough to obtain enough photons for a clear image and if it is too short the time needed for manufacturing, commercial distribution and biodistribution may not be sufficient. F-18 ($\beta^+$ 635 keV 97%, $t_{1/2}$ 110 min) is one of the most widely used PET emitting isotopes because of its low positron emission energy, lack of side emissions and suitable half-life. The F-18 is produced with a high specific activity. When an isotope is attached to a molecule for targeting it is usually accompanied by some unreacted targeting agent, which is often present in a large molar excess compared to the radiolabeled product. Usually, the labeled product and the unlabeled product can compete for the same target in vivo so the presence of the cold targeting agent lowers the effective specific activity of the targeting agent. If the F-18 is attached to a molecule which has a very high uptake such as 2-fluoro-2-deoxy glucose (FDG) then effective specific activity is not as important. However, if one is targeting a receptor with a labeled peptide or performing an immunoPET pretargeting study with a limited number of binding sites available, the cold targeting agent could potentially block the uptake of the radiolabeled targeting agent if the cold targeting agent is present in excess.

Conventional F-18 labeling of peptides involves the labeling of a reagent at low specific activity, HPLC purification of the reagent and then conjugation to the peptide of interest. The conjugate is often repurified after conjugation to obtain the desired specific activity of labeled peptide. An example is the labeling method of Poethko et al. (J. Nucl. Med. 2004; 45: 892-902) in which 4-[$^{18}$F]fluorobenzaldehyde is first synthesized and purified (Wilson et al, J. Labeled Compounds and Radiopharm. 1990; XXVIII: 1189-1199) and then conjugated to the peptide. The peptide conjugate is then purified by HPLC to remove excess peptide that was used to drive the conjugation to completion. Other examples include labeling with succinyl [F18]fluorobenzoate(SFB) (e.g., Vaidyanathan et al., 1992, Int. J. Rad. Appl. Instrum. B 19:275), other acyl compounds (Tada et al., 1989, Labeled Compd. Radiopharm.XXVII:1317; Wester et al., 1996, Nucl. Med. Biol. 23:365; Guhlke et al., 1994, Nucl. MEd. Biol 21:819), or click chemistry adducts (Li et al., 2007, Bioconjugate Chem. 18:1987). The total synthesis and formulation time for these methods ranges between 1-3 hours, with most of the time dedicated to the HPLC purification of the labeled peptides to obtain the specific activity required for in vivo targeting. The multiple reactions and purifications would not be a problem if F-18 had a long half-life. However the half-life of F-18 is only 2 hr so all of the manipulations that are needed to attach the F-18 to the peptide are a significant burden. These methods are also tedious to perform and require the use of equipment designed specifically to produce the labeled product and/or the efforts of specialized professional chemists. They are not kit formulations that could routinely be used in a clinical setting.

One alternative method for delivery of labeled adducts to tumors or other target tissues has involved a pretargeting approach (e.g., U.S. Pat. Nos. 7,052,872; 7,074,405; 7,138,103, each incorporated herein by reference). Prior studies using the bispecific antibody (bsMAb) pretargeting procedure (e.g., McBride et al., 2006, J. Nucl. Med. 10:1678-88) have focused on the use of $^{124}$I, achieving better targeting of colon cancer xenografts in animal models than directly radiolabeled fragments or $^{18}$F-FDG. While the technique has had impressive results, $^{124}$I is not a viable candidate for this imaging procedure, primarily because of its high cost (more than $2000 per dose) and relatively poor imaging properties compared to other alternatives. Other antibody-based targeting methods have had to rely on radioiodinated products for a variety of reasons, mostly because tumor/background ratios require >6 h before achieving acceptable levels. However, the pretargeting method can achieve acceptable imaging conditions within 1 h (Hamacher et al., 1986, J. Nucl. Med. 27:235; Iwata et al., 2000, Appl. Radiat. Isot. 52:87).

A need exists for a rapid, simple method of 18-F-labeling of targeting moieties, such as proteins or peptides, that results in targeting constructs of suitable specific activity and in vivo stability for detection and/or imaging, while minimizing the requirements for specialized equipment or highly trained personnel and reducing operator exposure to high levels of radiation. More preferably a need exists for methods of preparing $^{18}$F-labeled targeting peptides of use in pretargeting technologies. A further need exists for prepackaged kits that could provide compositions required for performing such novel methods.

Summary

Fluoride binds to practically all other elements and some of those bonds are relatively stable. Peptides, bearing metal binding ligands, are known to bind radiometals stably and at very high specific activity. The approach utilized in the present method was to first bind the F-18 to a metal and then chelate the F-18 metal complex with a ligand on the peptide. An initial question was which metal (or other element e.g. boron) to choose. The elements in group IIIA (boron, aluminum, gallium, indium, and thallium) were the first choice. Lutetium may also be of use. The metal binding ligand of use to attach an F-18-metal complex to a protein, peptide or other molecule is also important, as different metals bind with different affinities to various chelating agents, such as NOTA, NETA, DOTA, DTPA and other chelating groups discussed in more detail below.

Alternatively, one might attach the metal or other atom to the peptide first and then add the F-18. The second approach might work better, for example, for a boron fluoride connection.

Aluminum fluoride complexes are reported to be stable in-vitro (Martinez et al, Inorg. Chem. 1999; 38: 4765-4660; Antonny et al. J. Biol. Chem. 1992; 267: 6710-6718). Aluminum fluoride becomes incorporated into bone and into the enamel of teeth so the complexes can also be stable in-vivo (Li, Crit. Rev. Oral Biol. Med. 2003; 14: 100-114).

The skilled artisan will realize that virtually any delivery molecule can be used to attach the F-18 for imaging purposes, so long as it contains derivatizable groups that may be modified without affecting the ligand-receptor binding interaction between the delivery molecule and the cellular or tissue target receptor. Although the Examples below concern F-18 labeled peptide moieties, many other types of delivery molecules, such as oligonucleotides, hormones, growth factors, cytokines, chemokines, angiogenic factors, anti-angiogenic factors, immunomodulators, proteins, nucleic acids, antibodies, antibody fragments, drugs, interleukins, interferons, oligosaccharides, polysaccharides, lipids, etc. may be F-18 labeled and utilized for imaging purposes. Similarly, the type of diseases or conditions that may be imaged is limited only by the availability of a suitable delivery molecule for targeting a cell or tissue associated with the disease or condition. Many such delivery molecules are known, as exemplified in the Examples below. For example, any protein or peptide that binds to a diseased tissue or target, such as cancer, may be labeled with F-18 by the disclosed methods and used for detection and/or imaging. In certain embodiments, such proteins or peptides may include, but are not limited to, antibodies or antibody fragments that bind to tumor-associated antigens (TAAs). Any known TAA-binding antibody or fragment may be labeled with F-18 by the described methods and used for imaging and/or detection of tumors, for example by PET scanning or other known techniques.

In certain Examples below, the exemplary F-18 labeled peptides may be of use for imaging purposes as targetable constructs in a pre-targeting method, utilizing bispecific or multispecific antibodies or antibody fragments. In this case, the antibody or fragment will comprise one or more binding sites for a target associated with a disease or condition, such as a tumor-associated or autoimmune disease-associated antigen or an antigen produced or displayed by a pathogenic organism, such as a virus, bacterium, fungus or other microorganism. A second binding site will specifically bind to the targetable construct. Methods for pre-targeting using bispecific or multispecific antibodies are well known in the art (see, e.g., U.S. Pat. No. 6,962,702, the entire contents of which are incorporated herein by reference.) Similarly, antibodies or fragments thereof that bind to targetable constructs are also well known in the art (Id.), such as the 679 monoclonal antibody that binds to HSG (histamine succinyl glycine). Generally, in pretargeting methods the bispecific or multispecific antibody is administered first and allowed to bind to cell or tissue target antigens. After an appropriate amount of time for unbound antibody to clear from circulation, the e.g. F-18 labeled targetable construct is administered to the patient and binds to the antibody localized to target cells or tissues, then an image is taken for example by PET scanning.

In an exemplary embodiment, a non-peptide receptor targeting agent such as folic acid may be conjugated to NOTA or another chelating moiety and then labeled with, for example, an F-18 metal complex that binds to NOTA. Such non-peptide receptor targeting agents may include, for example, TA 138, a non-peptide antagonist for the integrin $\alpha_v\beta_3$ receptor (Liu et al., 2003, Bioconj. Chem. 14:1052-56). Similar non-peptide targeting agents known in the art that can be conjugated to DOTA, NOTA or another chelating agent for F-18 metal complexes may be utilized in the claimed methods. Other receptor targeting agents are known in the art, such as the somatostatin receptor targeting agent In-DTPA octreotide (TYCO®). As discussed below, an F-18-metal complex could potentially be chelated using DTPA and used for imaging purposes. The NODAGATOC peptide could be labeled with AlF-18 for somatostatin receptor targeting (Eisenwiener et. al. Bioconj. Chem. 2002, 13(3):530-41). Other methods of receptor targeting imaging using metal chelates are known in the art and may be utilized in the practice of the claimed methods (see, e.g., Andre et al., 2002, J. Inorg. Biochem. 88:1-6; Pearson et al., 1996, J. Med., Chem. 39:1361-71).

Imaging techniques and apparatus for F-18 imaging by PET scanning are also well known in the art (see, e.g., U.S. Pat. Nos. 6,358,489; 6,953,567; Page et al., Nuclear Medicine And Biology, 21:911-919, 1994; Choi et al., Cancer Research 55:5323-5329, 1995; Zalutsky et al., J. Nuclear Med., 33:575-582, 1992) and any such known PET imaging technique or apparatus may be utilized.

Although the Examples below demonstrate the use of F-18 metal complexes for PET imaging, the skilled artisan will realize that stable metal-fluorine complexes, such as the non-radioactive Al-27 and F-19 complex, could also be bound to NOTA or other chelators and attached to peptides or other targeting agents for use as an MRI contrast agent. The AlF NOTA complexes could also be attached to polymers for MRI imaging. The AlF NOTA derivatives could be used as PARACEST MRI imaging agents (Woessner et. al. Magn. Reson. Med. 2005, 53: 790-99).

BRIEF DESCRIPTION OF THE DRAWINGS

The following Figures are included to illustrate particular embodiments of the invention and are not meant to be limiting as to the scope of the claimed subject matter.

FIG. 12. Difference in structure between C-NETA and L-NETA.

DETAILED DESCRIPTION

Figure 1:
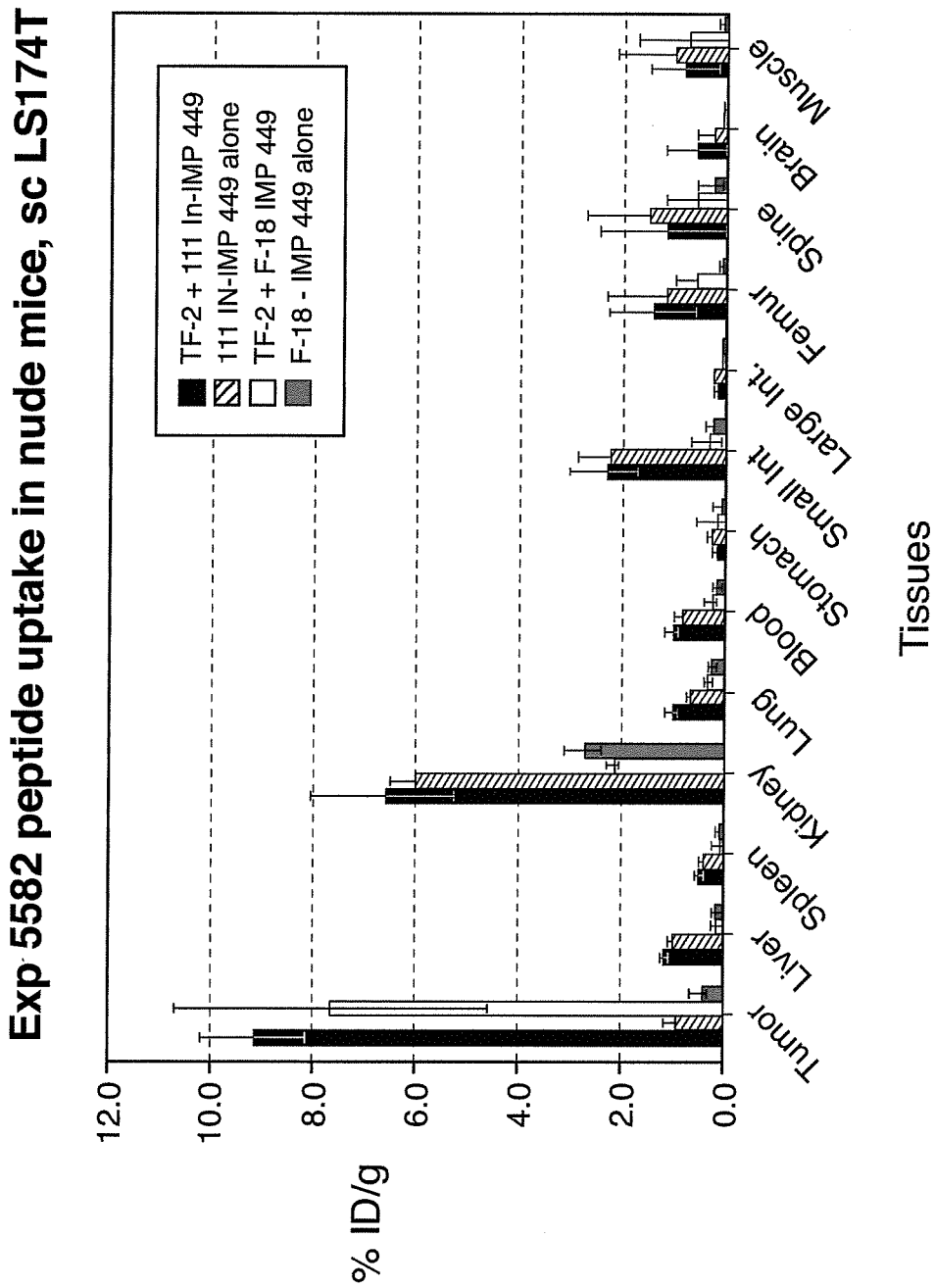
FIG. 1. Comparative biodistribution of In-111 and F-18 labeled IMP 449 in mice with or without TF2 bispecific antibody.

The following definitions are provided to facilitate understanding of the disclosure herein. Terms that are not explicitly defined are used according to their plain and ordinary meaning.

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, "about" means within plus or minus ten percent of a number. For example, "about 100" would refer to any number between 90 and 110.

As used herein, a "peptide" refers to any sequence of naturally occurring or non-naturally occurring amino acids of between 2 and 100 amino acid residues in length, more preferably between 2 and 10, more preferably between 2 and 6 amino acids in length. An "amino acid" may be an L-amino acid, a D-amino acid, an amino acid analogue, an amino acid derivative or an amino acid mimetic.

As used herein, a labeled molecule is "purified" when the labeled molecule is partially or wholly separated from unlabeled molecules, so that the fraction of labeled molecules is enriched compared to the starting mixture. A "purified" labeled molecule may comprise a mixture of labeled and unlabeled molecules in almost any ratio, including but not limited to about 5:95; 10:90; 15:85; 20:80; 25:75; 30:70; 40:60; 50:50; 60:40; 70:30; 75:25; 80:20; 85:15; 90:10; 95:5; 97:3; 98:2; 99:1 or 100:0.

As used herein, the term "pathogen" includes, but is not limited to fungi, viruses, parasites and bacteria, including but not limited to human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, *Streptococcus agalactiae, Legionella pneumophilia, Streptococcus pyogenes, Escherichia coli, Neisseria gonorrhoeae, Neisseria meningitidis, Pneumococcus, Hemophilis influenzae* B, *Treponema pallidum*, Lyme disease spirochetes, *Pseudomonas aeruginosa, Mycobacterium leprae, Brucella abortus, Mycobacterium tuberculosis* and *Chlostridium tetani*.

As used herein, a "radiolysis protection agent" refers to any molecule, compound or composition that may be added to an F-18 labeled complex or molecule to decrease the rate of breakdown of the F-18 labeled complex or molecule by radiolysis. Any known radiolysis protection agent, including but not limited to ascorbic acid, may be used.

Targetable Construct Peptides

In certain embodiments, the F-18 labeled moiety may comprise a peptide or other targetable construct. F-18 labeled peptides (or proteins) may be selected to bind directly to a targeted cell, tissue, pathogenic organism or other target for imaging and/or detection. In other embodiments, F-18 labeled peptides may be selected to bind indirectly, for example using a bispecific antibody with one or more binding sites for a targetable construct peptide and one or more binding sites for a target antigen associated with a disease or condition. Bispecific antibodies may be used, for example, in a pretargeting technique wherein the antibody may be administered first to a subject. Sufficient time may be allowed for the bispecific antibody to bind to a target antigen and for unbound antibody to clear from circulation. Then a targetable construct, such as an F-18 labeled peptide, may be administered to the subject and allowed to bind to the bispecific antibody and localize to the diseased cell or tissue, after which the distribution of the F-18 labeled targetable construct may be determined by PET scanning or other known techniques.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may also be used.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons, including the metal ions in the chelates. More usually, the targetable construct peptide will have four or more residues, such as the peptide DOTA-Phe-Lys(HSG)-Tyr-Lys(HSG)-NH$_2$ (SEQ ID NO: 1). wherein DOTA is 1,4,7,10-tetraazacyclododecanetetraacetic acid and HSG is the histamine succinyl glycyl group. Alternatively, the DOTA may be replaced by a NOTA (1,4,7-triaza-cyclononane-N,N', N''-triacetic acid), TETA (p-bromoacetamido-benzyl-tetraethylaminetetraacetic acid), NETA ([2-(4,7-bis-carboxymethyl-[1,4,7]triazacyclononan-1-yl-ethyl]-2-carbonylmethyl-amino]-tetraacetic acid) or other known chelating moiety.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as a Boc group, while N-terminal residues may be acetylated to increase serum stability. Such protecting groups will be known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity.

The haptens of the immunogen comprise a recognition moiety, for example, a chemical hapten. Using a chemical hapten, preferably the HSG hapten, high specificity of the linker for the antibody is exhibited. Antibodies raised to the HSG hapten are known and can be easily incorporated into the appropriate bispecific antibody (see, e.g., U.S. Pat. Nos. 6,962,702; 7,138,103 and 7,300,644, incorporated herein by reference with respect to the Examples sections). Thus, binding of the linker with the attached hapten would be highly specific for the antibody or antibody fragment.

Chelate Moieties

In some embodiments, an F-18 labeled molecule may comprise one or more hydrophilic chelate moieties, which can bind metal ions and also help to ensure rapid in vivo clearance. Chelators may be selected for their particular metal-binding properties, and may be readily interchanged.

Particularly useful metal-chelate combinations include 2-benzyl-DTPA and its monomethyl and cyclohexyl analogs. Macrocyclic chelators such as NOTA (1,4,7-triaza-cyclononane-N,N',N''-triacetic acid), DOTA, TETA (p-bromoacetamido-benzyl-tetraethylaminetetraacetic acid) and NETA are also of use with a variety of metals, that may potentially be used as ligands for F-18 conjugation.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides. Porphyrin chelators may be used with numerous metal complexes. More than one type of chelator may be conjugated to a carrier to bind multiple metal ions. Chelators such as those disclosed in U.S. Pat. No. 5,753,206, especially thiosemicarbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands. It can be useful to link more than one type of chelator to a peptide. Because antibodies to a di-DTPA hapten are known (Barbet et al., U.S. Pat. Nos. 5,256,395) and are readily coupled to a targeting antibody to form a bispecific antibody, it is possible to use a peptide hapten with cold diDTPA chelator and another chelator for binding an F-18 complex, in a pretargeting protocol. One example of such a peptide is Ac-Lys(DTPA)-Tyr-Lys (DTPA)-Lys(Tscg-Cys)-NH$_2$ (SEQ ID NO:2). Other hard acid chelators such as DOTA, TETA and the like can be substituted for the DTPA and/or Tscg-Cys groups, and MAbs specific to them can be produced using analogous techniques to those used to generate the anti-di-DTPA MAb.

Another useful chelator may comprise a NOTA-type moiety, for example as disclosed in Chong et al. (Rational design and generation of a bimodal bifunctional ligand for antibody-targeted radiation cancer therapy, *J. Med. Chem.*, e-published on Dec. 7, 2007, incorporated herein by reference). Chong et al. disclose the production and use of a bifunctional C-NETA ligand, based upon the NOTA structure, that when complexed with $^{177}$Lu or $^{205/206}$Bi showed stability in serum for up to 14 days. The chelators are not limiting and these and other examples of chelators that are known in the art and/or described in the following Examples may be used in the practice of the invention.

It will be appreciated that two different hard acid or soft acid chelators can be incorporated into the targetable construct, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be attached to F-18, to be incorporated into a targetable construct for eventual capture by a pretargeted bispecific antibody.

Methods of Administration

In various embodiments, bispecific antibodies and targetable constructs may be used for imaging normal or diseased tissue and organs (see, e.g. U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference in its Examples section).

The administration of a bispecific antibody (bsAb) and an F-18 labeled targetable construct may be conducted by administering the bsAb antibody at some time prior to administration of the targetable construct. The doses and timing of the reagents can be readily devised by a skilled artisan, and are dependent on the specific nature of the reagents employed. If a bsAb-F(ab')$_2$ derivative is given first, then a waiting time of 24-72 hr (alternatively 48-96 hours) before administration of the targetable construct would be appropriate. If an IgG-Fab' bsAb conjugate is the primary targeting vector, then a longer waiting period before administration of the targetable construct would be indicated, in the range of 3-10 days. After sufficient time has passed for the bsAb to target to the diseased tissue, the F-18 labeled targetable construct is administered. Subsequent to administration of the targetable construct, imaging can be performed.

Certain embodiments concern the use of multivalent target binding proteins which have at least three different target binding sites as described in patent application Ser. No. 60/220,782. Multivalent target binding proteins have been made by cross-linking several Fab-like fragments via chemical linkers. See U.S. Pat. Nos. 5,262,524; 5,091,542 and Landsdorp et al. Euro. J. Immunol. 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al. Protein Engineering 10(4): 423-433 (1997).

Alternatively, a technique known as "dock-and-lock" (DNL), described in more detail below, has been demonstrated for the simple and reproducible construction of a variety of multivalent complexes, including complexes comprising two or more different antibodies or antibody fragments. (See, e.g., U.S. patent application Ser. Nos. 11/389,358, filed Mar. 24, 2006; Ser. No. 11/391,584, filed Mar. 28, 2006; Ser. No. 11/478,021, filed Jun. 29, 2006; Ser. No. 11/633,729, filed Dec. 5, 2006; and Ser. No. 11/925,408, filed Oct. 26, 2007, the text of each of which is incorporated herein by reference in its entirety.) Such constructs are also of use for the practice of the claimed methods and compositions described herein.

A clearing agent may be used which is given between doses of the bispecific antibody (bsAb) and the targetable construct. A clearing agent of novel mechanistic action may be used, namely a glycosylated anti-idiotypic Fab' fragment targeted against the disease targeting arm(s) of the bsAb. In one example, anti-CEA (MN-14 Ab)×anti-peptide bsAb is given and allowed to accrete in disease targets to its maximum extent. To clear residual bsAb, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the F-18 labeled targetable construct is given to the subject. The WI2 Ab to the MN-14 arm of the bsAb has a high affinity and the clearance mechanism differs from other disclosed mechanisms (see Goodwin et al., ibid), as it does not involve cross-linking, because the WI2-Fab' is a monovalent moiety. However, alternative methods and compositions for clearing agents are known and any such known clearing agents may be used.

Formulation and Administration

The F-18 labeled molecules may be formulated to obtain compositions that include one or more pharmaceutically suitable excipients, one or more additional ingredients, or some combination of these. These can be accomplished by known methods to prepare pharmaceutically useful dosages, whereby the active ingredients (i.e., the F-18 labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parental injection. Injection may be intravenous, intraarterial, intralymphatic, intrathecal, or intracavitary (i.e., parenterally). In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising F-18 labeled molecules can be used for intravenous administration via, for example, bolus injection or continuous infusion. Compositions for injection can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate, TRIS (hydroxymethyl)aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included. The compositions may be administered to a mammal subcutaneously, intravenously, intramuscularly or by other parenteral routes. Moreover, the administration may be by continuous infusion or by single or multiple boluses.

Where bispecific antibodies are administered, for example in a pretargeting technique, the dosage of an administered antibody for humans will vary depending upon such factors as the patient's age, weight, height, sex, general medical condition and previous medical history. Typically, for imaging purposes it is desirable to provide the recipient with a dosage of bispecific antibody that is in the range of from about 1 mg to 200 mg as a single intravenous infusion, although a lower or higher dosage also may be administered as circumstances dictate. Typically, it is desirable to provide the recipient with a dosage that is in the range of from about 10 mg per square meter of body surface area or 17 to 18 mg of the antibody for the typical adult, although a lower or higher dosage also may be administered as circumstances dictate. Examples of dosages of bispecific antibodies that may be administered to a human subject for imaging purposes are 1 to 200 mg, more preferably 1 to 70 mg, most preferably 1 to 20 mg, although higher or lower doses may be used.

In general, the dosage of F-18 label to administer will vary depending upon such factors as the patient's age, weight, height, sex, general medical condition and previous medical history. Preferably, a saturating dose of the F-18 labeled molecules is administered to a patient. For administration of F-18 labeled molecules, the dosage may be measured by millicuries. A typical range for F-18 imaging studies would be five to 10 mCi.

Administration of Peptides

Various embodiments of the claimed methods and/or compositions may concern one or more F-18 labeled peptides to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection. Where, for example, F-18 labeled peptides are administered in a pretargeting protocol, the peptides would preferably be administered i.v.

Unmodified peptides administered orally to a subject can be degraded in the digestive tract and depending on sequence and structure may exhibit poor absorption across the intestinal lining. However, methods for chemically modifying peptides to render them less susceptible to degradation by endogenous proteases or more absorbable through the alimentary tract are well known (see, for example, Blondelle et al., 1995, Biophys. J. 69:604-11; Ecker and Crooke, 1995, Biotechnology 13:351-69; Goodman and Ro, 1995, BURGER'S MEDICINAL CHEMISTRY AND DRUG DISCOVERY, VOL. I, ed. Wollf, John Wiley & Sons; Goodman and Shao, 1996, Pure & Appl. Chem. 68:1303-08). Methods for preparing libraries of peptide analogs, such as peptides containing D-amino acids; peptidomimetics consisting of organic molecules that mimic the structure of a peptide; or peptoids such as vinylogous peptoids, have also been described and may be used to construct peptide based F-18 labeled molecules suitable for oral administration to a subject.

In certain embodiments, the standard peptide bond linkage may be replaced by one or more alternative linking groups, such as $CH_2$—NH, $CH_2$—S, $CH_2$—$CH_2$, CH=CH, CO—$CH_2$, CHOH—$CH_2$ and the like. Methods for preparing peptide mimetics are well known (for example, Hruby, 1982, Life Sci 31:189-99; Holladay et al., 1983, Tetrahedron Lett. 24:4401-04; Jennings-White et al., 1982, Tetrahedron Lett. 23:2533; Almquiest et al., 1980, J. Med. Chem. 23:1392-98; Hudson et al., 1979, Int. J. Pept. Res. 14:177-185; Spatola et al., 1986, Life Sci 38:1243-49; U.S. Pat. Nos. 5,169,862; 5,539,085; 5,576,423, 5,051,448, 5,559,103, each incorporated herein by reference.) Peptide mimetics may exhibit enhanced stability and/or absorption in vivo compared to their peptide analogs.

Alternatively, peptides may be administered by oral delivery using N-terminal and/or C-terminal capping to prevent exopeptidase activity. For example, the C-terminus may be capped using amide peptides and the N-terminus may be capped by acetylation of the peptide. Peptides may also be cyclized to block exopeptidases, for example by formation of cyclic amides, disulfides, ethers, sulfides and the like.

Peptide stabilization may also occur by substitution of D-amino acids for naturally occurring L-amino acids, particularly at locations where endopeptidases are known to act. Endopeptidase binding and cleavage sequences are known in the art and methods for making and using peptides incorporating D-amino acids have been described (e.g., U.S. Patent Application Publication No. 20050025709, McBride et al., filed Jun. 14, 2004, the Examples section of which is incorporated herein by reference). In certain embodiments, peptides and/or proteins may be orally administered by co-formulation with proteinase- and/or peptidase-inhibitors.

Other methods for oral delivery of therapeutic peptides are disclosed in Mehta ("Oral delivery and recombinant production of peptide hormones," June 2004, BioPharm International). The peptides are administered in an enteric-coated solid dosage form with excipients that modulate intestinal proteolytic activity and enhance peptide transport across the intestinal wall. Relative bioavailability of intact peptides using this technique ranged from 1% to 10% of the administered dosage. Insulin has been successfully administered in dogs using enteric-coated microcapsules with sodium cholate and a protease inhibitor (Ziv et al., 1994, J. Bone Miner. Res. 18 (Suppl. 2):792-94. Oral administration of peptides has been performed using acylcarnitine as a permeation enhancer and an enteric coating (Eudragit L30D-55, Rohm Pharma Polymers, see Mehta, 2004). Excipients of use for orally administered peptides may generally include one or more inhibitors of intestinal proteases/peptidases along with detergents or other agents to improve solubility or absorption of the peptide, which may be packaged within an enteric-coated capsule or tablet (Mehta, 2004). Organic acids may be included in the capsule to acidify the intestine and inhibit intestinal protease activity once the capsule dissolves in the intestine (Mehta, 2004). Another alternative for oral delivery of peptides would include conjugation to polyethylene glycol (PEG)-based amphiphilic oligomers, increasing absorption and resistance to enzymatic degradation (Soltero and Ekwuribe, 2001, Pharm. Technol. 6:110).

Methods for Raising Antibodies

Abs to peptide backbones may be generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the targetable construct, e.g., In(III)-DTPA chelates. Monoclonal mouse antibodies to an In(III)-di-DTPA are known (Barbet '395 supra).

Targeting antibodies of use, for example as components of bispecific antibodies, may be specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or subcellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744, each incorporated herein by reference. Recent reports on tumor associated antigens (TAAs) include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44); and Ren et al. (2005, *Ann. Surg.* 242:55-63), each incorporated herein by reference with respect to the TAAs identified.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361,644 and 4,444,744.

Another marker of interest is transmembrane activator and CAML-interactor (TACI). See Yu et al. Nat. Immunol. 1:252-256 (2000). Briefly, TACI is a marker for B-cell malignancies (e.g., lymphoma). Further it is known that TACI and B cell maturation antigen (BCMA) are bound by the tumor necrosis factor homolog—a proliferation-inducing ligand (APRIL). APRIL stimulates in vitro proliferation of primary B and T cells and increases spleen weight due to accumulation of B cells in vivo. APRIL also competes with TALL-I (also called BLyS or BAFF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

Exemplary target antigens of use for imaging various diseases or conditions, such as a malignant disease, a cardiovascular disease, an infectious disease, an inflammatory disease, an autoimmune disease, or a neurological disease may include colon-specific antigen-p (CSAp), carcinoembryonic antigen (CEA), CD4, CD5, CD8, CD14, CD15, CD19, CD20, CD21, CD22, CD23, CD25, CD30, CD45, CD74, CD79a, CD80, HLA-DR, Ia, Ii, MUC1, MUC2, MUC3, MUC4, NCA (CEACAM6 or CD66a-d and CD67, as well as CD138), EGFR, HER 2/neu, TAG-72, EGP-1, EGP-2, A3, KS-1, Le(y), S100, PSMA, PSA, tenascin, folate receptor, VEGFR, PlGF, ILGF-1, necrosis antigens, IL-2, IL-6, T101, MAGE, or a combination of these antigens. In particular, antigens may include carcinoembryonic antigen (CEA), tenascin, epidermal growth factor receptor, platelet derived growth factor receptor, fibroblast growth factor receptors, vascular endothelial growth factor receptors, gangliosides, HER/2neu receptors and combinations of these antigens.

Where imaging or detection involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD52, CD54, CD67, CD74, CD79a, CD80, CD126, CD138, CD154, B7, MUC1, Ia, Ii, HM1.24, HLA-DR, tenascin, VEGF, PlGF, ED-B fibronectin, an oncogene, an oncogene product, CD66a-d, necrosis antigens, IL-2, T101, TAG, IL-6, MIF, TRAIL-R1 (DR4) and TRAIL-R2 (DR5).

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., Proc. Nat'l Acad. Sci. USA 86: 3833 (1989), which is incorporated by reference in its entirety. Techniques for producing humanized MAbs are described, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993), each of which is incorporated herein by reference in its entirety.

Alternatively, fully human antibodies can be obtained from transgenic non-human animals. See, e.g., Mendez et al., Nature Genetics, 15: 146-156 (1997); U.S. Pat. No. 5,633,425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., Nature Genetics, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment may be derived from human antibody fragments isolated from a combinatorial immunoglobulin library. See, e.g., Barbas et al., METHODS: A Companion to Methods in Enzymology 2: 119 (1991), and Winter et al., Ann. Rev. Immunol. 12: 433 (1994), which are incorporated herein by reference. Many of the difficulties associated with generating monoclonal antibodies by B-cell immortalization can be overcome by engineering and expressing antibody fragments in $E.\ coli$, using phage display.

A similar strategy can be employed to obtain high-affinity scFv. See, e.g., Vaughn et al., Nat. Biotechnol., 14: 309-314 (1996). An scFv library with a large repertoire can be constructed by isolating V-genes from non-immunized human donors using PCR primers corresponding to all known $V_H$, $V_{kappa}$ and $V_{80}$ gene families. Following amplification, the $V_{kappa}$ and $V_{lambda}$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (NUNC®; MAX-ISORP®). Similar results can be achieved by constructing a combinatorial immunoglobulin library from lymphocytes or spleen cells of immunized rabbits and by expressing the scFv constructs in $P.\ pastoris$. See, e.g., Ridder et al., Biotechnology, 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., Br. J. Cancer, 78: 181-188 (1998); Osbourn et al., Immunotechnology, 2: 181-196 (1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain attached to human constant region sequences.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing bispecific antibodies include engineered recombinant Abs which have additional cysteine residues so that they crosslink more strongly than the more common immunoglobulin isotypes. See, e.g., FitzGerald et al., Protein Eng. 10:1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., Proc. Natl. Acad. Sci., 92: 7021-7025, 1995.

Preferred bispecific antibodies are those which incorporate the Fv of MAb Mu-9 and the Fv of MAb 679 or the Fv of MAb MN-14 and the Fv of MAb 679, and their human, chimerized or humanized counterparts. The MN-14, as well as its chimerized and humanized counterparts, are disclosed in U.S. Pat. No. 5,874,540. Also preferred are bispecific antibodies which incorporate one or more of the CDRs of Mu-9 or 679. The antibody can also be a fusion protein or a bispecific antibody that incorporates a Class III anti-CEA antibody and the Fv of 679. Class III antibodies, including Class III anti-CEA are discussed in detail in U.S. Pat. No. 4,818,709.

The skilled artisan will realize that bispecific antibodies may incorporate any antibody or fragment known in the art that has binding specificity for a target antigen that is known to be associated with a disease state or condition. Such known antibodies include, but are not limited to, hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318,), hLL2 (U.S. Pat. No. 7,074, 403), hMu-9 (U.S. Pat. No. 7,387,773), hL243 (U.S. patent application Ser. No. 11/368,296), hMN-14 (U.S. Pat. No. 6,676,924), hMN-15 (U.S. patent application Ser. No. 10/672,278) and hRS7 (U.S. Pat. No. 7,238,785), the text of each cited patent or application incorporated herein by reference in its entirety. The second MAb may also be selected from any anti-hapten antibody known in the art, including but not limited to h679 (U.S. Pat. No. 7,429,381) and 734 (U.S. patent application Ser. No. 10/776,470), the text of each of which is incorporated herein by reference in its entirety.

Various other antibodies of use are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; and U.S. Patent Application Publ. No. 20040185053; 20040202666; 20050271671; 20060193865; 20060210475; 20070087001; each incorporated herein by reference in its entirety.) Such known antibodies are of use for detection and/or imaging of a variety of disease states or conditions (e.g., hMN-14 or TF2 bsMAb (CEA-expressing carcinomas), hA20 bsMab (TF-4-lymphoma), hPAM4 (TF-10 pancreas cancers), RS7 bsMAb (lung, breast, ovarian, prostatic cancers), hMN-15 or hMN3 bsMAb (inflammation), human gp120 and/or gp41 bsMAbs (HIV), anti-platelet bsMab and anti-thrombin bsMAb (clot imaging), anti-myosin bsMAb (cardiac necrosis)).

Candidate anti-HIV antibodies include the anti-envelope antibody described by Johansson et al. (AIDS. Oct. 3, 2006; 20(15):1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agens Chemother. 2006; 50(5):1773-9, all incorporated herein in their entirety by reference.

In certain embodiments, the bsAb F-18 labeled targetable constructs may be used in intraoperative, intravascular, and/or endoscopic tumor and lesion detection, biopsy and therapy as described in U.S. Pat. No. 6,096,289.

General Techniques for Antibody Cloning and Construction

Various techniques, such as production of chimeric or humanized antibodies, may involve procedures of antibody cloning and construction. The antigen-binding $V_\kappa$ (variable light chain) and $V_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci., USA*, 86: 3833 (1989)). Based on the V gene sequences, a humanized MAb can then be designed and constructed as described by Leung et al. (*Mol. Immunol.*, 32: 1413 (1995)).

cDNA can be prepared from any known hybridoma line or transfected cell line producing a murine MAb by general molecular cloning techniques (Sambrook et al., Molecular Cloning, A laboratory manual, 2$^{nd}$ Ed (1989)). The $V_\kappa$ sequence for the MAb may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)).

PCR reaction mixtures containing 10 µl of the first strand cDNA product, 10 µl of 10×PCR buffer [500 mM KCl, 100 mM Tris-HCl (pH 8.3), 15 mM MgCl$_2$, and 0.01% (w/v) gelatin] (Perkin Elmer Cetus, Norwalk, Conn.), 250 µM of each dNTP, 200 nM of the primers, and 5 units of Taq DNA polymerase (Perkin Elmer Cetus) can be subjected to 30 cycles of PCR. Each PCR cycle preferably consists of denaturation at 94° C. for 1 min, annealing at 50° C. for 1.5 min, and polymerization at 72° C. for 1.5 min. Amplified VK and VH fragments can be purified on 2% agarose (BioRad, Richmond, Calif.). The humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites to facilitate in-frame ligation of the VκPCR products. PCR products for $V_H$ can be subcloned into a similar staging vector, such as the pBluescript-based VHpBS. Individual clones containing the respective PCR products may be sequenced by, for example, the method of Sanger et al. (*Proc. Natl. Acad. Sci., USA*, 74: 5463 (1977)).

Expression cassettes containing the Vκ and $V_H$ sequences, together with the promoter and signal peptide sequences, can be excised from VKpBR and VHpBS, respectively, by double restriction digestion as HindIII-BamHI fragments. The Vκ and $V_H$ expression cassettes can be ligated into appropriate expression vectors, such as pKh and pG1g, respectively (Leung et al., Hybridoma, 13:469 (1994)). The expression vectors can be co-transfected into an appropriate cell, e.g., myeloma Sp2/0-Ag14 (ATCC, VA), colonies selected for hygromycin resistance, and supernatant fluids monitored for production of a chimeric, humanized or human MAb by, for example, an ELISA assay. Alternatively, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gillies et al. (*J. Immunol. Methods* 125:191 (1989) and also shown in Losman et al., *Cancer,* 80:2660 (1997)). Another vector that is useful is the GS vector, as described in Barnes et al., *Cytotechnology* 32:109-123 (2000). Other appropriate mammalian expression systems are described in Werner et al., Arzneim.-Forsch./Drug Res. 48(II), Nr. 8, 870-880 (1998).

Co-transfection and assay for antibody secreting clones by ELISA, can be carried out as follows. About 10 µg of VKpKh (light chain expression vector) and 20 µg of VHpG1g (heavy chain expression vector) can be used for the transfection of $5\times10^6$ SP2/0 myeloma cells by electroporation (BioRad, Richmond, Calif.) according to Co et al., *J. Immunol.*, 148: 1149 (1992). Following transfection, cells may be grown in 96-well microtiter plates in complete HSFM medium (Life Technologies, Inc., Grand Island, N.Y.) at 37° C., 5% CO$_2$. The selection process can be initiated after two days by the addition of hygromycin selection medium (Calbiochem, San Diego, Calif.) at a final concentration of 500 units/ml of hygromycin. Colonies typically emerge 2-3 weeks post-electroporation. The cultures can then be expanded for further analysis. Transfectoma clones that are positive for the secretion of chimeric, humanized or human heavy chain can be identified by ELISA assay.

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2µ membrane. The filtered medium is passed through a protein A column (1×3 cm) at a flow rate of 1 ml/min. The resin is then washed with about 10 column volumes of PBS and protein Abound antibody is eluted from the column with 0.1 M glycine buffer (pH 3.5) containing 10 mM EDTA. Fractions of 1.0 ml are collected in tubes containing 10 µl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.).

The antibody concentration is determined by ELISA and its concentration adjusted to about 1 mg/ml using PBS. Sodium azide, 0.01% (w/v), is conveniently added to the sample as preservative.

Bispecific and Multispecific Antibodies

Bispecific antibodies can be prepared by techniques known in the art, for example, an anti-CEA tumor Ab and an anti-peptide Ab are both separately digested with pepsin to their respective F(ab')$_2$ fragments. The anti-CEA-Ab-F(ab')$_2$ is reduced with cysteine to generate Fab' monomeric units which are further reacted with the cross-linker bis(male-imido) hexane to produce Fab'-maleimide moieties. The anti-peptide Ab-F(ab')$_2$ is reduced with cysteine and the purified, recovered anti-peptide Fab'-SH is reacted with the anti-CEA-Fab'-maleimide to generate the Fab'×Fab' bi-specific Ab. Alternatively, the anti-peptide Fab'-SH fragment may be coupled with the anti-CEA F(ab')$_2$ to generate a F(ab')$_2$×Fab' construct, or with anti-CEA IgG to generate an IgG×Fab' bi-specific construct. In one embodiment, the IgG×Fab' construct can be prepared in a site-specific manner by attaching the antipeptide Fab' thiol group to anti-CEA IgG heavy-chain carbohydrate which has been periodate-oxidized, and subsequently activated by reaction with a commercially available hydrazide-maleimide cross-linker. The component Abs used can be chimerized or humanized by known techniques.

Numerous methods to produce bispecific or multispecific antibodies are known, as disclosed, for example, in U.S. Patent Application Publication No. 20050002945, filed Feb. 11, 2004, the entire text of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405, incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL), discussed in more detail below, has been utilized to produce combinations of virtually any desired antibodies, antibody fragments and other effector molecules (see, e.g., U.S. Patent Application Publ. Nos. 20060228357; 20060228300; 20070086942; 20070140966 and 20070264265, each incorporated herein by reference in its entirety). The DNL technique allows the assembly of monospecific, bispecific or multispecific antibodies, either as naked antibody moieties or in combination with a wide range of other effector molecules such as immunomodulators, enzymes, chemotherapeutic agents, chemokines, cytokines, diagnostic agents, therapeutic agents, radionuclides, imaging agents, anti-angiogenic agents, growth factors, oligonucleotides, hormones, peptides, toxins, pro-apoptotic agents, or a combination thereof. Any of the techniques known in the art for making bispecific or multispecific antibodies may be utilized in the practice of the presently claimed methods.

Bispecific or multispecific antibodies may incorporate any known antibody of therapeutic use. Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206' 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302;

5,874,540; 5,814,440; 5,798,229; 5,789,554; 5,776,456; 5,736,119; 5,716,595; 5,677,136; 5,587,459; 5,443,953; 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Dock-and-Lock (DNL)

In preferred embodiments, bispecific or multispecific antibodies or other constructs may be produced using the dock-and-lock technology (see, e.g., U.S. patent application Ser. Nos. 11/389,358; 11/391,584; 11/478,021; 11/633,729 and 11/925,408, each incorporated herein by reference in its entirety). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIIα and the AD of a certain amino acid sequence as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chimura et al., Proc. Natl. Acad. Sci. USA. 2001; 98:8480) to ligate site-specifically.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. No. 6,077,499; U.S. Ser. No. 09/597,580; U.S. Ser. No. 10/361,026; U.S. Ser. No. 09/337,756; U.S. Ser. No. 09/823,746; U.S. Ser. No. 10/116,116; U.S. Ser. No. 09/382,186; U.S. Ser. No. 10/150,654; U.S. Pat. No. 6,090,381; U.S. Pat. No. 6,472,511; U.S. Ser. No. 10/114,315; U.S. Provisional Application No. 60/386,411; U.S. Provisional Application No. 60/345,641; U.S. Provisional Application No. 60/3328,835; U.S. Provisional Application No. 60/426,379; U.S. Ser. No. 09/823,746; U.S. Ser. No. 09/337,756; U.S. Provisional Application No. 60/342,103; and U.S. Pat. No. 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Imaging Using Labeled Molecules

Methods of imaging using labeled molecules are well known in the art, and any such known methods may be used with the fluoride-labeled molecules disclosed herein. See, e.g., U.S. Pat. Nos. 6,241,964; 6,358,489; 6,953,567 and published U.S. Patent Application Publ. Nos. 20050003403; 20040018557; 20060140936, each incorporated herein by reference in its entirety. See also, Page et al., Nuclear Medicine And Biology, 21:911-919, 1994; Choi et al., Cancer Research 55:5323-5329, 1995; Zalutsky et al., J. Nuclear Med., 33:575-582, 1992; Woessner et. al. Magn. Reson. Med. 2005, 53: 790-99.

In certain embodiments, F-18 labeled molecules may be of use in imaging normal or diseased tissue and organs, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Additional methods are described in U.S. application Ser. No. 09/337,756 filed Jun. 22, 1999 and in U.S. application Ser. No. 09/823,746, filed Apr. 3, 2001. Such imaging can be conducted by direct F-18 labeling of the appropriate targeting molecules, or by a pretargeted imaging method, as described in Goldenberg et al. (2007, Update Cancer Ther. 2:19-31); Sharkey et al. (2008, Radiology 246: 497-507); Goldenberg et al. (2008, J. Nucl. Med. 49:158-63); Sharkey et al. (2007, Clin. Cancer Res. 13:5777s-5585s); McBride et al. (2006, J. Nucl. Med. 47:1678-88); Goldenberg et al. (2006, J. Clin. Oncol. 24:823-85), see also U.S. Patent Publication Nos. 20050002945, 20040018557, 20030148409 and 20050014207, each incorporated herein by reference.

Methods of diagnostic imaging with labeled peptides or MAbs are well-known. For example, in the technique of immunoscintigraphy, ligands or antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as $^{18}$F, $^{68}$Ga, $^{64}$Cu, and $^{124}$I. Such radionuclides may be imaged by well-known PET scanning techniques.

In preferred embodiments, the F-18 labeled peptides, proteins and/or antibodies are of use for imaging of cancer. Examples of cancers include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to detect or diagnose malignant or pre-malignant conditions. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be detected include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be detected include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

Kits

Various embodiments may concern kits containing components suitable for detecting, diagnosing and/or imaging diseased tissue in a patient by F-18 PET imaging. Exemplary kits may contain an antibody, fragment or fusion protein, such as a bispecific antibody of use in pretargeting methods as described herein. Other components may include a targetable construct for use with such bispecific antibodies. Preferably, the targetable construct is pre-conjugated to a chelating group that may be used to attach an F-18-Al complex or a complex of F-18 with a different metal. However, in alternative embodiments it is contemplated that a chelator may be included separately, to attach to an F-18-Al complex before conjugation of the F-18-Al-chelating moiety to a targetable construct or other targeting peptide, protein or other molecule. Although certain preferred embodiments described in the Examples below utilize bispecific antibodies and F-18 labeled targetable constructs in a pretargeting method, the skilled artisan will realize that in other embodiments, the F-18 labeling methods disclosed and claimed herein may be utilized with non-antibody targeting proteins, peptides or other molecules.

The kit may contain additional reagents and other components of use to attach freshly prepared F-18-Al to a targetable construct or other targeting molecule and/or, optionally to partially or fully purify an F-18-labeled targeting molecule from unlabeled targeting molecules, unincorporated F-18 and other components of the mixture. However, the skilled artisan will realize that in certain preferred embodiments, the efficiency of incorporation and labeling and the specific radioactivity of the labeled construct are sufficiently high that an unpurified F-18 labeled targeting molecule, prepared as described herein, may be utilized for PET imaging. In most preferred embodiments, the kit may contain all components needed to prepare and use an F-18 labeled protein, peptide or other molecule for PET imaging, other than freshly prepared F-18 which may be obtained from commercial sources.

If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used for certain applications.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1

F-18 Labeling of Peptide IMP 272

The first peptide that was prepared and labeled was IMP 272:
DTPA-Gln-Ala-Lys(HSG)-D-Tyr-Lys(HSG)-NH$_2$ MH$^+$ 1512

Acetate buffer solution—Acetic acid, 1.509 g was diluted in ~160 mL water and the pH was adjusted by the addition of 1 M NaOH then diluted to 250 mL to make a 0.1 M solution at pH 4.03.

Aluminum acetate buffer solution—A solution of aluminum was prepared by dissolving 0.1028 g of AlCl$_3$ hexahydrate in 42.6 mL DI water. A 4 mL aliquot of the aluminum solution was mixed with 16 mL of a 0.1 M NaOAc solution at pH 4 to provide a 2 mM Al stock solution.

IMP 272 acetate buffer solution—Peptide, 0.0011 g, 7.28×10$^{-7}$ mol IMP 272 was dissolved in 364 µL of the 0.1 M pH 4 acetate buffer solution to obtain a 2 mM stock solution of the peptide.

F-18 Labeling of IMP 272—A 3 µL aliquot of the aluminum stock solution was placed in a REACTI-VIAL™ and mixed with 50 µL F-18 (as received) and 3 µL of the IMP 272 solution. The solution was heated in a heating block at 110° C. for 15 min and analyzed by reverse phase HPLC. The HPLC trace (not shown) showed 93% free F-18 and 7% bound to the peptide. An additional 10 µL of the IMP 272 solution was added to the reaction and it was heated again and analyzed by reverse phase HPLC (not shown). The HPLC trace showed 8% F-18 at the void volume and 92% of the activity attached to the peptide. The remainder of the peptide solution was incubated at room temperature with 150 µL PBS for ~1 hr and then examined by reverse phase HPLC. The HPLC (not shown) showed 58% F-18 unbound and 42% still attached to the peptide. The data indicate that F-18-Al-DTPA complex may be unstable when mixed with phosphate.

Reverse Phase HPLC—Reverse phase HPLC analysis was done under the following conditions:
Column: WATERS® XTERRA™ MS C$_{18}$ 5 µm, 4.6×250 mm
Flow Rate: 1 mL/min
Gradient Buffers: Buffer C, 0.1% NH$_4$OAc in DI water, Buffer D, 90% acetonitrile 10% water and 0.1% NH$_4$OAc
Gradient: 100% Buffer C to 100% Buffer D using a linear gradient over 30 min.
Run Time: 30 min Size Exclusion HPLC—The size exclusion HPLC was done under the following conditions:
Column: BIORAD® BIO-SIL™ SEC 250, 300×7.8 mm
Gradient: Isocratic
Eluent Buffer: 0.2 M Phosphate pH 6.8
Flow Rate: 1 mL/min
Run Time: 30 min All radiometric traces were obtained using a PERKIN ELMER® 610Tr to monitor the emission of F-18. Tables 1-3 are tabular representations of the data.

TABLE 1

F-18 + IMP 272 + AlCl₃ heated at 110° C. for 15 min, followed by analysis by reverse phase HPLC.
Regions: F-18    Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.20 | 2.30 | 2.20 | 130.0 | | | |
| Region 1 | 2.30 | 3.30 | 2.60 | 85270.0 | 200050.0 | 93.15 | 96.31 |
| Bkg 2 | 4.40 | 4.50 | 4.40 | 210.0 | | | |
| Region 2 | 8.70 | 9.80 | 9.00 | 5590.0 | 14720.0 | 6.85 | 7.09 |
| 2 Peaks | | | | | 214770.0 | 100.00 | 103.40 |

TABLE 2

F-18 + excess IMP 272 + AlCl₃ heated at 110° C. for 15 min, followed by analysis by reverse phase HPLC.
Regions: F-18    Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.20 | 2.30 | 2.20 | 340.0 | | | |
| Region 1 | 2.40 | 3.20 | 2.70 | 6450.0 | 20549.6 | 7.76 | 8.23 |
| Bkg 2 | 7.10 | 7.20 | 7.10 | 630.0 | | | |
| Region 2 | 7.30 | 8.70 | 8.50 | 3140.0 | 13113.6 | 4.95 | 5.25 |
| Region 3 | 8.70 | 10.00 | 9.00 | 93700.0 | 231023.9 | 87.28 | 92.57 |
| Bkg 3 | 10.70 | 10.80 | 10.70 | 520.0 | | | |
| 3 Peaks | | | | | 264687.1 | 100.00 | 106.06 |

TABLE 3

Phosphate Challenge in PBS for 90 min at room temp. Aliquot of F-18 + excess IMP 272 + AlCl₃ heated at 110° C. for 15 min and analyzed by reverse phase HPLC.
Regions: F-18    Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.00 | 2.10 | 2.00 | 350.0 | | | |
| Region 1 | 2.40 | 3.30 | 2.70 | 81930.0 | 162403.6 | 58.23 | 62.44 |
| Bkg 2 | 4.20 | 4.30 | 4.20 | 410.0 | | | |
| Bkg 3 | 7.50 | 7.60 | 7.50 | 780.0 | | | |
| Region 2 | 7.80 | 8.60 | 8.40 | 2110.0 | 5564.7 | 2.00 | 2.14 |
| Region 3 | 8.60 | 9.80 | 8.90 | 44590.0 | 110942.0 | 39.78 | 42.66 |
| Bkg 4 | 10.50 | 10.60 | 10.50 | 460.0 | | | |
| 3 Peaks | | | | | 278910.3 | 100.00 | 107.24 |

The labeled peptide was purified by applying the labeled peptide solution onto a 1 cc (30 mg) WATERS® HLB column (Part #186001879) and washing with 300 μL water to remove unbound F-18. The peptide was eluted by washing the column with 2×100 μL 1:1 MeOH/H₂O. The purified peptide was incubated in water at 25° C. and analyzed by reverse phase HPLC (not shown). The HPLC analysis showed that the F-18 labeled IMP 272 was not stable in water. After 40 min incubation in water about 17% of the F-18 was released from the peptide, while 83% was retained (not shown).

Example 2

Immunoreactivity of F-18 IMP 272

The peptide (16 μL 2 mM IMP 272, 48 μg) was labeled with F-18 and analyzed for antibody binding by size exclusion HPLC. The size exclusion HPLC showed that the peptide bound hMN-14×679 but did not bind to the irrelevant bispecific antibody hMN-14×734 (not shown).

Example 3

IMP 272 F-18 Labeling with Other Metals

A ~3 μL aliquot of the metal stock solution ($6 \times 10^{-9}$ mol) was placed in a polypropylene cone vial and mixed with 75 μL F-18 (as received), incubated at room temperature for ~2 min and then mixed with 20 μL of a 2 mM ($4 \times 10^{-8}$ mol) IMP 272 solution in 0.1 M NaOAc pH 4 buffer. The solution was heated in a heating block at 100° C. for 15 min and analyzed by reverse phase HPLC. IMP 272 was labeled with indium (24%), gallium (36%), zirconium (15%), lutetium (37%) and yttrium (2%) (not shown). These results demonstrate that the F-18 metal labeling technique is not limited to an aluminum ligand, but can also utilize other metals as well. It is anticipated that with different metal ligands, different chelating moieties may be utilized to optimize binding of an F-18-metal conjugate.

Example 4

Standard F-18 Peptide Labeling Conditions Used to Screen Other Peptides for Al-$^{18}$F Binding A 3 µL aliquot of the 2 mM aluminum stock solution was placed in a polypropylene cone vial and mixed with 50 µL F-18 (as received), incubated at room temperature for ~2 min and then mixed with 16 to 20 µL of a 2 mM peptide solution in 0.1 M NaOAc pH 4 buffer. The solution was heated in a heating block at 100° C. for 15 min and analyzed by reverse phase HPLC (PHENOMENEX™, GEMINI®, 5µ, C-18, 110A, 250×4.6 mm HPLC Column).

Peptides Tested

IMP 272: DTPA-Gln-Ala-Lys(HSG)-D-Tyr-Lys(HSG)-NH$_2$ MH$^+$ 1512

IMP 288 DOTA-D-Tyr-D-Lys(HSG)-D-Glu-D-Lys(HSG)-NH$_2$ MH$^+$ 1453

IMP 326 DTPA-ITC-NH—NH-Phe-CO-D-Tyr-D-Lys(HSG)-D-Glu-D-Lys(HSG)-NH$_2$ MH$^+$ 1477

IMP 329 Deferoxamine-NH—CS—NH—NH-Ph-CO-D-Tyr-D-Lys(HSG)-D-Glu-D-Lys(HSG)-NH$_2$ MH$^+$ 1804

IMP 331 NTA-iAsp-D-Ala-D-Lys(HSG)-D-Tyr-D-Lys(HSG)-NH$_2$ MH$^+$ 1240

IMP 332 EDTADpr-D-Ala-D-Lys(HSG)-D-Ala-D-Lsy(HSG)-NH$_2$ MH$^+$ 1327

IMP 333 DTPA-Dpr(DTPA)-D-Ala-D-Lys(HSG)-D-Ala-D-Lys(HSG)-NH$_2$ MH$^+$ 1845

IMP 334 (H$_2$O$_3$P)$_2$—C(OH)—(CH2)$_3$—NH-Gly-D-Lys(HSG)-D-Glu-D-Lys(HSG)-NH$_2$ MH$^+$ 1192

IMP 337 Ac-D-Ser(PO$_3$H$_2$)-D-Ser(PO$_3$H$_2$)-D-Ala-D-Lys(HSG)-D-Ala-D-Lys(HSG)-NH$_2$ MH$^+$ 1291

IMP 338 Ac-D-Ser(PO$_3$H$_2$)-D-Ala-D-Lys(HSG)-D-Ala-D-Lys(HSG)-NH$_2$ MH$^+$ 1126

IMP 345 DTPA-D-Ser(PO$_3$H$_2$)-D-Ala-D-Lys(HSG)-D-Ala-D-Lys(HSG)-NH$_2$ MH$^+$ 1459

IMP 349 DTPA-D-Cys((H$_2$O$_3$P)$_2$—CH—CH$_2$—S)-D-Ala-D-Lys(HSG)-D-Ala-D-Lys(HSG)-NH$_2$ MH$^+$ 1583

IMP 361 DTPA-Dpr(BrCH$_2$CO-)-D-Ala-D-Lys(HSG)-D-Ala-D-Lys(HSG)-NH$_2$ MH$^+$ 1498

IMP 366 DTPA-Dpr(Ph-S—CH$_2$CO-)-D-Ala-D-Lys(HSG)-D-Ala-D-Lys(HSG)-NH$_2$ MH$^+$ 1528

IMP 368 Sym-DTPA-D-Ala-D-Lys(HSG)-D-Ala-D-Lys(HSG)-NH$_2$ MH$^+$ 1292

IMP 369 Sym-DTPA-NH—CH(2-Br-Phe-)-CH$_2$—CO-D-Ala-D-Lys(HSG)-D-Ala-D-Lys(HSG)-NH$_2$ MH$^+$ 1517

IMP 370 Sym-DTPA-NH—CH(2-O$_2$N-Phe-)-CH$_2$—CO-D-Ala-D-Lys(HSG)-D-Ala-D-Lys(HSG)-NH$_2$ MH$^+$ 1484

IMP 371 DTPA-NH—CH(2-O$_2$N-Phe-)-CH$_2$—CO-D-Ala-D-Lys(HSG)-D-Ala-D-Lys(HSG)-NH$_2$ MH$^+$ 1484

IMP 372 DTPA-Dpr(Ser)-D-Ala-D-Lys(HSG)-D-Ala-D-Lys(HSG)-NH$_2$MH$^+$ 1465

IMP 373 DTPA-Dpr(Sym-DTPA)-D-Ala-D-Lys(HSG)-D-Ala-D-Lys(HSG)-NH$_2$ MH$^+$ 1753

IMP 374 DTPA-Dpr(Cl—CH2CO-Cys(ET)-)-D-Ala-D-Lys(HSG)-D-Ala-D-Lys(HSG)-NH$_2$ MH$^+$ 1585

IMP 375 DTPA-Dpr(2-Br-Phe-CHNH$_2$—CH$_2$—CO-)-D-Ala-D-Lys(HSG)-D-Ala-D-Lys(HSG)-NH$_2$ MH$^+$ 1603

IMP 376 DTPA-Cys(HO$_3$S—S)-D-Tyr-D-Ala-D-Lys(HSG)-D-Ala-D-Lys(HSG)-NH$_2$ MH$^+$ 1558

IMP 379 DTPA-Dpr(2-H$_2$N-Phe-CO-)-D-Ala-D-Lys(HSG)-D-Ala-D-Lys(HSG)-NH$_2$ MH$^+$ 1497

IMP 382 DTPA-Dpr(H)-D-Ala-D-Lys(HSG)-D-Ala-D-Lys(HSG)-NH$_2$ MH$^+$ 1378

IMP 383 DTPA-Dpr(Gla-)-D-Ala-D-Lys(HSG)-D-Ala-D-Lys(HSG)-NH$_2$MH$^+$ 1507

IMP 384 DTPA-Dpr(2-HO-Phe-CHNH$_2$—CH$_2$—CO-)-D-Ala-D-Lys(HSG)-D-Ala-D-Lys(HSG)-NH$_2$ MH$^+$ 1541

IMP 385 DTPA-Dpr(Dpr)-D-Ala-D-Lys(HSG)-D-Ala-D-Lys(HSG)-NH$_2$ MH$^+$ 1464

IMP 386 DTPA-Dpr(2-pyridyl-CH$_2$—CHNH$_2$—CO-)-D-Ala-D-Lys(HSG)-D-Ala-D-Lys(HSG)-NH$_2$ MH$^+$ 1526

IMP 387 DTPA-Dpr(D-9-anthrylalanine)-D-Ala-D-Lys(HSG)-D-Ala-D-Lys(HSG)-NH$_2$ MH$^+$ 1625

IMP 389 DTPA-Dpr(2-carboxy piperizinyl)-D-Ala-D-Lys(HSG)-D-Ala-D-Lys(HSG)-NH$_2$ MH$^+$ 1490

IMP 422
IMP 422 MH$^+$ 1657

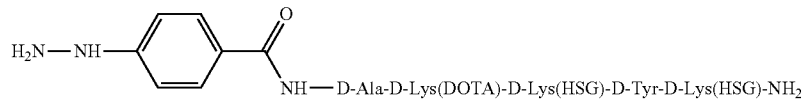

IMP 426
IMP 426 MH$^+$ 1596

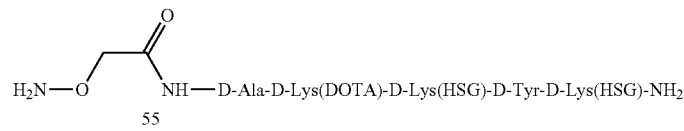

IMP 428
IMP 428 MH$^+$ 1716

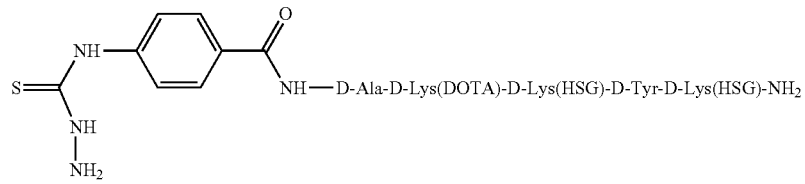

IMP 449 NOTA-ITC benzyl-D-Ala-D-Lys(HSG)-D-Tyr-D-Lys(HSG)-NH$_2$ MH$^+$ 1459

IMP 460 NODA-Ga-D-Ala-D-Lys(HSG)-D-Tyr-D-Lys(HSG)-NH2 MH+ 1366

In an alternative configuration for a NOTA type ligand. The NOTA moiety could be made from D or L para-nitrophenylalanine and the iminodiacetic acid portion would come from diaminopropionic acid, which could be D or L. Furthermore, the position of the ethylene bridge could be switched with the diaminopropionic acid to give a different configuration of groups on the ligand. All of these modifications could affect binding kinetics and stability of the complex, which is subsequently formed. Alternatively, a NODA-Ga peptide could be labeled with, for example, Ga-68 or F-18.

In certain embodiments, alternative chelating moieties may be used to bind to $^{18}$F-metal or $^{18}$F-boron complexes. Some exemplary potential chelating moieties are based on the structure of NETA. As discussed above, Chong et al. (2007) report that NETA ligands may show improved serum stability when complexed with various metals. Chelator design may also be optimized to increase the binding affinity of the peptide for $^{18}$F-metal.

Results of Peptide Labeling Screening Study

Most of the DTPA derivatives showed labeling comparable to the labeling of IMP 272. There were exceptions, IMP 349, bearing the bisphosphonate group on a cysteine side chain, labeled very poorly. The DOTA ligand did not bind the Al—$^{18}$F. The ITC DTPA ligand of IMP 326 did not bind the Al—$^{18}$F as well as DTPA. The NTA ligand of IMP 331 did not bind the Al—$^{18}$F. The EDTA ligand of IMP 332 bound the Al—$^{18}$F but not as well as the DTPA. Symmetrical DTPA ligand did not bind the Al—$^{18}$F. The phosphonates and phosphate groups tested did not bind Al—$^{18}$F well under the conditions tested.

The screen did show that a group that was attached near the DTPA could influence the stability of the Al—$^{18}$F-DTPA complex. The screen showed that IMP 375 labeled better and formed a complex that was significantly more stable than IMP 272. IMP 375 labeled well and was stable in water, showing 95.4% remaining bound after 5 hours at 25° C. (not shown). For in vivo use a peptide with high serum stability would be preferred. The peptide labeling screening study only looked at the binding of Al—$^{18}$F. Some of the peptides that did not label well with Al—$^{18}$F might label better with another metal binding to the F-18.

Peptide Synthesis

The peptides were synthesized by solid phase peptide synthesis using the Fmoc strategy. Groups were added to the side chains of diamino amino acids by using Fmoc/Aloc protecting groups to allow differential deprotection. The Aloc groups were removed by the method of Dangles et. al. (*J. Org. Chem.* 1987, 52:4984-4993) except that piperidine was added in a 1:1 ratio to the acetic acid used. The unsymmetrical tetra-t-butyl DTPA was made as described in McBride et al. (US Patent Application Pub. No. US 2005/0002945 A1, appl. Ser. No. 10/776,470, Pub. Date. Jan. 6, 2005). The tri-t-butyl DOTA, symmetrical tetra-t-butyl DTPA and ITC-benzyl DTPA were obtained from MACROCYCLICS® (Dallas, Tex.). The Aloc/Fmoc Lysine and Dap (diaminopropionic acid derivatives (also Dpr)) were obtained from CREOSALUS® (Louisville, Ky.) or BACHEM® (Torrance, Calif.). The Sieber Amide resin was obtained from NOVABIOCHEM® (San Diego, Calif.). The remaining Fmoc amino acids were obtained from CREOSALUS®, BACHEM®, PEPTECH® (Burlington, Mass.) or NOVABIOCHEM®.

IMP 272 was synthesized as described (McBride et al., US Patent Application Publ. No. 20040241158 A1, appl. Ser. No. 10/768,707, Dec. 2, 2004). IMP 288 was made as described (McBride et al., *J. Nucl. Med.* 2006, 47:1678-1688).

IMP 326 The hydrazine peptide (IMP 319) was made on Sieber amide resin using Fmoc-D-Lys(Aloc)-OH, Fmoc-D-Glu(OBut)-OH, Fmoc-D-Lys(Aloc)-OH, Fmoc-D-Tyr(But)-OH and 4-(Boc-NH—NH—)C$_6$H$_4$—CO$_2$H in that order. The 4-(Boc-NH—NH—)C$_6$H$_4$—CO$_2$H was made by adding Boc dicarbonate to 4-hydrazinobenzoic acid in a dioxane sodium hydroxide solution.

After the addition of the Boc-hydrazide the side chain Aloc groups were removed and the Trityl-HSG-OH groups were added to the side chains of the lysines. The peptide was then cleaved from the resin with TFA and purified by HPLC to obtain the desired hydrazine bis-HSG peptide IMP 319 (MH$^+$ 1201). The hydrazide peptide (0.0914 g) was then mixed with 0.0650 g of ITC-Benzyl DTPA in 3 mL of 0.1 M sodium phosphate pH 8.2. The pH of the solution was adjusted with 1 M NaOH to keep the pH at pH 8.2. After the reaction between the peptide and the ITC-Benzyl DTPA was complete the peptide conjugate was purified by HPLC.

IMP 329 The deferoxamine isothiocyanate was prepared by mixing 1.0422 g of deferoxamine mesylate (1.59×10$^{-3}$ mol) with 0.2835 g (1.59×10$^{-3}$ mol) of thiocarbonyldiimidazole in 10 mL of 1:1 methanol/water. Triethylamine, 0.23 mL was added and the reaction was purified by reverse phase HPLC after 2.5 hr to obtain the deferoxamine isothiocyanate MNa$^+$ 625.

The hydrazine peptide, IMP 319, (0.0533 g, 4.4×10$^{-5}$ mol, MH$^+$ 1201) was mixed with 0.0291 g of deferoxamine isothiocyanate in a sodium phosphate buffer at pH 8.1 for two hours then purified by HPLC to afford the desired product MH+ 1804.

IMP 331 The following amino acids were attached to Sieber amide resin (0.58 mmol/g) in the order shown; Fmoc-D-Lys(Aloc)-OH, Fmoc-D-Tyr(But)-OH and Fmoc-D-Lys(Aloc)-OH. The Aloc groups were removed and Trt-HSG-OH was added to the side chains of the lysines. The Fmoc was removed, then Fmoc-D-Ala-OH and Fmoc-Asp-OBut were added in that order (0.5 g of resin). The Fmoc was removed and the nitrogen of the Asp was alkylated overnight with 3 mL t-butyl bromoacetate and 3.6 mL diisopropylethylamine in 3.4 mL of NMP. The peptide was cleaved from the resin with TFA and purified by reverse phase HPLC to obtain the desired peptide MH$^+$ 1240.

IMP 332 The peptide was made on 3 g of Sieber amide resin (0.58 mmol/g). The following amino acids were added to the resin in the order shown: Fmoc-D-Lys(Aloc)-OH, Fmoc-D-Tyr(But)-OH, Fmoc-D-Lys(Aloc)-OH, Fmoc-D-Ala-OH, and Fmoc-Dpr(Fmoc)-OH. The resin was split into portions for subsequent syntheses. One gram of the resin was removed and the Fmoc groups were removed from the diaminopropionic acid. The peptide was alkylated overnight with 3 mL t-butyl bromoacetate, 3.6 mL diisopropylethyl amine and 3.4 mL NMP. The side chain Aloc groups were then removed and the Trt-HSG-OH groups were added. The peptide was then cleaved from the resin and purified by HPLC to obtain the product MH$^+$ 1327.

IMP 333 The peptide was made with 1 g of the same resin that was used to make IMP 332. The DTPA tetra-t-butyl ester (U.S. Publ. No. 20050002945) was added to both of the amines of the Dpr group. The Aloc groups were then removed and the Trt-HSG-OH was added. The peptide was then cleaved and purified by HPLC to obtain the desired product MH$^+$ 1845.

IMP 334 The peptide was made on 1 g Rink amide resin (0.7 mmol/g) with the following amino acids added in the order shown: Fmoc-D-Lys(Aloc)-OH, Fmoc-D-Glu(But)-

OH, Fmoc-D-Lys(Aloc)-OH, Boc-Ser(But)-OH, The Aloc groups were removed and the Trityl-HSG-OH was added. The peptide was cleaved from the resin with TFA. The crude peptide was collected by precipitation from ether and dried. Sodium periodate, 0.33 g, was dissolved in 15 mL water. The crude peptide was dissolved in 1 mL 0.5 M sodium phosphate pH 7.6, 3 mL water and 1 mL of the periodate solution. 3 mL more periodate in one milliliter increments was added over ~2 hr. The mixture was then purified by reverse phase HPLC and lyophilized to obtain the aldehyde IMP 289 HCO—CO-D-Lys(HSG)-D-Glu-D-Lys(HSG)-NH$_2$MH$^+$ 959. Alendronate (0.0295 g, CALBIOCHEM®) was dissolved in 150 µL 0.1 M NaOAc pH 4. The peptide, IMP 289, (0.0500 g) was dissolved in 100 µL of 13% isopropanol in water. Sodium cyanoborohydride was added and the mixture was purified by HPLC to afford the desired product MH$^+$ 1192.

IMP 337 & IMP 338 The peptide was made on Sieber amide resin using the following amino acids added in the order shown: Fmoc-D-Lys(Aloc)-OH, Fmoc-D-Ala-OH, Fmoc-D-Lys(Aloc)-OH, Fmoc-D-Ala-OH, Fmoc-D-Ser(PO(OBzl)OH)—OH, Fmoc-D-Ser(PO(OBzl)OH)-Fmoc-D-Ser(PO(OBzl)OH—OH, and Ac$_2$O. The Aloc groups were removed and the Trt-HSG-OH groups were added to the side chains of the lysines. The peptide was cleaved from the resin and purified by HPLC to afford the desired products: IMP 337 MH$^+$ 1291 and IMP 338 MH$^+$ 1126.

IMP 345 The peptide was made on Sieber amide resin using the following amino acids added in the order shown: Fmoc-D-Lys(Aloc)-OH, Fmoc-D-Ala-OH, Fmoc-D-Lys(Aloc)-OH, Fmoc-D-Ala-OH, Fmoc-D-Ser(PO(OBzl)OH)—OH, and tetra-t-butyl DTPA. The Aloc groups were removed and the Trt-HSG-OH groups were added to the side chains of the lysines. The peptide was cleaved from the resin and purified by HPLC to afford the desired product: IMP 345 MH$^+$ 1459.

IMP 349 The peptide IMP 347 DTPA-D-Cys-D-Ala-D-Lys(HSG)-D-Tyr-D-Lys(HSG)-NH$_2$ was made on Sieber amide resin using the following amino acids added in the order shown: Aloc-D-Lys(Fmoc)-OH, Trt-HSG-OH, the Aloc was cleaved, Fmoc-D-Ala-OH, Aloc-D-Lys(Fmoc)-OH, Trt-HSG-OH were added, the Aloc was cleaved Fmoc-D-Ala-OH, Fmoc-D-Cys(Trt)-OH and tetra-t-butyl DTPA were added. The peptide was cleaved from the resin and purified by HPLC to afford the desired product: IMP 347 MH$^+$1395. The peptide, IMP 347, 0.0446 g (3.2×10$^{-5}$ mol) was mixed with 0.4605 g (2.4×10$^{-3}$ mol) of ethenylidenebis (phosphonic acid) (Degenhardt et al., *J. Org. Chem.* 1986, 51:3488-3490) in 3 mL of water and the solution was adjusted to pH 6.5 with 1 M NaOH added dropwise. The reaction was stirred overnight and the reaction solution was adjusted to pH 1.49 by the addition of excess ethenylidenebis(phosphonic acid). The mixture was stirred overnight at room temperature and then purified by HPLC to obtain the desired peptide IMP 349 MH$^+$ 1583.

IMP 361 The peptide was made on Sieber amide resin using the following amino acids added in the order shown: Aloc-D-Lys(Fmoc)-OH, Trt-HSG-OH, the Aloc was cleaved, Fmoc-D-Ala-OH, Aloc-D-Lys(Fmoc)-OH, Trt-HSG-OH were added, the Aloc was cleaved, Fmoc-D-Ala-OH, Fmoc-Dap(Aloc)-OH and tetra-t-butyl DTPA were added. The Aloc on the side chain of the Dap was removed and bromo acetyl was added with bromo acetic anhydride. The crude product was purified by HPLC to obtain the desired peptide IMP 361 (MH$^+$ 1498).

IMP 366 The peptide was made by the same method as IMP 361 with phenylthioacetic acid added last. The crude product was purified by HPLC to afford the product IMP 366 MH$^+$ 1528.

IMP 368 The peptide was as described for IMP 349 except the cysteine residue was not added and symmetrical tetra-t-butylDTPA (MACROCYCLICS®) was used in place of the unsymmetrical DTPA to obtain the desired product after purification, IMP 368 MH$^+$ 1292.

IMP 369 The peptide was made as described for IMP 349 with Fmoc-R-3-amino-3-(2-bromophenyl)propionic acid added in place of the D-Cys and symmetrical tetra-t-butylDTPA added in place of the unsymmetrical version to the DTPA tetra-t-butyl ester. The crude peptide was purified to obtain the desired product, MH$^+$ 1517.

IMP 370 The peptide was made as described for IMP 369 except Fmoc-R-3-amino-3-(2-nitrophenyl)propionic acid was used instead of the bromo. The desired product was obtained after purification by HPLC MH$^+$ 1484.

IMP 371 The peptide was made as described for IMP 370 except the unsymmetrical tetra-t-butyl DTPA was used in place of the of the symmetrical version. The desired product was obtained after purification by HPLC MH$^+$ 1484.

IMP 372 The peptide was made as described for IMP 361 with Fmoc-Ser(But)-OH used to attach the Ser to the Dap side chain. The Fmoc was removed and the peptide was cleaved from the resin and purified to obtain the desired product MH$^+$ 1465.

IMP 373 The peptide was made as described for IMP 361 with symmetrical-tetra-t-butylester DTPA used to attach the Sym-DTPA to the Dap side chain. The peptide was cleaved from the resin and purified to obtain the desired product MH$^+$ 1753.

IMP 374 The peptide was made as described for IMP 361 with Fmoc-S-ethyl cysteine added to the Dap side chain followed by chloro acetyl (on the cysteine nitrogen) added via chloroacetic anhydride. The peptide was cleaved from the resin and purified to obtain the desired product MH$^+$ 1585.

IMP 375 The peptide was made as described for IMP 361 with Fmoc-R-3-amino-3-(2-bromophenyl)propionic acid added to the Dap side chain followed by cleavage of the Fmoc group. The peptide was cleaved from the resin and purified to obtain the desired product MH$^+$ 1603.

IMP 376 The peptide was made as described for IMP 361 with Fmoc-D-Tyr(But)-OH added after the second alanine followed by Fmoc-Cys(SO$_3$H) and tetra-t-butylDTPA. The peptide was cleaved from the resin and purified to obtain the desired product MH$^+$ 1558.

IMP 379 The peptide was made as described for IMP 361 with Boc-2-Abz-OH added to the side chain of the Dap. The peptide was cleaved from the resin and purified to obtain the desired product MH$^+$ 1497.

IMP 382 The peptide was made as described for IMP 361 with the Aloc removed from the side chain of the Dap. The peptide was cleaved from the resin and purified to obtain the desired product MH$^+$ 1378.

IMP 383 The peptide was made as described for IMP 361 with Fmoc-Gla(OBut)$_2$-OH added to the side chain of the Dap. The peptide was cleaved from the resin and purified to obtain the desired product MH$^+$—CO$_2$ 1507

IMP 384 The peptide was made as described for IMP 361 with Fmoc-Boc-S-3-amino-3-(2-hydroxyphenyl)propionic acid added to the side chain of the Dap. The peptide was cleaved from the resin and purified to obtain the desired product MH$^+$ 1541.

IMP 385 The peptide was made as described for IMP 361 with Fmoc-Dpr(Fmoc)-OH added to the side chain of the Dap. The peptide was cleaved from the resin and purified to obtain the desired product MH+ 1464.

IMP 386 The peptide was made as described for IMP 361 with Boc-D-2-pyridylalanine-OH added to the side chain of the Dap. The peptide was cleaved from the resin and purified to obtain the desired product MH+ 1526.

IMP 387 The peptide was made as described for IMP 361 with Fmoc-D-9-anthrylalanine-OH added to the side chain of the Dap. The peptide was cleaved from the resin and purified to obtain the desired product MH+ 1625.

IMP 389 The peptide was made as described for IMP 361 with bis-Boc-piperazine-2-carboxylate added to the side chain of the Dap. The peptide was cleaved from the resin and purified to obtain the desired product MH+ 1664.

Example 5

Alternative Methods for Preparing and Separating F-18 Labeled Peptides

In certain embodiments, heating is used to get the Al—F-18 complex into the NOTA chelating group. Alternatively, ITC benzyl NOTA (MACROCYCLICS®) could be labeled with Al—F-18 and then conjugated to other heat sensitive molecules, such as proteins, after labeling. If high specific activity is needed the ITC Benzyl NOTA complex can be purified away from the cold ligand.

Al was added to the peptide and its HPLC profile compared to the empty NOTA peptide and the Al—F-18 peptide. The Al peptide and the Al—F-18 peptides have virtually the same retention time by HPLC, with ~1 min longer RT for the unlabeled peptide. The peptide was purified on a PHENOMENEX™ ONYX® monolithic C-18 100×4.5 mm column using a 3 mL/min flow rate. Buffer A was 0.1% TFA in water and Buffer B was 90% $CH_3CN$ 10% water and 0.1% TFA. The linear gradient went from 100% buffer A to 75:25 A/B over 15 min. Since the Al complex co-elutes with the Al—F-18 complex, the amount of Al and F-18 added will determine the specific activity.

IMP 449 was prepared according to Example 7 below and labeled as follows. The F-18 was received in a 2.0 mL FISHER® microcentrifuge vial (02-681-374) containing 15 mCi of F-18 in ~325 µL in water. 3 µL of 2 mM $AlCl_3$ in 0.1 M pH 4 NaOAc was added to the F-18 solution and then vortex mixed. After about 4 min, 10 µL of 0.05 M IMP 449 in pH 4 0.5 M NaOAc was added. The sample was vortex mixed again and heated in a 102° C. heating block for 17 min. The reaction was then cooled briefly and then the vial contents were removed and purified by HPLC as described above.

Separately, elution conditions were determined on the WATERS® ALLIANCE™ analytical system and the labeled peptide was eluted between 7.5 and 8.5 min. The analytical HPLC showed that the labeled peptide contained the Al—F IMP 449 (UV 220 nm) and did not contain the uncomplexed peptide, resulting in an increased specific activity.

The peptide was diluted in water and then pushed through a WATERS® OASIS PLUS HLB™ extraction column. The labeled peptide was eluted with 3 mL of 1:1 $EtOH/H_2O$. HPLC analysis of the eluents confirmed that the column efficiently trapped the labeled peptide, which allowed the acetonitrile and TFA to be washed away from the peptide. The HPLC also showed that 1:1 $EtOH/H_2O$ eluent contained the desired product free of loose F-18 in a solvent suitable for injection after dilution. The apparent yield after purification was 11%.

Example 6

In-Vivo Studies

Nude mice bearing GW-39 human colonic xenograft tumors (100-500 mg) are injected with the bispecific antibody hMN-14×m679 ($1.5×10^{-10}$ mol). The antibody is allowed to clear for 24 hr before the F-18 labeled HSG-bearing peptide (8.8 µCi, $1.5×10^{-11}$ mol) is injected. The animals are imaged at 3, 24 and 48 hr post injection. The xenograft tumors are clearly imaged by PET scanning detection of the F-18 labeled peptide bound to the bispecific hMN-14×m679 that is localized to the tumors by binding of hMN-14 to tumor antigen.

Example 7

Production and Use of a Serum-Stable F-18 Labeled Peptide

Figure 7:
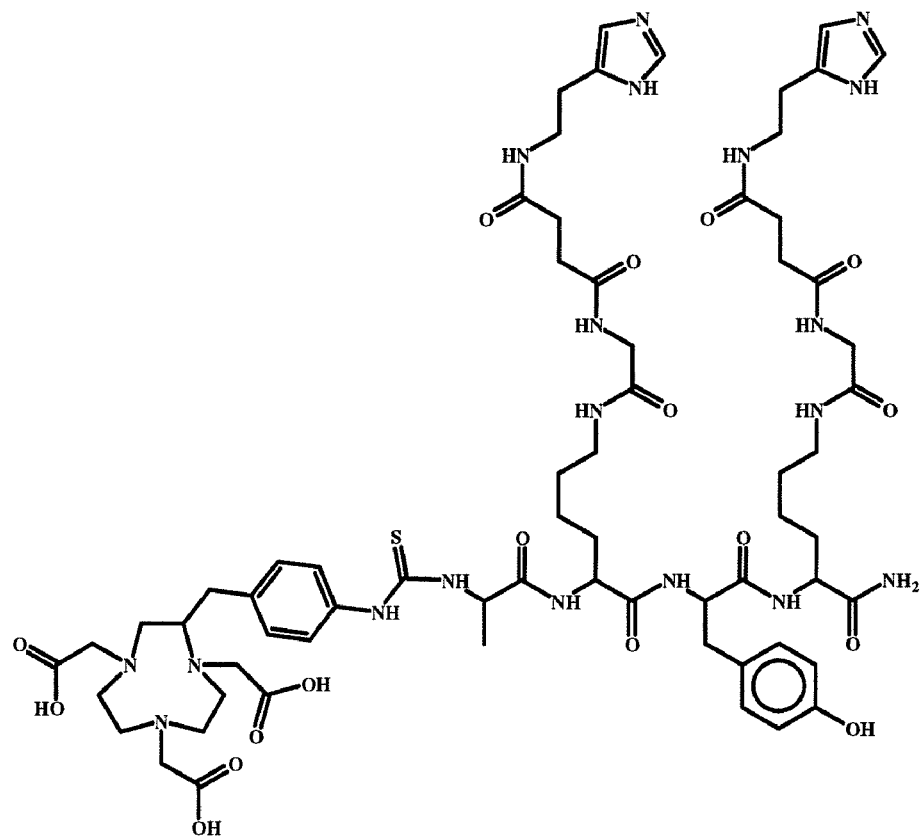
FIG. 7. Structure of IMP 449.

The peptide, IMP 448 D-Ala-D-Lys(HSG)-D-Tyr-D-Lys(HSG)-$NH_2$ MH+ 1009 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloc was cleaved, Fmoc-D-Ala-OH with final Fmoc cleavage to make the desired peptide. The peptide was then cleaved from the resin and purified by HPLC to produce IMP 448, which was then coupled to ITC-benzyl NOTA. The peptide, IMP 448, 0.0757 g ($7.5×10^{-5}$ mol) was mixed with 0.0509 g ($9.09×10^{-5}$ mol) ITC benzyl NOTA and dissolved in 1 mL water. Potassium carbonate anhydrous (0.2171 g) was then slowly added to the stirred peptide/NOTA solution. The reaction solution was pH 10.6 after the addition of all the carbonate. The reaction was allowed to stir at room temperature overnight. The reaction was carefully quenched with 1 M HCl after 14 hr and purified by HPLC to obtain 48 mg of IMP 449, the desired product (FIG. 7).

F-18 Labeling of IMP 449

The peptide IMP 449 (0.002 g, $1.37×10^{-6}$ mol) was dissolved in 686 µL (2 mM peptide solution) 0.1 M NaOAc pH 4.02. Three microliters of a 2 mM solution of Al in a pH 4 acetate buffer was mixed with 15 µL, 1.3 mCi of F-18. The solution was then mixed with 20 µL of the 2 mM IMP 449 solution and heated at 105° C. for 15 min. Reverse Phase HPLC analysis showed 35% (RT ~10 min) of the activity was attached to the peptide and 65% of the activity was eluted at the void volume of the column (3.1 min, not shown) indicating that the majority of activity was not associated with the peptide. The crude labeled mixture (5 µL) was mixed with pooled human serum and incubated at 37° C. An aliquot was removed after 15 min and analyzed by HPLC. The HPLC showed 9.8% of the activity was still attached to the peptide (down from 35%). Another aliquot was removed after 1 hr and analyzed by HPLC. The HPLC showed 7.6% of the activity was still attached to the peptide (down from 35%), which was essentially the same as the 15 min trace (data not shown).

High Dose F-18 Labeling

Further studies with purified IMP 449 demonstrated that the F-18 labeled peptide was highly stable (91%, not shown) in human serum at 37° C. for at least one hour and was partially stable (76%, not shown) in human serum at 37° C. for at least four hours. Additional studies were performed in which the IMP 449 was prepared in the presence of ascorbic acid as a stabilizing agent. In those studies (not shown), the F-18-metal-peptide complex showed no detectable decomposition in serum after 4 hr at 37° C. These results demonstrate that the F-18 labeled peptides disclosed herein exhibit sufficient stability under approximated in vivo conditions to be used for F-18 imaging studies.

For studies in the absence of ascorbic acid, F-18 ~21 mCi in ~400 µL of water was mixed with 9 µL of 2 mM $AlCl_3$ in 0.1 M pH 4 NaOAc. The peptide, IMP 449, 60 µL (0.01 M, $6\times10^{-7}$ mol in 0.5 NaOH pH 4.13) was added and the solution was heated to 110° C. for 15 min. The crude labeled peptide was then purified by placing the reaction solution in the barrel of a 1 cc WATERS® HLB column and eluting with water to remove unbound F-18 followed by 1:1 EtOH/H20 to elute the F-18 labeled peptide. The crude reaction solution was pulled through the column into a waste vial and the column was washed with three one milliliter fractions of water (18.97 mCi). The HLB column was then placed on a new vial and eluted with two×200 µL 1:1 $EtOH/H_2O$ to collect the labeled peptide (1.83 mCi). The column retained 0.1 mCi of activity after all of the elutions were complete. An aliquot of the purified F-18 labeled peptide (20 µL) was mixed with 200 µL of pooled human serum and heated at 37° C. Aliquots were analyzed by reverse phase HPLC (as described above). The results showed the relative stability of F-18 labeled purified IMP 449 at 37° C. at time zero, one hour (91% labeled peptide), two hours (77% labeled peptide) and four hours (76% labeled peptide) of incubation in human serum (not shown). It was also observed that F-18 labeled IMP 449 was stable in TFA solution, which is occasionally used during reverse phase HPLC chromatography. There appears to be a general correlation between stability in TFA and stability in human serum observed for the exemplary F-18 labeled molecules described herein. These results demonstrate that F-18 labeled peptide, produced according to the methods disclosed herein, shows sufficient stability in human serum to be successfully used for in vivo labeling and imaging studies, for example using PET scanning to detect labeled cells or tissues.

Example 8

In Vivo Biodistribution of F-18 Labeled IMP 449 in SCID Mice

F-18 labeled IMP 449 was prepared as described above (Example 7). The material was purified on an OASIS® HLB column (WATERS®, Milford, Mass.). The unbound material was washed out with water and the labeled peptide that was bound to the column was eluted with 1:1 ethanol:water mixture. Both fractions were analyzed by reverse phase C18 HPLC. The purified peptide eluted as several peaks on the reverse HPLC column (not shown). The unbound fraction collected from the OASIS® column showed poor recovery, 7%, from the C18 column (not shown).

The "unbound" fraction and the purified $^{18}$F-IMP 449 were injected into SCID mice that were previously injected with sc SU-DHL6 lymphoma cells. Only a few of the mice had visible tumors. Biodistribution data showed a significant difference between the "unbound" F-18 fraction and the purified $^{18}$F-IMP 449. Data are shown in Tables 4-6 below. Note that in this study, no pretargeting bispecific antibodies were administered to the animals before the labeled peptide. These results demonstrate the distribution of labeled peptide vs. free F-18 in vivo.

Unconjugated F-18 shows a high level of distribution to bone tissue in vivo. Uptake 20 minutes after injection was, as expected, seen primarily in the bone (spine), with about 12-15% injected dose per gram (ID/g), followed by the kidneys with about 4% ID/g. Localization of the F-18 label to bone tissue was substantially decreased by conjugation to a targeting peptide. When bound to IMP 449, uptake in the bone is reduced to ~1% ID/g at 20 min and 0.3% at 1 h after injection, with renal uptake of 11% at 20 min and 3.3% ID/g at 1 hr. Renal uptake of the peptide alone was similar to that of the pretargeted $^{18}$F-IMP 449 peptide (see following Example), suggesting its uptake was a function of the peptide rather than a consequence of the animals having been give the bsMAb 18 h earlier. Relatively low non-specific uptake was observed in the spine and femur with the F-18 labeled peptide compared with unbound F-18.

TABLE 4

F-18 "unbound" fraction at 20 min post injection: % ID/g mean and the individual animals.

| Tissue | n | Mean | SD | Animal 1 | Animal 2 | Animal 3 |
|---|---|---|---|---|---|---|
| Tumor | 1 | — | — | 0.902 | — | — |
| Liver | 3 | 2.056 | 0.244 | 1.895 | 2.338 | 1.937 |
| Spleen | 3 | 1.869 | 0.434 | 1.677 | 2.366 | 1.564 |
| Kidney | 3 | 4.326 | 0.536 | 3.931 | 4.936 | 4.111 |
| Lung | 3 | 2.021 | 0.149 | 1.903 | 2.188 | 1.972 |
| Blood | 3 | 2.421 | 0.248 | 2.355 | 2.696 | 2.212 |
| Stomach | 3 | 0.777 | 0.409 | 0.421 | 1.224 | 0.687 |
| Small Int. | 3 | 2.185 | 0.142 | 2.042 | 2.325 | 2.187 |
| Large Int. | 3 | 1.403 | 0.069 | 1.482 | 1.356 | 1.372 |
| Femur | 3 | 11.688 | 1.519 | 11.502 | 13.292 | 10.270 |
| Spine | 3 | 14.343 | 2.757 | 17.506 | 13.072 | 12.452 |
| Muscle | 3 | 1.375 | 0.160 | 1.191 | 1.457 | 1.478 |

TABLE 5

$^{18}$F-IMP 449 purified, 80 µCi, $1 \times 10^{-8}$ mol at 20 min post injection: % ID/g mean and the individual animals

| Tissue | n | Mean | SD | Animal 1 | Animal 2 | Animal 3 | Animal 4 | Animal 5 |
|---|---|---|---|---|---|---|---|---|
| Tumor | 1 | — | — | 0.891 | — | — | — | — |
| Liver | 5 | 2.050 | 0.312 | 1.672 | 1.801 | 2.211 | 2.129 | 2.440 |
| Spleen | 5 | 1.297 | 0.259 | 0.948 | 1.348 | 1.144 | 1.621 | 1.425 |
| Kidney | 5 | 12.120 | 4.128 | 8.354 | 7.518 | 12.492 | 15.535 | 16.702 |
| Lung | 5 | 2.580 | 0.518 | 2.034 | 2.103 | 2.804 | 2.678 | 3.278 |
| Blood | 5 | 3.230 | 0.638 | 2.608 | 2.524 | 3.516 | 3.512 | 3.992 |
| Stomach | 5 | 1.017 | 0.907 | 0.805 | 0.775 | 0.344 | 0.557 | 2.605 |
| Small Int. | 5 | 1.212 | 0.636 | 0.896 | 0.921 | 0.927 | 0.967 | 2.349 |
| Large Int. | 5 | 0.709 | 0.220 | 0.526 | 0.568 | 0.599 | 0.793 | 1.057 |
| Femur | 5 | 0.804 | 0.389 | 0.314 | 0.560 | 1.280 | 0.776 | 1.087 |
| Spine | 5 | 3.915 | 6.384 | 0.819 | 0.923 | 1.325 | 1.177 | 15.330[#] |
| Muscle | 5 | 0.668 | 0.226 | 0.457 | 0.439 | 0.960 | 0.673 | 0.814 |

[#]High spine uptake in Animal #5 was confirmed by recounting.

TABLE 6

$^{18}$F-IMP 449 purified, 80 µCi, 1 × 10$^{-8}$ mol at 1 h post injection: % ID/g mean and the individual animals

| Tissue | n | Mean | SD | Animal 1 | Animal 2 | Animal 3 | Animal 4 |
|---|---|---|---|---|---|---|---|
| Tumor | 1 | 0.032 | 0.064 | 0.000 | 0.127 | 0.000 | 0.000 |
| Liver | 4 | 0.883 | 0.308 | 1.103 | 0.632 | 0.604 | 1.191 |
| Spleen | 4 | 1.061 | 0.702 | 1.598 | 0.631 | 0.301 | 1.713 |
| Kidney | 4 | 3.256 | 0.591 | 3.606 | 2.392 | 3.362 | 3.666 |
| Lung | 4 | 0.324 | 0.094 | 0.411 | 0.232 | 0.256 | 0.399 |
| Blood | 4 | 0.285 | 0.104 | 0.378 | 0.153 | 0.250 | 0.358 |
| Stomach | 4 | 0.152 | 0.082 | 0.225 | 0.041 | 0.199 | 0.142 |
| Small Int. | 4 | 1.290 | 0.228 | 1.124 | 1.247 | 1.166 | 1.624 |
| Large Int. | 4 | 0.115 | 0.035 | 0.167 | 0.091 | 0.094 | 0.109 |
| Femur | 4 | 1.006 | 0.876 | 2.266 | 0.448 | 0.939 | 0.374 |
| Spine | 4 | 0.314 | 0.076 | 0.423 | 0.257 | 0.268 | 0.306 |
| Muscle | 4 | 0.591 | 0.946 | 0.205 | 0.077 | 2.008 | 0.075 |

We conclude that the F-18 labeled peptide showed sufficient in vivo stability to successfully perform labeling and imaging studies.

Example 9

Preparation of DNL Constructs for F-18 Imaging by Pretargeting

In various forms, the DNL technique may be used to make dimers, trimers, tetramers, hexamers, etc. comprising virtually any antibodies or fragments thereof or other effector moieties. For certain preferred embodiments, IgG antibodies or Fab antibody fragments may be produced as fusion proteins containing either a DDD or AD sequence. Bispecific antibodies may be formed by combining a Fab-DDD fusion protein of a first antibody with a Fab-AD fusion protein of a second antibody. Alternatively, constructs may be made that combine IgG-AD fusion proteins with Fab-DDD fusion proteins. For purposes of F-18 detection, an antibody or fragment containing a binding site for an antigen associated with a target tissue to be imaged, such as a tumor, may be combined with a second antibody or fragment that binds a hapten on a targetable construct, such as IMP 449, to which an F-18 metal group may be attached. The bispecific antibody (DNL construct) is administered to a subject, circulating antibody is allowed to clear from the blood and localize to target tissue, and the F-18 labeled targetable construct is added and binds to the localized antibody for imaging.

Independent transgenic cell lines may be developed for each Fab or IgG fusion protein. Once produced, the modules can be purified if desired or maintained in the cell culture supernatant fluid. Following production, any DDD$_2$-fusion protein module can be combined with any AD-fusion protein module to generate a bispecific DNL construct. For different types of constructs, different AD or DDD sequences may be utilized.

DDD1:
(SEQ ID NO: 3)
SHIQIPPGTELLQGYTVEVLRQQPPDLVEFAVEYFTRLREARA

DDD2:
(SEQ ID NO: 4)
CGHIQIPPGLTELLQGYTVEVLRQQPPDLVEFAVEYFTRLREARA

AD1:
(SEQ ID NO: 5)
QIEYLAKQIVDNAIQQA

AD2:
(SEQ ID NO: 6)
CGQIEYLAKQIVDNAIQQAGC

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC (SEQ ID:11)) followed by four glycines and a serine (SEQ ID NO:12), with the final two codons (GS) comprising a Bam HI restriction site. The 410 bp PCR amplimer was cloned into the pGemT PCR cloning vector (Promega, Inc.) and clones were screened for inserts in the T7 (5') orientation.

Construction of (G$_4$S)$_2$ (SEQ ID:13) DDD1

A duplex oligonucleotide, designated (G$_4$S)$_2$ (SEQ ID:13) DDD1, was synthesized by Sigma Genosys (Haverhill, UK) to code for the amino acid sequence of DDD1 preceded by 11 residues of the linker peptide, with the first two codons comprising a BamHI restriction site. A stop codon and an EagI restriction site are appended to the 3'end. The encoded polypeptide sequence is shown below.

GSGGGGSGGGGSHIQIPPGLTELLQGYTVEVLRQQPPDLVEFAVEYFTRLREARA (SEQ ID NO: 7)

Two oligonucleotides, designated RIIA1-44 top and RIIA1-44 bottom, that overlap by 30 base pairs on their 3' ends, were synthesized (Sigma Genosys) and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into pGemT and screened for inserts in the T7 (5') orientation.

Construction of $(G_4S)_2$ (SEQ ID:13)-AD1

A duplex oligonucleotide, designated $(G_4S)_2$ (SEQ ID:13)-AD1, was synthesized (Sigma Genosys) to code for the amino acid sequence of AD1 preceded by 11 residues of the linker peptide with the first two codons comprising a BamHI restriction site. A stop codon and an EagI restriction site are appended to the 3'end. The encoded polypeptide sequence is shown below.

GSGGGGSGGGGSQIEYLAKQIVDNAIQQA      (SEQ ID NO: 8)

Two complimentary overlapping oligonucleotides encoding the above peptide sequence, designated AKAP-IS Top and AKAP-IS Bottom, were synthesized and annealed. The duplex was amplified by PCR. The amplimer was cloned into the pGemT vector and screened for inserts in the T7 (5') orientation.

Ligating DDD1 with CH1

A 190 bp fragment encoding the DDD1 sequence was excised from pGemT with BamHI and NotI restriction enzymes and then ligated into the same sites in CH1-pGemT to generate the shuttle vector CH1-DDD1-pGemT.

Ligating AD1 with CH1

A 110 bp fragment containing the AD1 sequence was excised from pGemT with BamHI and NotI and then ligated into the same sites in CH1-pGemT to generate the shuttle vector CH1-AD1-pGemT.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide (GGGGSGGGCG, SEQ ID NO:9) and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-pGemT, which was prepared by digestion with BamHI and PstI, to generate the shuttle vector CH1-DDD2-pGemT. A 507 bp fragment was excised from CH1-DDD2-pGemT with SacII and EagI and ligated with the IgG expression vector hMN14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

H679-Fd-AD2-pdHL2 h679-Fab-AD2, was designed to pair as B to C-DDD2-Fab-hMN-14 as A. h679-Fd-AD2-pdHL2 is an expression vector for the production of h679-Fab-AD2, which possesses an anchor domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-pGemT, which was prepared by digestion with BamHI and SpeI, to generate the shuttle vector CH1-AD2-pGemT. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Generation of TF2

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP-291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP-291 affinity chromatography (not shown). SE-HPLC analysis of the IMP-291 unbound fraction demonstrated the removal of $a_4$, $a_2$ and free kappa chains from the product (not shown).

Non-reducing SDS-PAGE analysis demonstrated that the majority of TF2 exists as a large, covalent structure with a relative mobility near that of IgG (not shown). The additional bands suggest that disulfide formation is incomplete under the experimental conditions (not shown). Reducing SDS-PAGE shows that any additional bands apparent in the non-reducing gel are product-related (not shown), as only bands representing the constituent polypeptides of TF2 are evident. However, the relative mobilities of each of the four polypeptides are too close to be resolved. MALDI-TOF mass spectrometry (not shown) revealed a single peak of 156,434 Da, which is within 99.5% of the calculated mass (157,319 Da) of TF2.

The functionality of TF2 was determined by BIACORE assay. TF2, C-DDD1-hMN-14+h679-AD1 (used as a control sample of noncovalent $a_2b$ complex), or C-DDD2-hMN-14+h679-AD2 (used as a control sample of unreduced $a_2$ and b components) were diluted to 1 μg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

A similar protocol was used to generate a trimeric TF10 DNL construct, comprising two copies of a C-DDD2-Fab-hPAM4 and one copy of C-AD2-Fab-679. TF2 and TF10 were used in imaging studies with F-18 labeled targetable construct, as described below.

Example 10

In Vivo Studies With Pretargeting Antibody

F-18 labeled IMP 449 was prepared as follows. The F-18, 54.7 mCi in ~0.5 mL was mixed with 3 μL 2 mM Al in 0.1 M NaOAc pH 4 buffer. After 3 min, 10 μL of 0.05 M IMP 449 in 0.5 M pH 4 NaOAc buffer was added and the reaction was heated in a 96° C. heating block for 15 min. The contents of the reaction were removed with a syringe. The crude labeled peptide was then purified by HPLC on a C18 column. The flow rate was 3 mL/min. Buffer A was 0.1% TFA in water and Buffer B was 90% acetonitrile in water with 0.1% TFA. The gradient went from 100% A to 75/25 A:B over 15 min. There was about 1 min difference in RT between the labeled peptide, which eluted first and the unlabeled peptide. The HPLC eluent was collected in 0.5 min fractions. The labeled peptide came out between 6 to 9 min depending on the HPLC used. The HPLC purified peptide sample was further processed by diluting the fractions of interest two fold in water and placing the solution in the barrel of a 1 cc WATERS® HLB column. The cartridge was eluted with 3×1 mL water to remove acetonitrile and TFA followed by 400 μL 1:1 EtOH/H20 to elute the F-18 labeled peptide. The purified $^{18}$F-IMP 449 eluted as a single peak on an analytical HPLC C18 column (not shown).

Taconic nude mice bearing the four slow-growing sc CaPan1 xenografts were used for in vivo studies. Three of the mice were injected with TF10 (162 μg) followed with $^{18}$F-IMP 449 18 h later. TF10 is a humanized bispecific antibody of use for tumor imaging studies, with divalent binding to the PAM-4 defined tumor antigen and monovalent binding to HSG (see, e.g., Gold et al., 2007, J. Clin. Oncol. 25(18S): 4564). One mouse was injected with peptide alone. All of the mice were necropsied at 1 h post peptide injection. Tissues were counted immediately. Animal #2 showed high counts in the femur. The femur was transferred into a new vial and was recounted along with the old empty vial. Recounting indicated that the counts were on the tissue. This femur was broken and had a large piece of muscle attached to it. Comparison of mean distributions showed substantially higher levels of F-18-labeled peptide localized in the tumor than in any normal tissues in the presence of tumor-targeting bispecific antibody.

Tissue uptake was similar in animals given the $^{18}$F-IMP 449 alone or in a pretargeting setting. Uptake in the human pancreatic cancer xenograft, CaPan1, at 1 h was increased 5-fold in the pretargeted animals as compared to the peptide alone (4.6±0.9% ID/g vs. 0.89% ID/g). Exceptional tumor/nontumor ratios were achieved at this time (e.g., tumor/blood and liver ratios were 23.4±2.0 and 23.5±2.8, respectively).

TABLE 7

Tissue uptake at 1 h post peptide injection, mean and the individual animals:

| | | | | TF10 (162 μg)-→18 h → $^{18}$F IMP449 (10:1) | | | $^{18}$F IMP 449 alone |
|---|---|---|---|---|---|---|---|
| Tissue | n | Mean | SD | Animal 1 | Animal 2 | Animal 3 | Animal 1 |
| Tumor (mass) | 3 | 4.591 | 0.854 | 4.330 (0.675 g) | 5.546 (0.306 g) | 3.898 (0.353 g) | 0.893 (0.721 g) |
| Liver | 3 | 0.197 | 0.041 | 0.163 | 0.242 | 0.186 | 0.253 |
| Spleen | 3 | 0.202 | 0.022 | 0.180 | 0.224 | 0.200 | 0.226 |
| Kidney | 3 | 5.624 | 0.531 | 5.513 | 6.202 | 5.158 | 5.744 |
| Lung | 3 | 0.421 | 0.197 | 0.352 | 0.643 | 0.268 | 0.474 |
| Blood | 3 | 0.196 | 0.028 | 0.204 | 0.219 | 0.165 | 0.360 |
| Stomach | 3 | 0.123 | 0.046 | 0.080 | 0.172 | 0.118 | 0.329 |
| Small Int. | 3 | 0.248 | 0.042 | 0.218 | 0.295 | 0.230 | 0.392 |
| Large Int. | 3 | 0.141 | 0.094 | 0.065 | 0.247 | 0.112 | 0.113 |
| Pancreas | 3 | 0.185 | 0.078 | 0.259 | 0.194 | 0.103 | 0.174 |
| Spine | 3 | 0.394 | 0.427 | 0.140 | 0.888 | 0.155 | 0.239 |
| Femur | 3 | 3.899 | 4.098 | 2.577 | 8.494* | 0.625 | 0.237 |
| Brain | 3 | 0.064 | 0.041 | 0.020 | 0.072 | 0.100 | 0.075 |
| Muscle | 3 | 0.696 | 0.761 | 0.077 | 1.545 | 0.465 | 0.162 |

*High counts in Animal # 2 femur were confirmed by recounting after transferring femur into a new vial. Animal # 2 showed higher uptake in normal tissues than Animals #1 and #3.

Example 11

Comparison of Biodistribution of $^{111}$In-IMP 449 vs. $^{18}$F-IMP 449 with Pretargeting Antibody The goal of the study was to compare biodistribution of $^{111}$In-IMP 449 and $^{18}$F-IMP 449 in nude mice bearing sc LS174 T xenografts after pretargeting with bispecific antibody TF2. TF2 antibody was made by the dock-and-lock method and contains binding sites for the CEA tumor antigen and the HSG hapten (see, e.g., Sharkey et al., Radiology 2008, 246:497-507; Rossi et al., PNAS USA 2006, 103:6841-46). Since there were insufficient numbers of mice with tumors at one time, the study was performed during 2 different weeks.

$^{111}$In-IMP 449: $^{111}$In labeling was performed using a procedure similar to the one used for labeling IMP 288, except at lower specific activity. ITLC and C-18 RP HPLC showed ~30% unbound (not shown). The labeled peptide was purified on an HLB column (1 mL, 30 mg). The analyses of the purified product again showed 33% unbound by ITLC developed in saturated sodium chloride (not shown). RP HPLC showed multiple peaks before and after purification (not shown). SE HPLC after purification showed 47% of the activity shift to high MW when mixed with 20× molar excess of TF2 (not shown).

$^{18}$F-IMP 449: Labeling was performed as described above except the F-18 was purified on a QMA cartridge before labeling as described by Kim et. al. (Applied Radiation and Isotopes 61, 2004, 1241-46). Briefly, the SEP-PAK® LIGHT WATERS ACCELL™ Plus QMA Cartridge was prepared flushed with 10 mL 0.4 M KHCO$_3$ and then washed with 10 mL DI water. The $^{18}$F (42 mCi) in 2 mL water was loaded onto the QMA cartridge. The cartridge was eluted with 10 mL DI water to remove impurities. The column was then eluted with 1 mL 0.4 M KHCO$_3$ in 200 µL fractions. Fraction number two contained the bulk of the activity, 33 mCi. The pH of the F-18 solution was then adjusted with 10 µL of glacial acetic acid. The $^{18}$F from fraction #2 was then mixed with 3 µL of 2 mM Al in 0.1 M pH 4 NaOAc buffer. The sample was then mixed with 10 µL of 0.05 M IMP 449 in 0.5 M NaOAc buffer at pH4 and the reaction solution was heated at 94° C. for 15 min. The $^{18}$F-IMP 449 was purified by RP HPLC. The fraction containing the product was put through an HLB column to exchange the buffer. The column was washed with water after loading the sample. The product was eluted with 1:1 water: ethanol in a 400 µL volume. RP HPLC of the product showed one major peak with a shoulder (not shown). Since the yield was low, the specific activity was low and more peptide was injected into mice, resulting in a bsMAb:peptide ratio of 6.9:1 instead of 10:1.

Results

The labeling of IMP 449 with In-111 resulted in multiple products. Possibly some might be binuclear complexes. The $^{111}$In-IMP 449 showed high kidney uptake and high blood concentration. However, even as multiple species, $^{111}$In-IMP 449 showed localization to the tumor when pretargeted with TF2 (FIG. 1).

FIG. 1 shows the comparative biodistribution of In-111 and F-18 labeled IMP 449 in mice. Both labeled peptides showed similarly high levels of localization to tumor tissues in the presence of the bispecific TF2 antibody. The In-111 labeled species showed higher concentration in kidney than the F-18 labeled species in the presence or absence of TF2 antibody. The data are summarized in Tables 8-11 below.

TABLE 8

Mice were injected with TF2 (163.2ug, $1.035 \times 10^{-9}$ mol) iv followed with $^{111}$In IMP 449 ($1.035 \times 10^{-10}$ mol) 16 h later. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 9.18 | 1.02 | 9.22 | 8.47 | 8.04 | 9.45 | 10.70 |
| Liver | 5 | 1.15 | 0.09 | 1.03 | 1.25 | 1.20 | 1.21 | 1.08 |
| Spleen | 5 | 0.48 | 0.06 | 0.43 | 0.49 | 0.58 | 0.50 | 0.42 |
| Kidney | 5 | 6.63 | 1.38 | 8.81 | 6.21 | 7.03 | 5.85 | 5.23 |
| Lung | 5 | 1.03 | 0.14 | 0.92 | 1.14 | 1.18 | 1.04 | 0.86 |
| Blood | 5 | 0.99 | 0.15 | 1.04 | 1.13 | 1.12 | 0.83 | 0.83 |
| Stomach | 5 | 0.16 | 0.05 | 0.25 | 0.17 | 0.16 | 0.13 | 0.12 |
| Small Int. | 5 | 2.33 | 0.65 | 2.21 | 2.51 | 2.01 | 3.33 | 1.59 |
| Large Int. | 5 | 0.20 | 0.04 | 0.21 | 0.25 | 0.18 | 0.21 | 0.14 |
| Femur | 5 | 1.45 | 0.87 | 0.59 | 1.30 | 0.71 | 2.02 | 2.62 |
| Spine | 5 | 1.18 | 1.23 | 0.89 | 3.35 | 0.76 | 0.47 | 0.43 |
| Brain | 5 | 0.14 | 0.16 | 0.05 | 0.06 | 0.13 | 0.04 | 0.43 |
| Muscle | 5 | 0.83 | 0.66 | 0.25 | 1.30 | 0.23 | 0.65 | 1.73 |
| Body Wt. | 5 | 25.49 | 1.41 | 27.89 | 24.14 | 25.27 | 25.10 | 25.06 |

TABLE 9

A group of 2 mice were injected with $^{111}$In IMP 449 ($1.035 \times 10^{-10}$ mol) without pretargeting antibody. Peptide tissue uptake (% ID/g) at 1 h post peptide injection is shown below.

| Tissue | n | Mean | SD | Animal 1 | Animal 2 |
|---|---|---|---|---|---|
| Tumor | 2 | 0.922 | 0.195 | 0.784 | 1.060 |
| Liver | 2 | 1.033 | 0.048 | 0.999 | 1.067 |
| Spleen | 2 | 0.409 | 0.067 | 0.362 | 0.456 |
| Kidney | 2 | 6.046 | 0.449 | 5.729 | 6.364 |
| Lung | 2 | 0.695 | 0.032 | 0.672 | 0.717 |
| Blood | 2 | 0.805 | 0.182 | 0.934 | 0.676 |
| Stomach | 2 | 0.290 | 0.055 | 0.251 | 0.329 |
| Small Int. | 2 | 2.234 | 0.594 | 1.814 | 2.654 |
| Large Int. | 2 | 0.237 | 0.022 | 0.253 | 0.222 |
| Femur | 2 | 1.210 | 1.072 | 1.968 | 0.453 |
| Spine | 2 | 1.463 | 1.213 | 2.320 | 0.605 |
| Brain | 2 | 0.133 | 0.091 | 0.068 | 0.197 |
| Muscle | 2 | 1.005 | 1.148 | 1.817 | 0.193 |
| Body Wt. | 2 | 26.65 | 3.19 | 28.90 | 24.39 |

TABLE 10

Mice were injected with TF2 (163.2ug, $1.035 \times 10^{-9}$ mol) iv followed with $^{18}$F-IMP 449 ($1.5 \times 10^{-10}$ mol) 16 h later. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 7.624 | 3.080 | 5.298 | 7.848 | 12.719 | 5.118 | 7.136 |
| Liver | 5 | 0.172 | 0.033 | 0.208 | 0.143 | 0.196 | 0.131 | 0.180 |
| Spleen | 5 | 0.142 | 0.059 | 0.239 | 0.081 | 0.132 | 0.118 | 0.140 |
| Kidney | 5 | 2.191 | 0.125 | 2.313 | 2.141 | 2.154 | 2.319 | 2.027 |
| Lung | 5 | 0.315 | 0.094 | 0.474 | 0.230 | 0.300 | 0.305 | 0.265 |
| Blood | 5 | 0.269 | 0.143 | 0.431 | 0.395 | 0.132 | 0.126 | 0.260 |
| Stomach | 5 | 0.218 | 0.341 | 0.827 | 0.041 | 0.098 | 0.054 | 0.070 |
| Small Int. | 5 | 0.351 | 0.313 | 0.903 | 0.185 | 0.297 | 0.170 | 0.198 |
| Large Int. | 5 | 0.069 | 0.028 | 0.076 | 0.043 | 0.111 | 0.073 | 0.042 |
| Femur | 5 | 0.625 | 0.358 | 0.869 | 0.146 | 0.811 | 0.957 | 0.344 |
| Spine | 5 | 0.585 | 0.569 | 0.159 | 0.119 | 0.493 | 1.526 | 0.626 |
| Brain | 5 | 0.029 | 0.005 | 0.033 | 0.021 | 0.035 | 0.026 | 0.028 |
| Muscle | 5 | 0.736 | 0.970 | 0.190 | 0.064 | 0.494 | 2.438 | 0.496 |
| Body Wt. | 5 | 24.69 | 1.20 | 23.05 | 26.36 | 24.45 | 24.48 | 25.11 |

TABLE 11

Mice were injected with $^{18}$F-IMP 449 ($1.5 \times 10^{-10}$ mol) without pretargeting antibody. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 0.472 | 0.201 | 0.256 | 0.344 | 0.533 | 0.447 | 0.779 |
| Liver | 5 | 0.177 | 0.035 | 0.141 | 0.200 | 0.141 | 0.185 | 0.217 |
| Spleen | 5 | 0.118 | 0.027 | 0.098 | 0.094 | 0.101 | 0.144 | 0.151 |
| Kidney | 5 | 2.727 | 0.367 | 2.430 | 2.452 | 2.500 | 3.080 | 3.173 |
| Lung | 5 | 0.246 | 0.082 | 0.206 | 0.209 | 0.156 | 0.301 | 0.358 |
| Blood | 5 | 0.167 | 0.072 | 0.110 | 0.135 | 0.104 | 0.217 | 0.267 |
| Stomach | 5 | 0.114 | 0.083 | 0.149 | 0.241 | 0.037 | 0.067 | 0.074 |
| Small Int. | 5 | 0.277 | 0.081 | 0.407 | 0.286 | 0.206 | 0.213 | 0.271 |
| Large Int. | 5 | 0.072 | 0.029 | 0.061 | 0.052 | 0.047 | 0.083 | 0.118 |
| Femur | 5 | 0.100 | 0.032 | 0.080 | 0.144 | 0.110 | 0.109 | 0.059 |
| Spine | 5 | 0.305 | 0.268 | 0.104 | 0.647 | 0.099 | 0.132 | 0.545 |
| Brain | 5 | 0.034 | 0.025 | 0.018 | 0.018 | 0.022 | 0.034 | 0.077 |
| Muscle | 5 | 0.088 | 0.022 | 0.087 | 0.069 | 0.069 | 0.122 | 0.092 |
| Body Wt. | 5 | 25.34 | 1.72 | 25.05 | 26.88 | 26.40 | 25.88 | 22.51 |

A simple, reproducible method and compositions are described herein for producing F-18 labeled targeting peptides that are suitable for use in in vivo imaging of a variety of disease states. The skilled artisan will realize that the bispecific antibodies disclosed above are not limiting, but may comprise any known antibodies against a wide variety of disease or pathogen target antigens. Nor is the method limited to pretargeting with bispecific antibodies. In other embodiments, molecules or complexes that directly bind to target cells, tissues or organisms to be imaged may be labeled with F-18 using the methods disclosed herein and administered to a subject for PET imaging (see Examples below).

The Al—F-18 labeled peptides, exemplified by IMP 449, are sufficiently stable under in vivo conditions to be utilized in known imaging protocols, such as PET scanning The present yield of radiolabeled peptide prepared as described above varies between 5 and 20%, and even with a brief HPLC purification step to separate labeled from unlabeled peptide the final yield is about 5%. Further, the claimed methods result in preparation of F-18 labeled targeting peptides that are ready for injection within 1 hour of preparation time, well within the decay time of F-18 to allow suitable imaging procedures to be performed. Finally, the described and claimed methods result in minimal exposure of the operator to radioisotope exposure, compared with known methods of preparing F-18 labeled compounds for imaging studies.

Example 12

F-18 Labeling Kit

An F-18 labeling kit was made by mixing 8.0 mg of IMP 449 with 0.1549 g of ascorbic acid. The two reagents were dissolved in 10.5 mL water and the solution was dispensed in 1.0 mL aliquots into 10 vials. The pH was not adjusted. The solutions were frozen, lyophilized and sealed under vacuum.

Example 13

Imaging of Tumors Using Labeled Peptides and Pretargeting with Bispecific Antibodies In vivo imaging techniques using pretargeting with bispecific antibodies and labeled targeting peptides may be used to successfully detect tumors of relatively small size. The pretargeting antibodies utilized were either TF2, described above, or the TF10 antibody.

Formulation Buffer:

The formulation buffer was made by mixing 0.3023 g ascorbic acid, 18.4 mL DI water and 1.6 mL 1 M NaOH to adjust the pH to 6.61. The buffer was dispensed in 1 mL aliquots into 20 vials and lyophilized.

The F-18 was purified on a WATERS® ACCELL™ Plus QMA Light cartridge according to the literature procedure, wherein the cartridge was washed with 10 mL 0.4 M KHCO$_3$ followed by a 10 mL wash with DI water. The F-18 in 2 mL of water was pushed through the cartridge and then washed with 10 mL of water. The F-18 was then eluted from the cartridge in 5×200 μL aliquots with 0.4 M KHCO$_3$. Most of the activity was eluted in the second fraction. The activity in the second fraction was mixed with 3 μL 2 mM Al in a pH 4 acetate buffer. The Al—F-18 solution was then injected into the ascorbic acid IMP 449 labeling vial and heated to 105° C. for 15 min. The reaction solution was cooled and mixed with 0.8 mL DI water. The reaction contents were placed on a WATERS® OASIS® 1 cc HLB Column and eluted into a waste vial. The column was washed with 3×1 mL DI water. The column was transferred to a formulation vial containing ascorbic acid. The column was eluted with 2×200 μL 1:1 EtOH/H$_2$O to elute the labeled peptide.

Production of TF10 Bispecific Antibody Using DNL Technology

The cancer-targeting antibody component in TF10 is derived from hPAM4, a humanized anti-pancreatic cancer mucin MAb that has been studied in detail as a radiolabeled MAb (e.g., Gold et al., *Clin. Cancer Res.* 13: 7380-7387, 2007). The hapten-binding component is derived from h679, a humanized anti-histaminyl-succinyl-glycine (HSG) MAb discussed above. The TF10 bispecific ([hPAM4]$_2$×h679) antibody was produced using the method disclosed for production of the (anti CEA)$_2$×anti HSG bsAb TF2 (Rossi et al., 2006, see also Example 9 above). The TF10 construct bears two humanized PAM4 Fabs and one humanized 679 Fab.

The two fusion proteins (hPAM4-DDD and h679-AD2) were expressed independently in stably transfected myeloma cells. The tissue culture supernatant fluids were combined, resulting in a two-fold molar excess of hPAM4-DDD. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP 291-affigel resin, which binds with high specificity to the h679 Fab.

A full tissue histology and blood cell binding panel has already been examined for hPAM4 IgG and for an anti-CEA× anti-HSG bsMAb that is entering clinical trials. hPAM4 binding was restricted to very weak binding to the urinary bladder and stomach in 1/3 specimens (no binding was seen in vivo), and no binding to normal tissues was attributed to the anti-CEA× anti-HSG bsMAb. Furthermore, in vitro studies against cell lines bearing the H1 and H2 histamine receptors showed no antagonistic or agonistic activity with the IMP-288 di-HSG peptide, and animal studies in 2 different species showed no pharmacologic activity of the peptide related to the histamine component at doses 20,000 times higher than that used for imaging. Thus, the HSG-histamine derivative does not have pharmacologic activity.

Biodistribution, Targeting and Dosage Studies of TF10 Bispecific Antibody

The biodistribution and tumor targeting of TF10 with increasing TF10 doses is determined. These studies provide basic Pk data for TF10 over a range of doses. The primary dose range simulates human equivalent doses (HED) between 1.0 to 50 mg given to a 70 kg patient. Based on FDA guidelines for converting a dose given to an animal to a HED [i.e., (mg/kg in a mouse/12.3)=mg/kg HED], a 1 mg (6.37 nmol) TF10 dose given to a 70 kg human would be equivalent to a 3.5 μg (0.022 nmol) dose in a 20 g mouse.

Briefly, animals are given iv injections of 3.5, 17.5, 35, and 70 TF10 (trace $^{125}$I-TF10 added). Animals given 17.5, 35, and 70 μg doses (HED=1, 5, 10 and 20 mg) are necropsied at 1, 6, 16, 48, and 72 h (n=5 per observation; total N=75 animals/cell line). Studies with the current lot of TF10 have indicated a very rapid clearance in mice, similar to that of the TF2 anti-CEA construct described above.

Pk studies are also performed with $^{131}$I-TF10 in rabbits. Prior studies with TF2 anti-CEA bsMAb have indicated that rabbits might better predict the Pk behavior that is observed in patients, since they clear humanized anti-CEA IgG in an identical manner as that found in patients, while mice clear humanized IgG at a faster rate. These studies involve 4 rabbits, 2 given a 5-mg HED and 2 given a 20-mg HED of TF10 spiked with $^{131}$I-TF10 (~700 μCi). Rabbits are bled at 5 min, 1, 3, 6, 24, 48, 72, 96, 120, and 168 h. Whole-body images are also taken using a gamma camera equipped with a high-energy collimator. An $^{131}$I-standard (~20 μCi in a 10 mL syringe) is placed in the field of view with each rabbit during each imaging session taken at 3, 24, 48, 120, and 168 h. The standard is then used to provide semi-quantitative data on the distribution of $^{131}$I-TF10.

Example 14

In Vivo Imaging Using F-18 Labeled Peptides and Comparison with $^{18}$FDG

Methods

The recombinant, humanized, tri-Fab bsMAB, TF2, was prepared by the Dock-and-Lock method (see Example 9 above), and binds divalently to carcinoembryonic antigen (CEA) and monovalently to the synthetic hapten, HSG (histamine-succinyl-glycine). The bsMAb was >95% immunoreactive against CEA and the divalent-HSG NOTA-peptide IMP 449 using a size-exclusion HPLC method (not shown).

Biodistribution and microPET imaging. Six-week-old NCr nu-m female nude mice were implanted s.c. with the human colonic cancer cell line, LS174T (ATCC, Manassas, Va.). When tumors were visibly established, pretargeted animals were injected intravenously with 162 μg (~1 nmole/0.1 mL) TF2 or TF10 (control non-targeting tri-Fab bsMAB), and then 16-18 h later, ~0.1 nmole of Al[F-18] IMP 449 (84 μCi, 3.11 MBq/0.1 mL) was injected intravenously. The concentration of the Al[F-18] IMP 449 was determined by assuming 100% recovery of added aluminum. Other non-pretargeted control animals received F-18 alone (150 μCi, 5.5 MBq), AlF-18 complex alone (150 μCi, 5.55 MBq), the Al[F-18] IMP 449 peptide alone (84 μCi, 3.11 MBq), or [F-18]FDG (150 μCi, 5.55 MBq). F-18 and [F-18]FDG were obtained on the day of use from IBA Molecular (Somerset, N.J.). Animals receiving [F-18]FDG were fasted overnight, but water was given ad libitum.

At 1.5 h after the radiotracer injection, animals were anesthetized, bled intracardially, and necropsied. Tissues were weighed and counted together with a standard dilution prepared from each of the respective products. Due to the short physical half-life of F-18, standards were interjected between each group of tissues from each animal. Uptake in the tissues is expressed as the counts per gram divided by the total injected activity to derive the percent-injected dose per gram (% ID/g).

Two types of imaging studies were performed. In one set, 3 nude mice bearing small LS174T subcutaneous tumors received either the pretargeted Al[F-18] IMP 449, Al[F-18] IMP 449 alone (not pretargeted), both at 135 μCi (5 MBq; 0.1 nmol), or [F-18]FDG (135 μCi, 5 MBq). At 2 h after the intravenous radiotracer injection, the animals were anesthetized with a mixture of O2/N2O and isoflurane (2%) and kept warm during the scan. Mice were placed in a supine position on the scan bed of an INVEON® animal PET scanner (Siemens Preclinical Solutions, Knoxville, Tenn.). This scanner has an intrinsic spatial resolution of 1.5 mm. Emission scans were acquired over 15 min (FDG) or 30 min (Al[F-18] IMP 449). Scans were reconstructed using INVEON® Acquisition Workplace software (IAW, version 1.2) using an ordered set expectation maximization3D/maximum aposteriori (OSEM3D/MAP) algorithm with the following parameters: matrix 256×256×159, pixel size 0.43×0.43×0.8 mm3 and MAP prior of 0.5 mm.

Representative coronal cross-sections (0.8 mm thick) in a plane located approximately in the center of the tumor were displayed, with intensities adjusted until pixel saturation occurred in any region of the body (excluding the bladder) and without background adjustment.

In a separate dynamic imaging study, a single LS174T-bearing nude mouse that was given the TF2 bsMAb 16 h earlier was anesthetized with a mixture of O2/N2O and isoflurane (2%), placed supine on the camera bed, and then injected intravenously with 219 μCi (8.1 MBq) Al[F-18] IMP 449 (0.16 nmol). Data acquisition was immediately initiated over a period of 120 minutes. Data were histogrammed in 24 frames of 5 min each. The scans were reconstructed using OSEM3D/MAP with the same parameters as described above. Each of the 24-image time frames was examined. For presentation, time-frames ending at 5, 15, 30, 60, 90, and 120 min (ie, the 5-min image is for the period from time-zero to 5 min) were displayed for each cross-section (coronal, sagittal, and transverse). For sections containing tumor, at each interval the image intensity was adjusted until pixel saturation first occurred in the tumor. Image intensity was increased as required over time to maintain pixel saturation within the tumor. Coronal and sagittal cross-sections without tumor taken at the same interval were adjusted to the same intensity as the transverse section containing tumor. Background activity was not adjusted.

Results

While F-18 alone and Al[F-18] complexes had similar uptake in all tissues, considerable differences were found when the complex was chelated to IMP 449 (Table 12). The most striking differences were found in the uptake in the bone, where the non-chelated F-18 was 60- to nearly 100-fold higher in the scapula and ~200-fold higher in the spine. This distribution is expected since F-18, or even a metal-fluoride complex, is known to accrete in bone (Franke et al. 1972, Radiobiol. Radiother. (Berlin) 13:533). Higher uptake was also observed in the tumor and intestines as well as in muscle and blood. The chelated Al[F-18] IMP 449 had significantly lower uptake in all the tissues except the kidneys, illustrating the ability of the chelate-complex to be removed efficiently from the body by urinary excretion. Pretargeting the Al[F-18] IMP 449 using the TF2 anti-CEA bsMAb shifted uptake to the tumor, increasing it from 0.20±0.05 to 6.01±1.72% injected dose per gram at 1.5 h, while uptake in the normal tissues was similar to the Al[F-18] IMP 449 alone. Tumor/nontumor ratios were 146±63, 59±24, 38±15, and 2.0±1.0 for the blood, liver, lung, and kidneys, respectively, with other tumor/tissue ratios>100:1 at this time. Although both F-18 alone and Al[F-18] alone had higher uptake in the tumor than the chelated Al[F-18] IMP 449, yielding tumor/blood ratios of 6.7±2.7 and 11.0±4.6 vs. 5.1±1.5, respectively, tumor uptake and tumor/blood ratios were significantly increased with pretargeting (all P values<0.001).

Biodistribution was also compared to the more commonly used tumor imaging agent, [F-18]FDG, which targets tissues with high glucose consumption and metabolic activity. Its uptake was appreciably higher than the Al[F-18] IMP 449 in all normal tissues, except the kidney. Tumor uptake was similar for both the pretargeted Al[F-18] IMP 449 and [F-18] FDG, but because of the higher accretion of [F-18]FDG in most normal tissues, tumor/nontumor ratios with [F-18]FDG were significantly lower than those in the pretargeted animals (all P values<0.001).

TABLE 12

Biodistribution of TF2-pretargeted Al[F-18] IMP 449 and other control F-18-labeled agents in nude mice bearing LS174T human colonic xenografts. For pretargeting, animals were given TF2 16 h before the injection of the Al[F-18] IMP 449. All injections were administered intravenously.

Percent Injected Dose Per Gram (Mean ± SD) at 1.5 hr Post-Injection

|  | F-18 alone | Al[F-18] alone | Al[F-18] IMP 449 alone | TF2-pretargeted Al[F-18] IMP 449 | [F-18]FDG |
|---|---|---|---|---|---|
| Tumor | 1.02 ± 0.45 | 1.38 ± 0.39 | 0.20 ± 0.05 | 6.01 ± 1.72 | 7.25 ± 2.54 |
| Liver | 0.11 ± 0.02 | 0.12 ± 0.02 | 0.08 ± 0.03 | 0.11 ± 0.03 | 1.34 ± 0.36 |
| Spleen | 0.13 ± 0.06 | 0.10 ± 0.03 | 0.08 ± 0.02 | 0.08 ± 0.02 | 2.62 ± 0.73 |
| Kidney | 0.29 ± 0.07 | 0.25 ± 0.07 | 3.51 ± 0.56 | 3.44 ± 0.99 | 1.50 ± 0.61 |
| Lung | 0.26 ± 0.08 | 0.38 ± 0.19 | 0.11 ± 0.03 | 0.17 ± 0.04 | 3.72 ± 1.48 |
| Blood | 0.15 ± 0.03 | 0.13 ± 0.03 | 0.04 ± 0.01 | 0.04 ± 0.02 | 0.66 ± 0.19 |
| Stomach | 0.21 ± 0.13 | 0.15 ± 0.05 | 0.20 ± 0.32 | 0.12 ± 0.18 | 2.11 ± 1.04 |
| Small Int. | 1.53 ± 0.33 | 1.39 ± 0.34 | 0.36 ± 0.23 | 0.27 ± 0.10 | 1.77 ± 0.61 |
| Large Int. | 1.21 ± 0.13 | 1.78 ± 0.70 | 0.05 ± 0.04 | 0.03 ± 0.01 | 2.90 ± 0.79 |
| Scapula | 6.13 ± 1.33 | 9.83 ± 2.31 | 0.08 ± 0.06 | 0.04 ± 0.02 | 10.63 ± 5.88 |
| Spine | 19.88 ± 2.12 | 19.03 ± 2.70 | 0.13 ± 0.14 | 0.08 ± 0.03 | 4.21 ± 1.79 |
| Muscle | 0.16 ± 0.05 | 0.58 ± 0.36 | 0.06 ± 0.05 | 0.10 ± 0.20 | 4.35 ± 3.01 |
| Brain | 0.15 ± 0.06 | 0.13 ± 0.03 | 0.01 ± 0.01 | 0.01 ± 0.00 | 10.71 ± 4.53 |
| Tumor wt (g) | 0.29 ± 0.07 | 0.27 ± 0.10 | 0.27 ± 0.08 | 0.33 ± 0.11 | 0.25 ± 0.21 |
| N | 6 | 7 | 8 | 7 | 5 |

Figure 2:
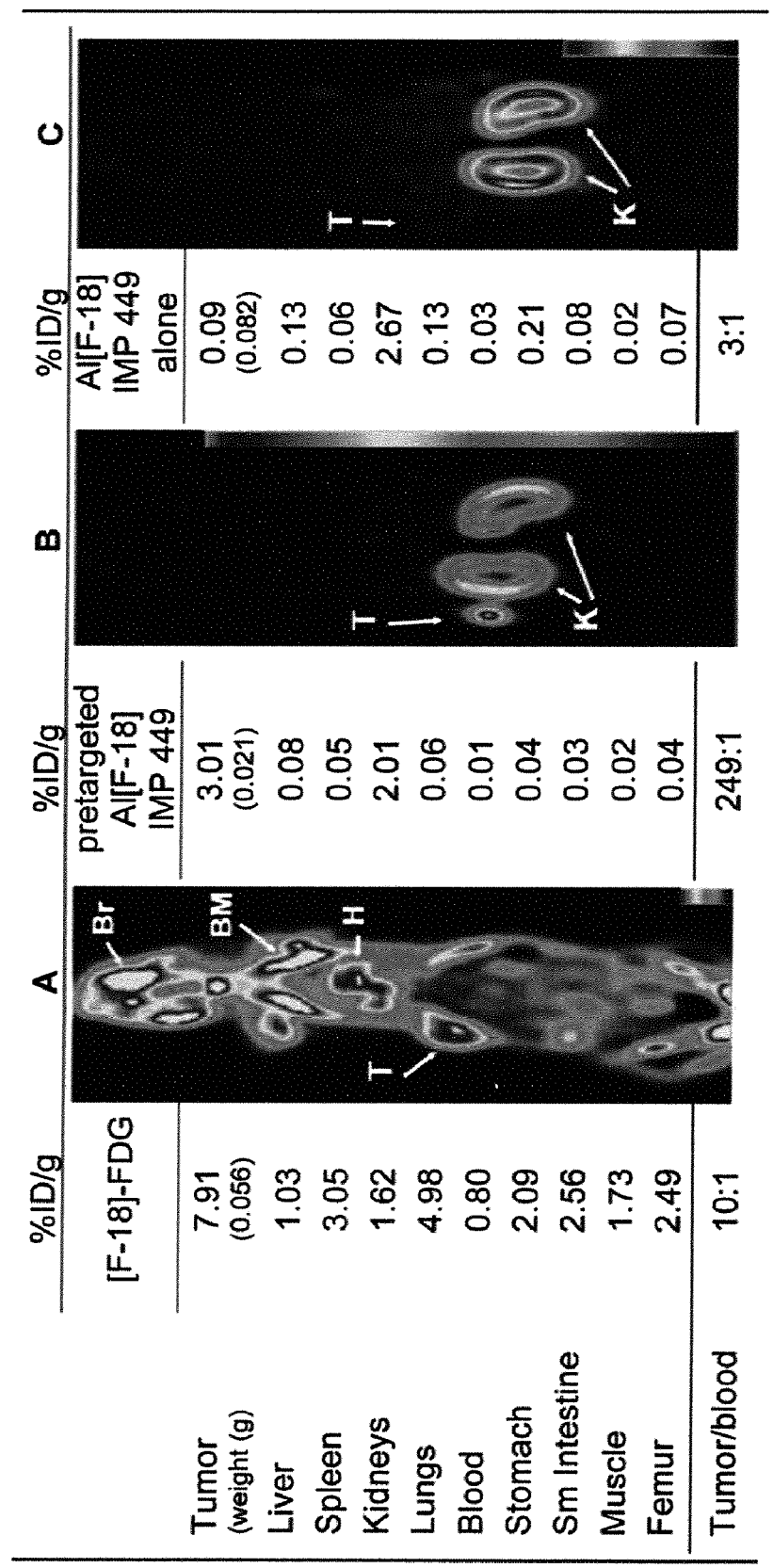
FIG. 2. Biodistribution of F-18-labeled agents in tumor-bearing nude mice by microPET imaging. Coronal slices of 3 nude mice bearing a small, subcutaneous LS174T tumor on each left flank after being injected with either (A) [F-18]FDG, (B) Al[F18] IMP 449 pretargeted with the anti-CEA×anti-HSG bsMAb, (C) Al[F-18] IMP 449 alone (not pretargeted with the bsMAb). Biodistribution data expressed as percent-injected dose per gram (% ID/g) are given for the tissues removed from the animals at the conclusion of the imaging session. Abbreviations: B, bone marrow; H, heart; K, kidney; T, tumor.
Figure 3:
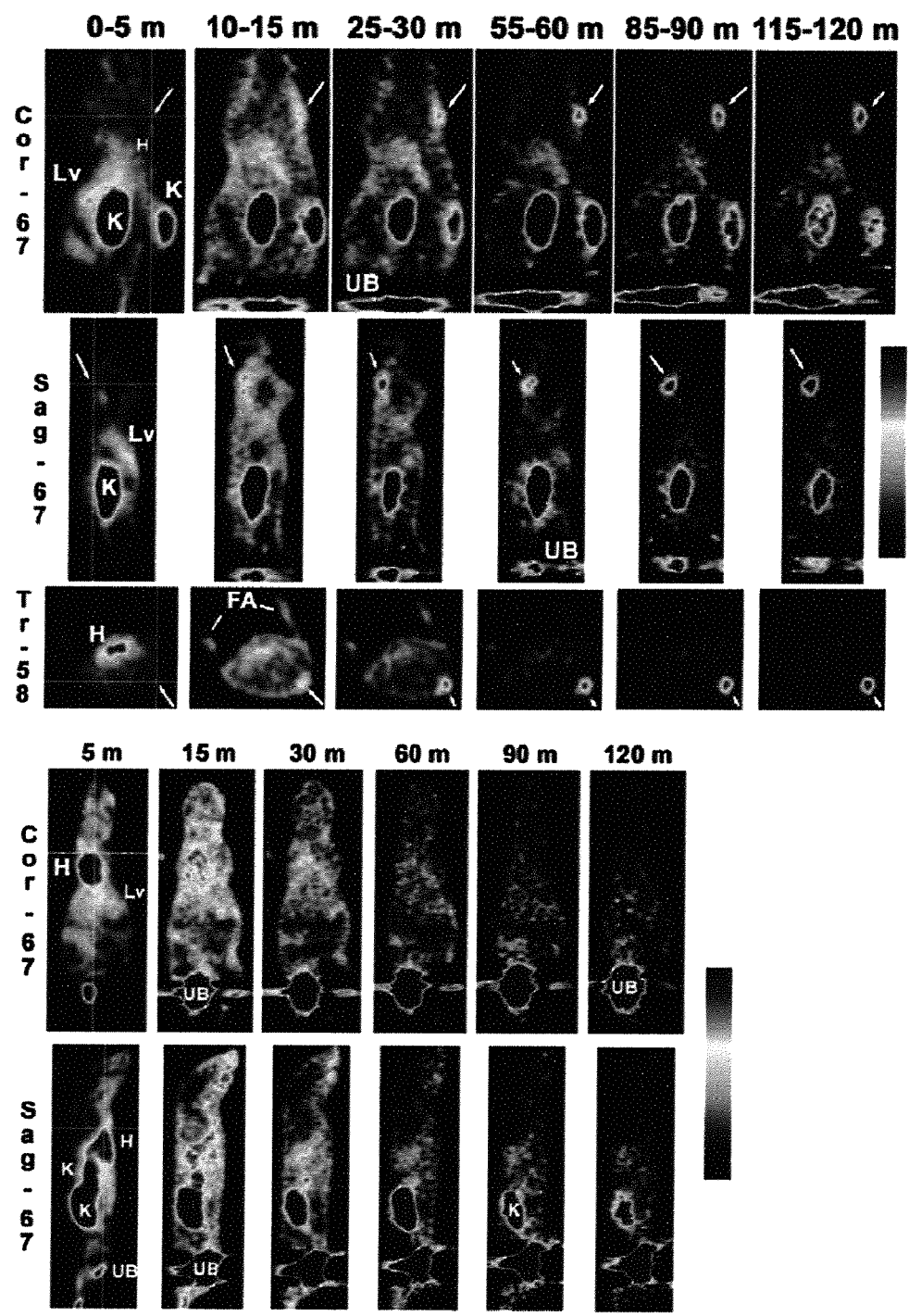
FIG. 3. Dynamic imaging study of pretargeted Al[F-18] IMP 449 given to a nude mouse bearing a 35-mg LS174T human colorectal cancer xenograft in the upper flank. The top 3 panels show coronal, sagittal, and transverse sections, respectively, taken of a region of the body centering on the tumor's peripheral location at 6 different 5-min intervals over the 120-min imaging session. The first image on the left in each sectional view shows the positioning of the tumor at the intersection of the crosshairs, which is highlighted by arrows. The animal was partially tilted to its right side during the imaging session. The bottom 2 panels show additional coronal and sagittal sections that focus on a more anterior plane in the coronal section to highlight distribution in the liver and intestines, while the sagittal view crosses more centrally in the body. Abbreviations: Cor, coronal; FA, forearms; H, heart; K, kidney; Lv, liver; Sag, sagittal; Tr, transverse; UB, urinary bladder.

Several animals were imaged to further analyze the biodistribution of Al[F-18] IMP 449 alone or Al[F-18] IMP 449 pretargeted with TF2, as well [F-18]FDG. Static images initiated at 2.0 h after the radioactivity was injected corroborated the previous tissue distribution data showing uptake almost exclusively in the kidneys (FIG. 2). A 21-mg tumor was easily visualized in the pretargeted animal, while the animal given the Al[F-18] IMP 449 alone failed to localize the tumor, having only renal uptake. No evidence of bone accretion was observed, suggesting that the Al[F-18] was bound firmly to IMP 449. This was confirmed in another pretargeted animal that underwent a dynamic imaging study that monitored the distribution of the Al[F-18] IMP 449 in 5-min intervals over 120 minutes (FIG. 3). Coronal and sagittal slices showed primarily cardiac, renal, and some hepatic uptake over the first 5 min, but heart and liver activity decreased substantially over the next 10 min, while the kidneys remained prominent throughout the study. There was no evidence of activity in the intestines or bone over the full 120-min scan. Uptake in a 35-mg LS174T tumor was first observed at 15 min, and by 30 min, the signal was very clearly delineated from background, with intense tumor activity being prominent during the entire 120-min scanning.

In comparison, static images from an animal given [F-18] FDG showed the expected pattern of radioactivity in the bone, heart muscle, and brain observed previously (McBride et al., 2006, J. Nucl. Med. 47:1678; Sharkey et al., 2008, Radiology 246:497), with considerably more background activity in the body (FIG. 2). Tissue uptake measured in the 3 animals necropsied at the conclusion of the static imaging study confirmed much higher tissue F-18 radioactivity in all tissues. While tumor uptake with [F-18]FDG was higher in this animal than in the pretargeted one, tumor/blood ratios were more favorable for pretargeting; and with much less residual activity in the body, tumor visualization was enhanced by pretargeting.

These studies demonstrate that a biomolecule, in this case the hapten-peptide used in pretargeted imaging, can be rapidly labeled (60 min total preparation time) with F-18 by simply forming an aluminum-fluoride complex that can then be bound by a suitable chelate and incorporated into the hapten-peptide. This can be made more general by simply coupling the Al[F-18]-chelate to any molecule that can accept the chelate and be subsequently purified. In preferred embodiments, the percentage incorporation of label and specific activity of the labeled compound are sufficient that purification of the labeled molecule is not necessary. We were also able to bind F-18 to Al that was already bound to the chelator (data not shown).

This is the first report describing a direct, facile, and rapid method of binding F-18 to various compounds via an aluminum conjugate. The stability of such products, such as Al[F-18], depends on the properties of the chelate used to link F-18 to the molecule of interest. A chelate may be selected with the right configuration to optimize metal incorporation and subsequent stability. The Al[F-18] peptide was stable in vitro and in vivo when bound by a NOTA-based chelate. Yields were within the range found with conventional F-18 labeling procedures. These results further demonstrate the feasibility of PET imaging using F-18-metal chelated to a wide variety of targeting molecules.

Example 15

F-18 Labeling and Pretargeted Biodistribution of IMP 467 in LS174T Tumor Bearing Nude Mice IMP 467 is an alternative targetable construct of use for F-18 labeling and imaging. IMP 467 C-NETA-succinyl-D-Lys(HSG)-D-Tyr-D-Lys(HSG)-NH$_2$, MW 1528.7

Synthesis

Figure 4:
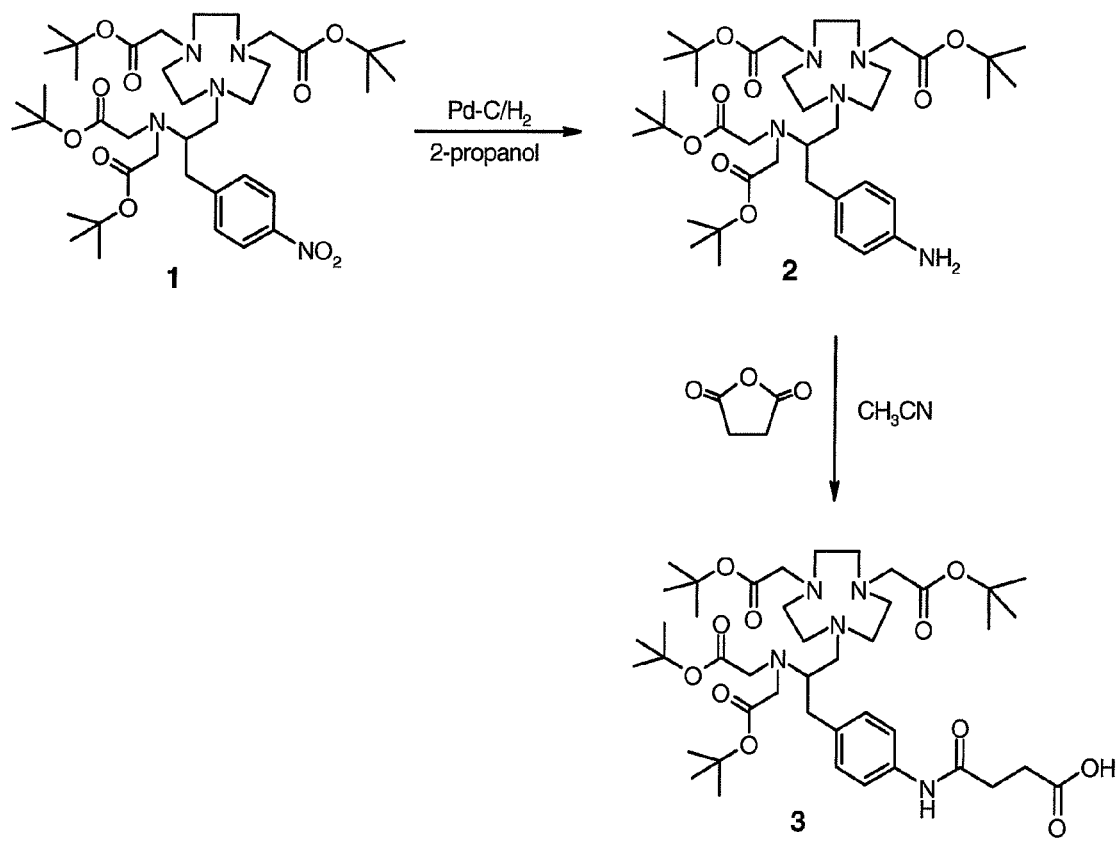
FIG. 4. Synthesis of tetra tert-butyl C-NETA-succinyl.
Figure 5:
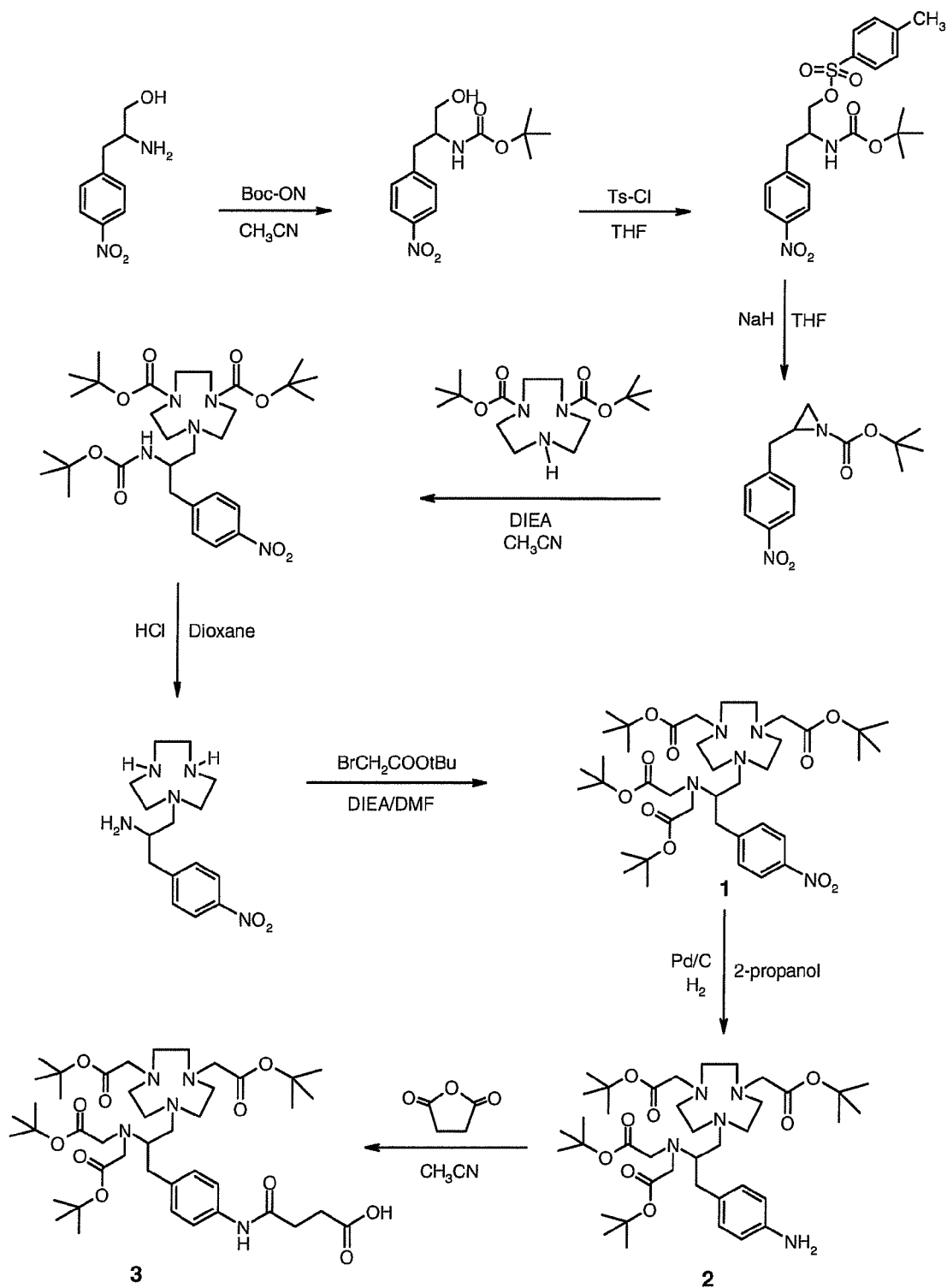
FIG. 5. Detailed synthesis of tetra tert-butyl C-NETA-succinyl.

Tetra tert-butyl C-NETA-succinyl was produced according to FIG. 4. The tert-Butyl{4-[2-(Bis-(tert-butyoxycarbonyl) methyl-3-(4-nitrophenyl)propyl]-7-tert-butyoxycarbonyl[1, 4,7]triazanonan-1-yl} was prepared as described in Chong et al. (J. Med. Chem. 2008, 51:118-125). A more extensive synthetic scheme is shown in FIG. 5. The ligand 3 was purified by high performance liquid chromatography (HPLC) using a WATERS® PrepLC 4000 system equipped with a SUNFIRE® Prep C$_{18}$ reverse-phase column (30×150 mm, 5 μm). Chromatographic separations were achieved using a linear gradient of 100% A (0.1% TFA) to 100% B (90% acetonitrile, 10% water, 0.1% TFA) over 50 min at a flow rate of 45 ml/min, absorbance was detected at 220 nm.

The peptide, IMP-467 C-NETA-succinyl-D-Lys(HSG)-D-Tyr-D-Lys(HSG)-NH$_2$ MH$^+$ 1527.87 was made on Sieber Amide resin by adding the following amino acids to the resin in the order shown: Aloc-D-Lys(Fmoc)-OH, Trt-HSG-OH, the Aloc was cleaved Fmoc-D-Tyr(But)-OH, Aloc-D-Lys (Fmoc)-OH, Trt-HSG-OH, the Aloc was cleaved, tert-Butyl{4-[Bis-(tert-butoxycarbonylmethyl)amino]-3-(4-succinylamidophenyl)propyl]-7-tert-butoxycarbonylmethyl[1,4, 7]triazanonan-1-yl}acetate 3. The peptide was then cleaved from the resin and purified by RP-HPLC to yield 6.3 mg of IMP-467. About 30.6 mg of a product with molecular mass 1034.84 and retention time 8.470 min was also obtained (TFA amide).

The crude peptide was purified by high performance liquid chromatography (HPLC) using a C18 column. Chromatographic separations were achieved using a linear gradient of 100% A (0.1% TFA) to 80% A: 20% B (90% acetonitrile, 10% water, 0.1% TFA) over 80 min at a flow rate of 45 mL/min, absorbance was detected at 220 nm.

Radiolabeling

A 2 mM solution of IMP 467 was prepared in pH 4, 0.1 M NaOAc. The F-18, 139 mCi, was received in 2 mL in a syringe. The activity was eluted through a WATERS® ACCELL™ Plus SEP-PAK® Light QMA cartridge and washed with 5 mL water to remove any metal ion contaminants. The F-18 was then eluted with 1 mL of 0.4 M KHCO$_3$ in the following fractions:

TABLE 13

F-18 elution fractions from SEP-PAK ® QMA

| Fraction | Volume μL | Activity mCi |
| --- | --- | --- |
| 1 | 200 | 19.7 |
| 2 | 50 | 38.0 |
| 3 | 50 | 31.5 |
| 4 | 50 | 15.1 |
| 5 | 50 | 6.81 |
| 6 | 200 | 8.67 |
| 7 | 400 | 2.69 |

Fraction #2 was mixed with 2.5 μL of glacial acetic acid and then 5 μL, 2 mM AlCl$_3$ in pH 4, 0.1 M NaOAc. The peptide, IMP 467 (20 μL, 40 nmol) was added and the sample was heated at 97.5° C. for 16 min. Water, 200 μL was added to the reaction vial and the contents of the vial were removed and place on a 1 cc WAFERS® OASIS® HLB 1 cc (30 mg) column. The liquid in the barrel of the column was drawn through into a 5 mL vial under vacuum. The column was then washed with 3×1 mL water to remove the unbound F-18. The radiolabeled peptide was then eluted into a formulation vial containing buffered ascorbic acid with 2×200 μL 1:1 ethanol/water to obtain 14.65 mCi (70.9% yield) of the HLB purified peptide which had a specific activity of 366 Ci/mmol and a production time of about 30 min. The peptide was then diluted for injection into the mice.

TABLE 14

TF2 Pretargeted Biodistribution in LS174T Tumor Bearing Nude Mice:

| Tissue | n | Weight | STD WT | % ID/g | STD % ID/g | % ID/org | STD % ID/org | T/NT | STD T/NT |
|---|---|---|---|---|---|---|---|---|---|
| Tumor | 6 | 0.741 | 0.522 | 3.415 | 1.265 | 2.742 | 2.112 | 1.0 | 0.0 |
| Liver | 6 | 1.510 | 0.475 | 0.175 | 0.086 | 0.247 | 0.087 | 22.6 | 12.9 |
| Spleen | 6 | 0.131 | 0.075 | 0.326 | 0.261 | 0.036 | 0.020 | 16.3 | 13.3 |
| Kidney | 6 | 0.160 | 0.027 | 3.098 | 0.647 | 0.484 | 0.076 | 1.1 | 0.3 |
| Lung | 6 | 0.178 | 0.032 | 0.204 | 0.059 | 0.035 | 0.011 | 17.0 | 5.0 |
| Blood | 6 | 0.207 | 0.006 | 0.153 | 0.100 | 0.252 | 0.145 | 28.2 | 13.8 |
| Stomach | 6 | 0.443 | 0.089 | 0.186 | 0.148 | 0.079 | 0.053 | 23.3 | 9.4 |
| Small Int. | 6 | 1.086 | 0.121 | 0.338 | 0.125 | 0.359 | 0.117 | 10.5 | 2.9 |
| Large Int. | 6 | 0.804 | 0.116 | 0.115 | 0.047 | 0.093 | 0.045 | 34.5 | 21.1 |
| Scapula | 6 | 0.154 | 0.040 | 0.123 | 0.020 | 0.019 | 0.005 | 28.0 | 10.9 |
| Spine | 6 | 0.199 | 0.022 | 0.503 | 0.372 | 0.101 | 0.082 | 9.4 | 6.5 |
| Muscle | 6 | 0.088 | 0.021 | 0.200 | 0.237 | 0.014 | 0.014 | 56.3 | 64.3 |
| Brain | 6 | 0.329 | 0.049 | 0.013 | 0.002 | 0.004 | 0.000 | 260.4 | 104.0 |

TABLE 15

Peptide Alone Biodistribution in LS174T Tumor Bearing Nude Mice:

| Tissue | n | Weight | STD WT | % ID/g | STD % ID/g | % ID/org | STD % ID/org | T/NT | STD T/NT |
|---|---|---|---|---|---|---|---|---|---|
| Tumor | 4 | 1.235 | 0.612 | 0.287 | 0.055 | 0.330 | 0.138 | 1.00 | 0.00 |
| Liver | 4 | 1.199 | 0.172 | 0.086 | 0.018 | 0.101 | 0.009 | 3.35 | 0.37 |
| Spleen | 4 | 0.105 | 0.026 | 0.075 | 0.017 | 0.008 | 0.001 | 3.87 | 0.17 |
| Kidney | 4 | 0.140 | 0.019 | 2.034 | 0.517 | 0.290 | 0.095 | 0.16 | 0.08 |
| Lung | 4 | 0.126 | 0.023 | 0.129 | 0.034 | 0.016 | 0.001 | 2.24 | 0.17 |
| Blood | 4 | 0.212 | 0.004 | 0.043 | 0.007 | 0.067 | 0.014 | 6.91 | 1.89 |
| Stomach | 4 | 0.590 | 0.125 | 0.023 | 0.009 | 0.013 | 0.003 | 13.43 | 3.26 |
| Small Int. | 4 | 1.021 | 0.122 | 0.235 | 0.082 | 0.246 | 0.117 | 1.34 | 0.50 |
| Large Int. | 4 | 0.564 | 0.056 | 0.073 | 0.023 | 0.041 | 0.015 | 4.04 | 0.53 |
| Scapula | 4 | 0.120 | 0.025 | 0.144 | 0.025 | 0.017 | 0.004 | 2.04 | 0.51 |
| Spine | 4 | 0.151 | 0.020 | 0.284 | 0.058 | 0.042 | 0.006 | 1.03 | 0.18 |
| Muscle | 4 | 0.098 | 0.019 | 0.064 | 0.022 | 0.006 | 0.003 | 4.80 | 1.49 |
| Brain | 4 | 0.287 | 0.029 | 0.013 | 0.003 | 0.004 | 0.001 | 22.19 | 5.06 |

The data indicate that AlF-18 IMP 467 was stable in-vivo and the peptide targeted the antibody on the tumor surface.

In another experiment, the amount of binding of Al—F-18 to peptide was determined in a constant volume (63 µL) with a constant amount of Al (6 nmol) and F-18, but varying the amount of peptide added. The yield of labeled peptide decreased with a decreasing concentration of peptide as follows: 40 nmol peptide (82% yield); 30 nmol (79% yield); 20 nmol (75% yield); 10 nmol (49% yield).

Example 16

Synthesis and Labeling of IMP 461 and IMP 462 NOTA-Conjugated Peptides

The simplest possible NOTA ligand (protected for peptide synthesis) was prepared and incorporated into two peptides—IMP 461 and IMP 462.

Figure 6:
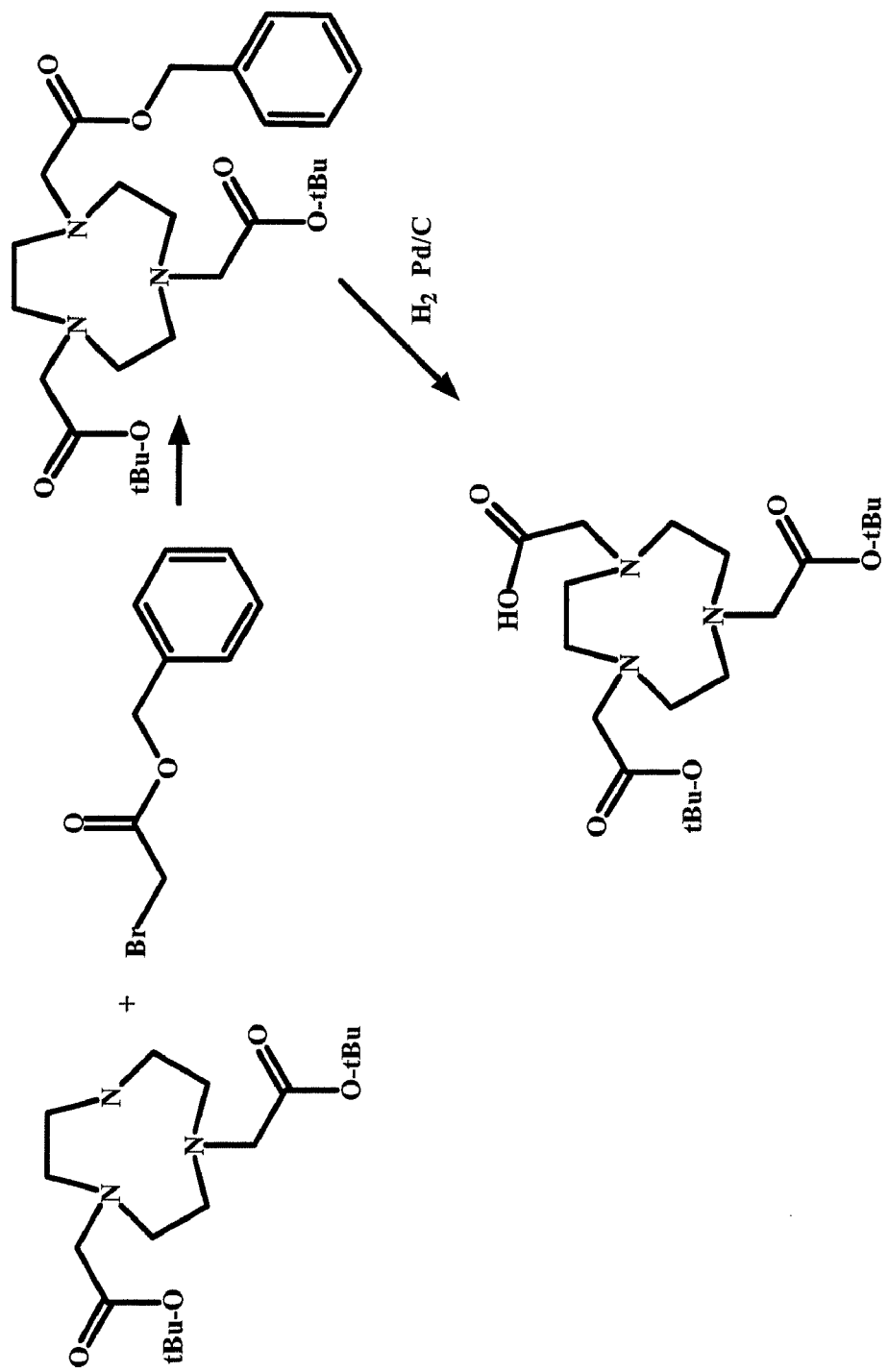
FIG. 6. Synthesis of Bis-t-butyl NOTA.

Synthesis of Bis-t-butyl-NOTA (FIG. 6)

NO2ATBu (0.501 g $1.4 \times 10^{-3}$ mol) was dissolved in 5 mL anhydrous acetonitrile. Benzyl-2-bromoacetate (0.222 mL, $1.4 \times 10^{-3}$ mol) was added to the solution followed by 0.387 g of anhydrous $K_2CO_3$. The reaction was allowed to stir at room temperature overnight. The reaction mixture was filtered and concentrated to obtain 0.605 g (86% yield) of the benzyl ester conjugate. The crude product was then dissolved in 50 mL of isopropanol, mixed with 0.2 g of 10% Pd/C (under Ar) and placed under 50 psi $H_2$ for 3 days. The product was then filtered and concentrated under vacuum to obtain 0.462 g of the desired product ESMS MH⁻ 415.

Synthesis of IMP 461

Figure 8:
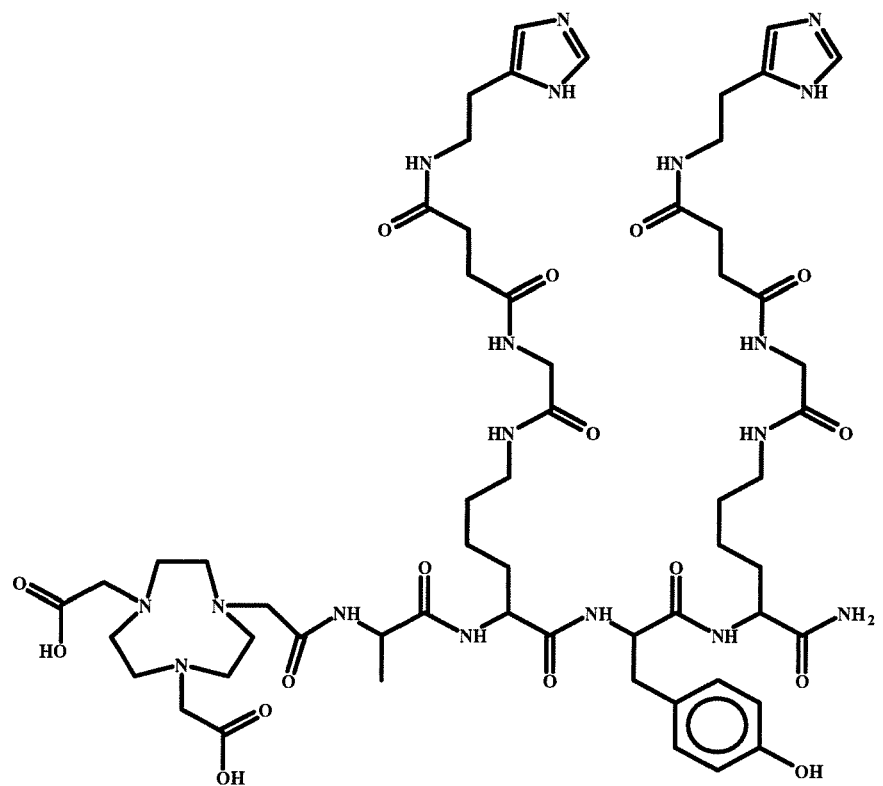
FIG. 8. Structure of IMP 461.

The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Ala-OH, and Bis-t-butylNOTA-OH. The peptide was then cleaved and purified by HPLC to afford the product IMP 461 ESMS MH⁺1294 (FIG. 8).

Synthesis of IMP 462

Figure 9:
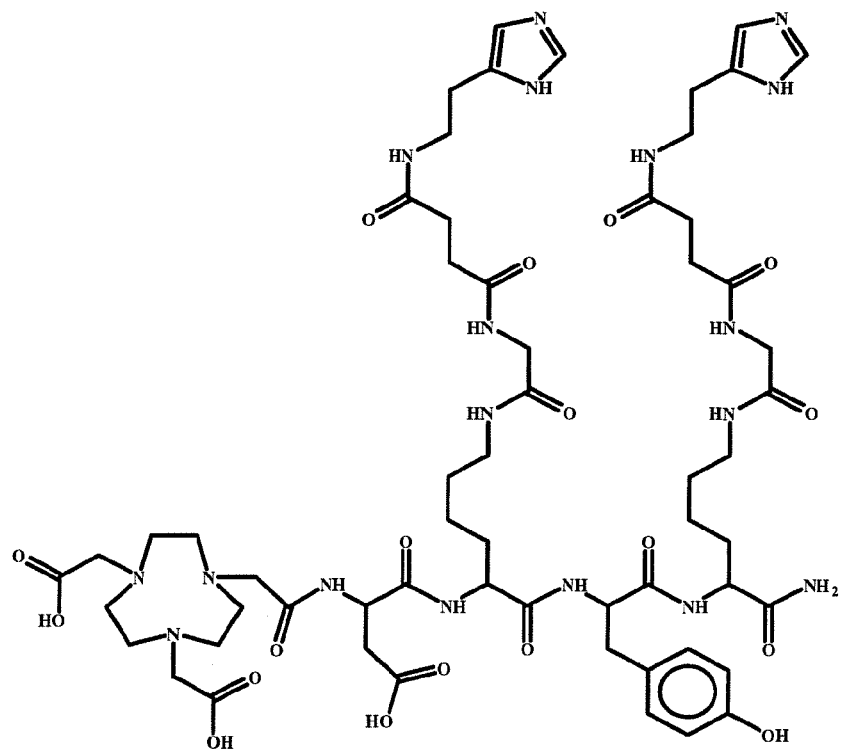
FIG. 9. Structure of IMP 462.

The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Asp(But)-OH, and Bis-t-butyl-NOTA-OH. The peptide was then cleaved and purified by HPLC to afford the product IMP 462 ESMS MH⁺1338 (FIG. 9). NOTA esters were added to the peptides on the peptide synthesizer.

F-18 Labeling of the Peptides (IMP 461 & IMP 462)

The peptides were dissolved in pH 4.13, 0.5 M NaOAc to make a 0.05 M peptide solution, which was stored in the freezer until needed. The F-18 was received in 2 mL of water and trapped on a SEP-PAK® Light, WATERS® ACCELL™ Plus QMA Cartridge, which had been previously washed with 5 mL of 0.4 M $KHCO_3$ followed by a 5 mL water wash. The column was washed with 5 mL of DI water to removed undesired contaminants from the F-18. The F-18 was then eluted from the column with 200 μL aliquots of 0.4 M $KHCO_3$ with most of the activity in the second aliquot. The bicarbonate in the aliquots was neutralized to ~pH 4 by the addition of 10 μL of glacial acetic acid to the vials before the addition of the activity. A 100 μL aliquot of the purified F-18 solution was removed and mixed with 3 μL, 2 mM Al in pH 4, 0.1 M NaOAc. The peptide, 10 μL (0.05 M) was added and the solution was heated at ~100° C. for 15 min. The crude reaction mixture was diluted with 700 μL DI water and placed on an HLB column and the liquid was then drawn through the column into a waste vial. The reaction vial was rinsed with an additional 1 mL of DI water and pulled (under vacuum) through the HLB column. The HLB column was washed with additional 2×1 mL portions of DI water. The column was moved to an empty vial and eluted with 2×100 μL of 1:1 $EtOH/H_2O$ to obtain the purified F-18 labeled peptide.

All of the labeling studies in Table 16 were performed with the same number of moles of peptide and aluminum but the IMP 461 and IMP 462 reactions were done with half the volume of purified F-18 solution.

TABLE 16

Comparison of yields of different NOTA containing peptides

| Peptide | Yield |
|---|---|
| IMP 449 | 44% |
| IMP 460 | 5.8% |
| IMP 461 | 31% |
| IMP 467 | 87% |

Human Serum Stability Test

An aliquot of the HLB purified peptide (~30 μL) was diluted with 200 μL human serum (previously frozen) and placed in the 37° C. HPLC sample chamber. Aliquots were removed at various time points and analyzed by HPLC. The HPLC analysis showed very high stability of the F-18 labeled peptides in serum at 37° C. for at least five hours (not shown). There was no detectable breakdown of the F-18 labeled peptide product after a five hour incubation in serum (not shown).

The IMP 461 and IMP 462 ligands have two carboxyl groups available to bind the aluminum whereas the NOTA ligands described above had three carboxyl groups. The serum stability study showed that the complexes with the new ligands were extremely stable in serum under conditions replicating in vivo use.

Example 17

Synthesis and Labeling of IMP 468 Bombesin Peptide

Figure 10:
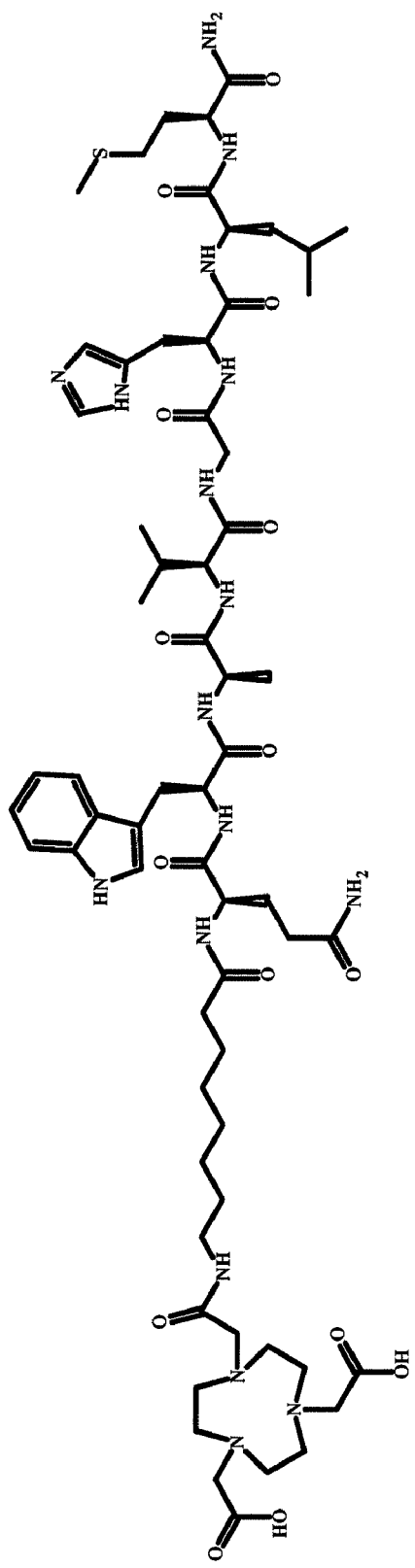
FIG. 10. Structure of IMP 468.

As discussed above, the F-18 labeled targeting moieties are not limited to antibodies or antibody fragments, but rather can include any molecule that binds specifically or selectively to a cellular target that is associated with or diagnostic of a disease state or other condition that may be imaged by F-18 PET. Bombesin is a 14 amino acid peptide that is homologous to neuromedin B and gastrin releasing peptide, as well as a tumor marker for cancers such as lung and gastric cancer and neuroblastoma. IMP 468 (FIG. 10) was synthesized as a bombesin analogue and labeled with F-18 to target the gastrin-releasing peptide receptor.

The peptide was synthesized by Fmoc based solid phase peptide synthesis on Sieber amide resin, using a variation of a synthetic scheme reported reported in the literature (Prasanphanich et al., 2007, PNAS USA 104:12463-467). The synthesis was different in that a bis-t-butyl NOTA ligand was add to the peptide during peptide synthesis on the resin. In contrast, the 2007 report of Prasanphanich stated that the peptide was made first and then conjugated to unprotected NOTA in aqueous solution.

IMP 468 (0.0139 g, $1.02 \times 10^{-5}$ mol) was dissolved in 203 μL of 0.5 M pH 4.13 NaOAc buffer. The peptide dissolved but formed a gel on standing so the peptide gel was diluted with 609 μL of 0.5 M pH 4.13 NaOAc buffer and 406 μL of ethanol to produce an $8.35 \times 10^{-3}$ M solution of the peptide. The F-18 was purified on a QMA cartridge and eluted with 0.4 M $KHCO_3$ in 200 μL fractions. Each of the F-18 bicarbonate fractions was neutralized with 10 μL of glacial acetic acid. The purified F-18, 40 μL, 1.13 mCi was mixed with 3 μL of 2 mM $AlCl_3$ in pH 4, 0.1 M NaOAc buffer. IMP 468 (59.2 μL, $4.94 \times 10^{-7}$ mol) was added to the A1F-18 solution and placed in a 108° C. heating block for 15 min. The crude product was diluted with water and placed on a WATERS® 30 mg, 1 cc syringe barrel, HLB column. The solution was eluted into a crimp sealed vial, which was under vacuum. The reaction vial was rinsed with 1 mL water, which was added to the HLB column. The column was then rinsed with 3×1 mL water. The column was moved to an empty vial and eluted with 2×200 μL of 1:1 $EtOH/H_2O$ to obtain the purified F-18 labeled peptide in 34% yield.

TABLE 17

AlF-18 IMP 468 after HLB purification

| Name | Start (mins) | End (mins) | Retention (mins) | Height (CPM) | Area (CPM) | % ROI (%) | % Total (%) |
|---|---|---|---|---|---|---|---|
| Bkg 1 | 0.00 | 1.10 | 0.50 | 130.0 | | | |
| Region 1 | 13.20 | 14.40 | 13.60 | 340.0 | 872.1 | 4.37 | 4.06 |
| Region 2 | 14.40 | 16.50 | 14.80 | 10100.0 | 19067.9 | 95.63 | 88.83 |
| Bkg 2 | 16.50 | 17.60 | 17.20 | 120.0 | | | |
| | | | | | 19940.0 | 100.00 | 92.89 |

Total Area: 21465.5 CPM
Average Background: 59.0 CPM
Unallocated Area: −16179.1 CPM The labeled peptide may be purified by HPLC for in-vivo targeting studies to increase the specific activity by separating the excess cold peptide from the AlF-18 labeled peptide.

The cold AlF-19 labeled peptide was also prepared for receptor binding competition studies. An 0.02 M $AlCl_3$ solution (604 μL, $1.208 \times 10^{-5}$ mol, in 0.5 M NaOAc, pH 4) was mixed with 130 μL, 0.1 M NaF ($1.30 \times 10^{-5}$ mol) in 0.5 M NaOAc pH 4. The AlF-19 solution was incubated at room temperature for 12 min and then added to 0.0165 g, $1.21 \times 10^{-5}$ mol of IMP 468. The solution was heated in a 103° C. heating block for 16 min. Analytical HPLC of the crude product showed two main products one, 0.0034 g at 13.8 min (Al IMP 468 $MH^+$ 1391) and another, 0.0060 g at 14.8 min (AlF-19 IMP 468 $MH^+$ 1411, data not shown).

Example 18

Imaging of Tumors Using F-18 Labeled Bombesin

A NOTA-conjugated bombesin derivative (IMP 468) was prepared as described in Example 17 above. We began testing its ability to block radiolabeled bombesin from binding to PC-3 cells as was done by Prasanphanich et al. (PNAS 104: 12462-12467, 2007). Our initial experiment was to determine if IMP-468 could specifically block bombesin from binding to PC-3 cells. We used IMP-333 as a non-specific control. In this experiment, 3×10$^6$ PC-3 cells were exposed to a constant amount (~50,000 cpms) of $^{125}$I-Bombesin (Perkin-Elmer) to which increasing amounts of either IMP-468 or IMP-333 was added. A range of 56 to 0.44 nM was used as our inhibitory concentrations.

The results showed that we could block the binding of $^{125}$I-BBN with IMP-468 but not with the control peptide (IMP-333) (not shown), thus demonstrating the specificity of IMP-468. Prasanphanich indicated an IC$_{50}$ for their peptide at 3.2 nM which is approximately 7-fold lower than what we found with IMP-468 (21.5 nM).

This experiment was repeated using a commercially available BBN peptide. We increased the amount of inhibitory peptide to a range of 250 to 2 nM to block the $^{125}$I-BBN from binding to PC-3 cells. We observed very similar IC$_{50}$-values for IMP-468 and the BBN positive control with an IC$_{50}$-value higher (35.9 nM) than what was reported previously (3.2 nM) but close to what the BBN control achieved (24.4 nM).

To examine in vivo targeting, the distribution of $^{18}$F IMP 468 was examined in scPC3 prostate cancer xenograft bearing nude male mice; alone vs blocked with bombesin. For radiolabeling, aluminum chloride (10 μL, 2 mM), 51.9 mCi of F-18 (from QMA cartridge), acetic acid, and 60 μL of IMP 468 (8.45 mM in ethanol/NaOAc) were heated at 100° C. for 15 min. The reaction mixture was purified on reverse phase HPLC, collecting fractions every 0.25 min. Fractions 40 and 41 (3.56, 1.91 mci) were pooled and applied to HLB column for solvent exchange. The product was eluted in 800 μL (3.98 mCi) and 910 μCi remained on the column. ITLC developed in saturated NaCl showed 0.1% unbound activity.

Figure 15:
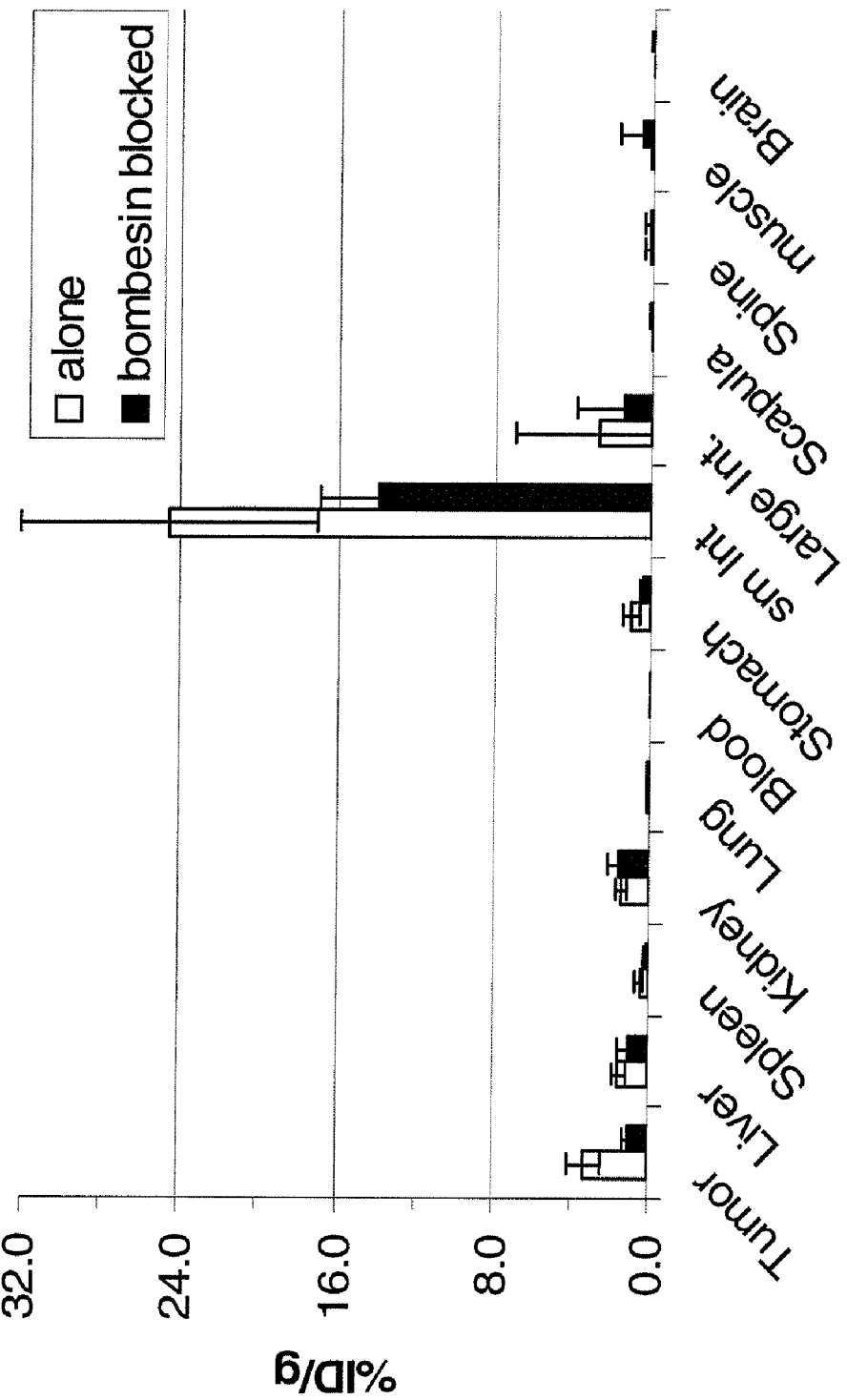
FIG. 15. In vivo tissue distribution with F-18 labeled IMP 468 bombesin analogue.

A group of six tumor-bearing mice were injected with $^{18}$F-IMP 468 (167 μCi, ~9×10$^{-10}$ mol) and necropsied 1.5 h later. Another group of six mice were injected iv with 100 μg (6.2×10$^{-8}$ mol) of bombesin 18 min before administering $^{18}$F IMP 468. The second group was also necropsied 1.5 h post injection. The data shows specific targeting of the tumor with $^{18}$F IMP 468 (FIG. 15). Tumor uptake of the peptide is reduced when bombesin was given 18 min before the $^{18}$F-IMP 468 (FIG. 15). Biodistribution data indicates in vivo stability of $^{18}$F-IMP 468 for at least 1.5 h. Animal #1 in the peptide alone group showed slightly higher spine and muscle uptake, possibly due to contamination. Animal #2 in the bombesin blocked group showed higher peptide uptake in several tissues compared to the other mice in the group.

TABLE 18

$^{18}$F-IMP 468 alone (167 μCi, ~9 × 10$^{-10}$ mol), % ID/g at 1.5 h post injection:

| Tissue | Mean | SD | Animal 1 | Animal 2 | Animal 3 | Animal 4 | Animal 5 | Animal 6 |
|---|---|---|---|---|---|---|---|---|
| Tumor | 3.216 | 0.859 | 2.356 | 4.206 | 4.111 | 3.546 | 2.802 | 2.274 |
| Tumor wt, g | 0.412 | 0.228 | 0.240 | 0.820 | 0.540 | 0.330 | 0.285 | 0.254 |
| Liver | 1.503 | 0.365 | 1.452 | 1.130 | 1.265 | 1.427 | 2.180 | 1.563 |
| Spleen | 0.446 | 0.210 | 0.251 | 0.744 | 0.285 | 0.609 | 0.525 | 0.260 |
| Kidney | 1.412 | 0.280 | 1.357 | 1.178 | 1.860 | 1.626 | 1.327 | 1.126 |
| Lung | 0.095 | 0.020 | 0.123 | 0.089 | 0.088 | 0.080 | 0.073 | 0.117 |
| Blood | 0.052 | 0.006 | 0.059 | 0.059 | 0.048 | 0.054 | 0.046 | 0.045 |
| Stomach | 1.006 | 0.452 | 1.251 | 0.772 | 0.552 | 0.505 | 1.530 | 1.424 |
| Sm. Int. | 24.587 | 7.511 | 29.629 | 20.362 | 32.347 | 13.302 | 30.816 | 21.065 |
| Large Int. | 2.765 | 4.168 | 0.579 | 0.868 | 0.635 | 11.202 | 2.035 | 1.273 |
| Scapula | 0.045 | 0.026 | 0.031 | 0.026 | 0.036 | 0.096 | 0.048 | 0.034 |
| Spine | 0.196 | 0.234 | 0.647 | 0.041 | 0.049 | 0.041 | 0.227 | 0.173 |
| muscle | 0.060 | 0.084 | 0.232 | 0.029 | 0.021 | 0.024 | 0.020 | 0.032 |
| Brain | 0.020 | 0.009 | 0.014 | 0.023 | 0.012 | 0.019 | 0.037 | 0.015 |
| Body Wt. | 28.82 | 2.31 | 28.04 | 28.74 | 28.18 | 29.61 | 25.64 | 32.68 |

Larger tumors showed higher uptake of $^{18}$F-IMP 468, possibly due to higher receptor expression in larger tumors.

TABLE 19

Bombesin (100 μg, 6.2 × 10$^{-8}$ mol)→18 min → $^{18}$F-IMP 468 (167 μCi, ~9 × 10$^{-10}$ mol), % ID/g at 1.5 h post injection

| Tissue | Mean | SD | Animal 1 | Animal 2 | Animal 3 | Animal 4 | Animal 5 | Animal 6 |
|---|---|---|---|---|---|---|---|---|
| Tumor | 1.053 | 0.200 | 0.842 | 0.998 | 1.220 | 1.296 | 1.147 | 0.814 |
| Tumor wt | 0.479 | 0.160 | 0.275 | 0.284 | 0.508 | 0.577 | 0.607 | 0.623 |
| Liver | 1.005 | 0.553 | 0.939 | 1.244 | 1.982 | 0.813 | 0.428 | 0.627 |
| Spleen | 0.187 | 0.101 | 0.354 | 0.086 | 0.226 | 0.085 | 0.164 | 0.207 |
| Kidney | 1.613 | 0.450 | 2.184 | 1.965 | 1.841 | 1.432 | 1.067 | 1.189 |
| Lung | 0.114 | 0.035 | 0.125 | 0.084 | 0.149 | 0.083 | 0.086 | 0.159 |
| Blood | 0.033 | 0.006 | 0.029 | 0.043 | 0.031 | 0.032 | 0.037 | 0.025 |
| Stomach | 0.413 | 0.223 | 0.356 | 0.736 | 0.387 | 0.617 | 0.159 | 0.225 |
| Sm Int. | 13.890 | 3.024 | 16.266 | 12.387 | 11.312 | 18.805 | 13.249 | 11.321 |
| Large Int. | 1.359 | 2.452 | 0.556 | 0.352 | 0.264 | 0.235 | 6.359 | 0.388 |
| Scapula | 0.092 | 0.077 | 0.033 | 0.228 | 0.071 | 0.059 | 0.135 | 0.025 |
| Spine | 0.208 | 0.187 | 0.296 | 0.551 | 0.073 | 0.086 | 0.153 | 0.089 |
| muscle | 0.604 | 1.081 | 0.127 | 0.546 | 0.061 | 2.777 | 0.073 | 0.040 |
| Brain | 0.063 | 0.111 | 0.019 | 0.291 | 0.012 | 0.018 | 0.023 | 0.019 |
| Body Wt. | 29.36 | 1.45 | 29.72 | 31.85 | 29.02 | 27.38 | 29.09 | 29.08 |

The biodistribution data above showed F-18 IMP 468 tumor targeting that was in the same range as reported for the same peptide labeled with Ga-68 by Prasanphanich et. al. The results demonstrate that the AlF-18 peptide labeling method can be used in vivo to target receptors that are upregulated in tumors, using targeting molecules besides antibodies. The tumor targeting was significant with a P value of P=0.0013.

Example 19

Synthesis and Labeling of Somatostatin Peptide IMP 466

IMP 466 NOTA-D-Phe-Cys-Phe-D-Trp-Lys-Thr-Cys-Throl MH$^+$ 1305

A NOTA-conjugated somatostatin peptide (IMP 466) was made by standard Fmoc based solid phase peptide synthesis, as described in the preceding Examples, to produce a linear peptide. The C-terminal Throl residue is threoninol. The peptide was cyclized by treatment with DMSO overnight.

The peptide, 0.0073 g, 5.59×10$^{-6}$ mol was dissolved in 111.9 µL of 0.5 M pH 4 NaOAc buffer to make a 0.05 M solution of IMP 466. The solution formed a gel over time so it was diluted to 0.0125 M by the addition of more 0.5 M NaOAc buffer.

F-18 was purified and concentrated with a QMA cartridge to provide 200 µL of F-18 in 0.4 M KHCO$_3$. The bicarbonate solution was neutralized with 10 µL of glacial acetic acid. A 40 µL aliquot of the neutralized F-18 eluent was mixed with 3 µL of 2 mM AlCl$_3$ followed by the addition of 40 µL of 0.0125 M IMP 466 solution. The mixture was heated at 105° C. for 17 min. The reaction was then purified on a Waters 1 cc (30 mg) HLB column by loading the reaction solution onto the column and washing the unbound F-18 away with water (3 mL) and then eluting the radiolabeled peptide with 2×200 µL 1:1 EtOH water. The yield of the radiolabeled peptide after HLB purification was 34.6%. The radiolabeled peptide contained two radiometric peaks, which had an HPLC retention time that was close to the unlabeled IMP 466 retention time (not shown).

The cold AlF peptide was also prepared for in-vitro competition assays. Both the radiolabeled HPLC and the cold AlF peptide showed that two AlF products were formed. These are possibly diastereomers.

A cold AlF solution was prepared by mixing 356 µL of 0.02 M AlCl$_3$, 7.13×10$^{-6}$ mol in 0.5 M pH 4 NaOAc with 71.3 µL 0.1 M, 7.13×10$^{-6}$ mol NaF in 0.5 M pH 4 NaOAc. The AlF solution was then mixed with the peptide, IMP 466, 0.0093 g, 7.13×10$^{-6}$ mol and heated at 103° C. for 17 min. The reaction gave three main peaks by HPLC-one shorter retention time peak (13.5 min) and two longer retention time peaks (14.8 min and 14.9 min) (not shown). The retention time of IMP 466 was 14.7 min. The reaction mixture was purified by C18 reverse phase HPLC. The shorter retention time (13.5 min) product corresponded to the peptide plus aluminum MH$^+$ 1329.

The longer retention time products 14.8 and 14.9 min (0.0037 g) corresponded to the AlF peptides with an MH$^+$ 1349. Two AlF products are formed in the radiometric trace, which correspond with the two AlF products for the cold peptide.

TABLE 20

| AlF-18 IMP 466, HLB purified | | | | | | |
|---|---|---|---|---|---|---|
| Name | Start (mins) | End (mins) | Retention (mins) | Height (CPM) | Area (CPM) | % ROI (%) | % Total (%) |
| Bkg 1 | 1.30 | 1.50 | 1.30 | 90.0 | | | |
| Region 1 | 14.40 | 15.40 | 14.80 | 4380.0 | 14737.8 | 100.00 | 79.62 |

TABLE 20-continued

| AlF-18 IMP 466, HLB purified | | | | | | |
|---|---|---|---|---|---|---|
| Name | Start (mins) | End (mins) | Retention (mins) | Height (CPM) | Area (CPM) | % ROI (%) | % Total (%) |
| Bkg 2 | 22.50 | 22.60 | 22.50 | 70.0 | | | |
| Bkg 3 | 23.30 | 23.40 | 23.30 | 110.0 | | | |
| 1 Peak | | | | | 14737.8 | 100.00 | 79.62 |

Example 20

Synthesis and Labeling of IMP 470

Figure 11:
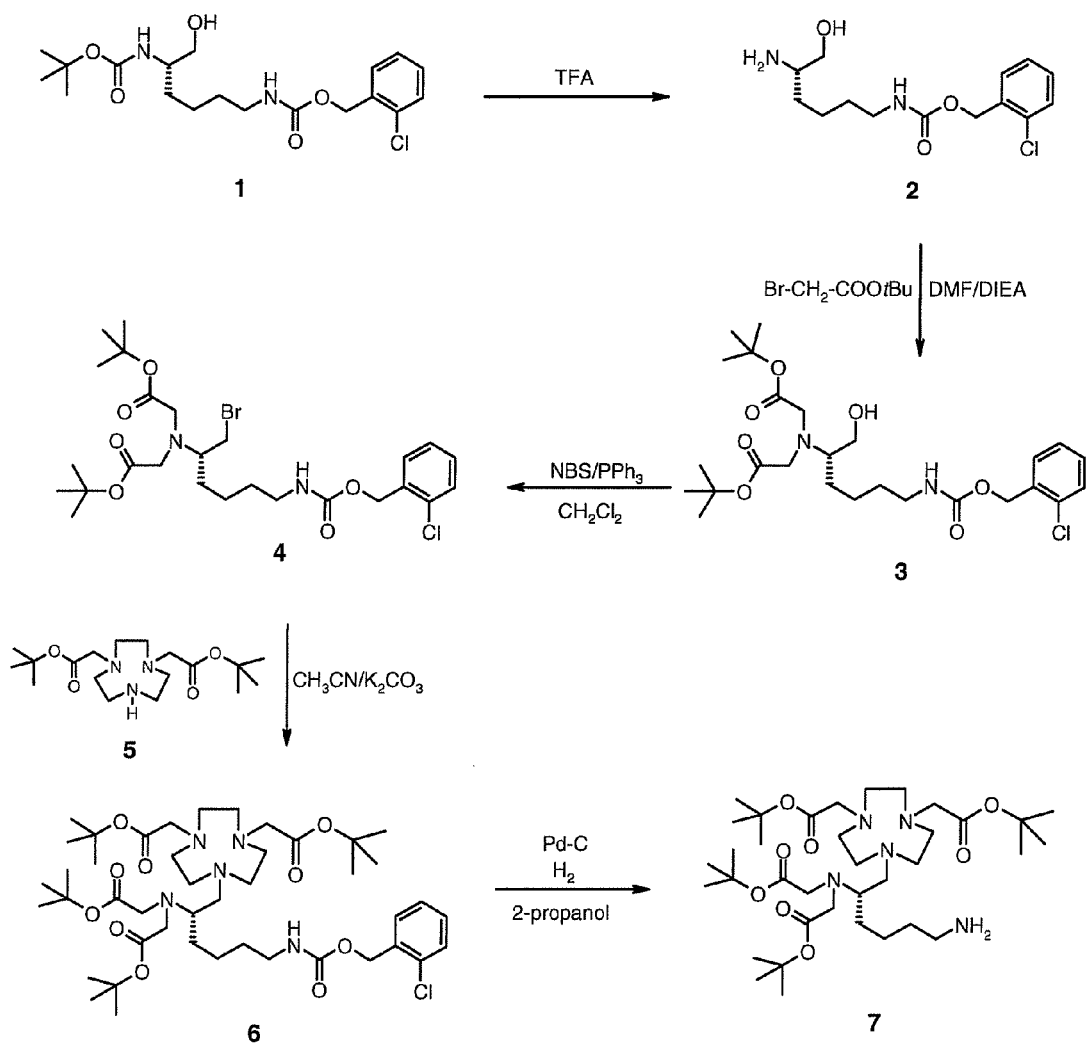
FIG. 11. Synthesis of tetra tert-butyl L-NETA.

The results with IMP-467 (Example 15) prompted us to evaluate a more easily accessible bifunctional version of C-NETA. The synthetic route to tetra tert-butyl L-NETA 7 (shown in FIG. 11) starts with Boc deprotection of 1 using TFA, followed by a double alkylation of 2 with t-butyl bromoacetate to yield alcohol 3. Reaction of 3 with PPh$_3$/NBS generates the bromide 4. Coupling of the bisubstituted TACN 5 in CH$_3$CN with 4 using K$_2$CO$_3$ provided the macrocycle 6. tert-butyl protected L-NETA 7 is obtained by 2-Cl—Z deprotection using hydrogenation over Pd/C in near quantitative yield.

This free amine in 7 can be further converted to isothiocyanate, maleimide, bromo acetyl, or succinyl, making it a suitable group for conjugation to a tumor targeting peptide or antibody or a variety of other potential targeting moieties.

IMP 470 L-NETA-succinyl-D-Lys(HSG)-D-Tyr-D-Lys(HSG)-NH$_2$ M$^+$ 1494.68

The peptide, IMP-470 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH. The free amine obtained after the removal of Aloc was reacted with succinic anhydride, to generate a carboxylic acid group at the N-terminus, which is activated using DIC in DMF and subsequently coupled with tert-butyl protected L-NETA 7. The peptide was then cleaved from the resin and purified by RP-HPLC to yield 16.4 mg of IMP-470. A product with molecular mass 1037.15 corresponding to the peptide without L-NETA and with retention time 9.001 min was also obtained.

For RP-HPLC analysis, a WATERS® 2695 HPLC system equipped with a PHENOMENEX® GEMINI™ C$_{18}$ reverse-phase column (4.6×250 mm), using a linear gradient of 100% A (0.1% TFA) to 100% B (90% acetonitrile, 10% water, 0.1% TFA) over 30 min at a flow rate of 1 mL/min, absorbance was detected at 220 nm. Radioactivity was measured by a PERKIN ELMER® 610TR Radiomatic Flow Scintillation Analyzer.

To prepare a 2 mM solution of IMP-470, 2.5 mg (1.67 µmol) IMP-470 (F.W. 1494.68) GG23-116-13 was dissolved in 836 µL 0.1 M NaOAc, pH 4.02

For F-18 labeling, to 3 µL 2 mM AlCl$_3$ solution was added 40 µL F-18 solution [1.736 mCi of F-18] followed by 20 µL (40 nmol) 2 mM IMP-470 solution and heated to 101° C. for 15 minutes. Reverse Phase HPLC analysis showed 26.10% (RT 8.90 min) and 47.29% (RT 9.30 min) of the activity was attached to the peptide and 26.61% of the activity eluted at the void volume of the column (2.70 min) (not shown).

TABLE 21

AlF-18 IMP 470

| Name | Retention (mins) | Height (CPM) | Area (CPM) | % ROI (%) |
|---|---|---|---|---|
| Region 1 | 2.70 | 30060.0 | 74431.3 | 26.61 |
| Region 2 | 8.90 | 40620.0 | 73021.9 | 26.10 |
| Region 3 | 9.30 | 73150.0 | 132278.4 | 47.29 |
| 3 Peaks | | | 279731.6 | 100.00 |

The crude labeled peptide was purified by transferring the reaction solution into a 1 cc WATERS® HLB column and eluting with water to remove unbound F-18 followed by 1:1 EtOH/H$_2$0 to elute the F-18 labeled peptide. The crude reaction solution was pulled through the HLB column into a 5 mL vial and the column was washed with 3×1 mL fractions of water (365 μCi). The HLB column was then placed on a new 3 mL vial and eluted with 2×200 μL 1:1 EtOH/H$_2$O to collect the labeled peptide (790 μCi). The reaction vessel retained 11.93 μCi, while the column retained 33.2 μCi of activity. The 790 μCi collected represents a recovery of 65.83% of labeled peptide.

An aliquot of the HLB purified F-18 labeled peptide was analyzed by RP-HPLC. Two products were detected –8.90 min 44.93%, 9.20 min 55.07% (F-18 was not detected in the void volume).

TABLE 22

HLB Purified AlF-18 IMP 470

| Name | Retention (mins) | Height (CPM) | Area (CPM) | % ROI (%) |
|---|---|---|---|---|
| Region 1 | 8.90 | 1670.0 | 3716.5 | 44.93 |
| Region 2 | 9.20 | 2070.0 | 4555.2 | 55.07 |
| 2 Peaks | | | 8271.7 | 100.00 |

Serum Stability of F-18 Labeled IMP-470 at 37° C.:

Sixty μL of the HLB column purified F-18 labeled peptide were mixed with 100 μL human serum and the sample was maintained at 37° C. during the entire RP-HPLC analysis.

TABLE 23

Serum Stability of AlF-18 IMP 470, t = 0

| Name | Retention (mins) | Height (CPM) | Area (CPM) | % ROI (%) |
|---|---|---|---|---|
| Region 1 | 8.90 | 6480.0 | 10402.5 | 36.33 |
| Region 2 | 9.30 | 8500.0 | 18234.3 | 63.67 |
| 2 Peaks | | | 28636.8 | 100.00 |

TABLE 24

Serum Stability of AlF-18 IMP 470, t = 4 hours at 37° C.

| Name | Retention (mins) | Height (CPM) | Area (CPM) | % ROI (%) |
|---|---|---|---|---|
| Region 1 | 8.90 | 5770.0 | 9756.9 | 22.97 |
| Region 2 | 9.30 | 17020.0 | 32719.0 | 77.03 |
| 2 Peaks | | | 42475.9 | 100.00 |

TABLE 25

Serum Stability of AlF-18 IMP 470, t = 1 hour at 37° C.

| Name | Retention (mins) | Height (CPM) | Area (CPM) | % ROI (%) |
|---|---|---|---|---|
| Region 1 | 8.90 | 3800.0 | 7857.0 | 21.07 |
| Region 2 | 9.20 | 12110.0 | 29429.3 | 78.93 |
| 2 Peaks | | | 37286.4 | 100.00 |

TABLE 26

Summary of Serum Stability of AlF-18 IMP 470

| Incubation Time/R.T. | 8.90 mins | 9.30 min |
|---|---|---|
| 0 | 36.33% | 63.67% |
| 1 h | 22.97% | 77.03% |
| 4 h | 21.07% | 78.93% |

In summary, an HSG containing peptide (IMP-470) linked to the bifunctional ligand L-NET A which has the macrocyclic NOTA and a neighboring bis(carboxmethyl)amine was successfully labeled with AlF-18. F-18 incorporation using 40 nmol of IMP-470 was 65.83% and the HLB column purified peptide was stable in human serum for 4 h at 37° C. Under similar labeling conditions the radiochemical yield with 40 nmol of IMP-467 was 75.34%.

Example 21

Synthesis of IMP 469

Figure 13:
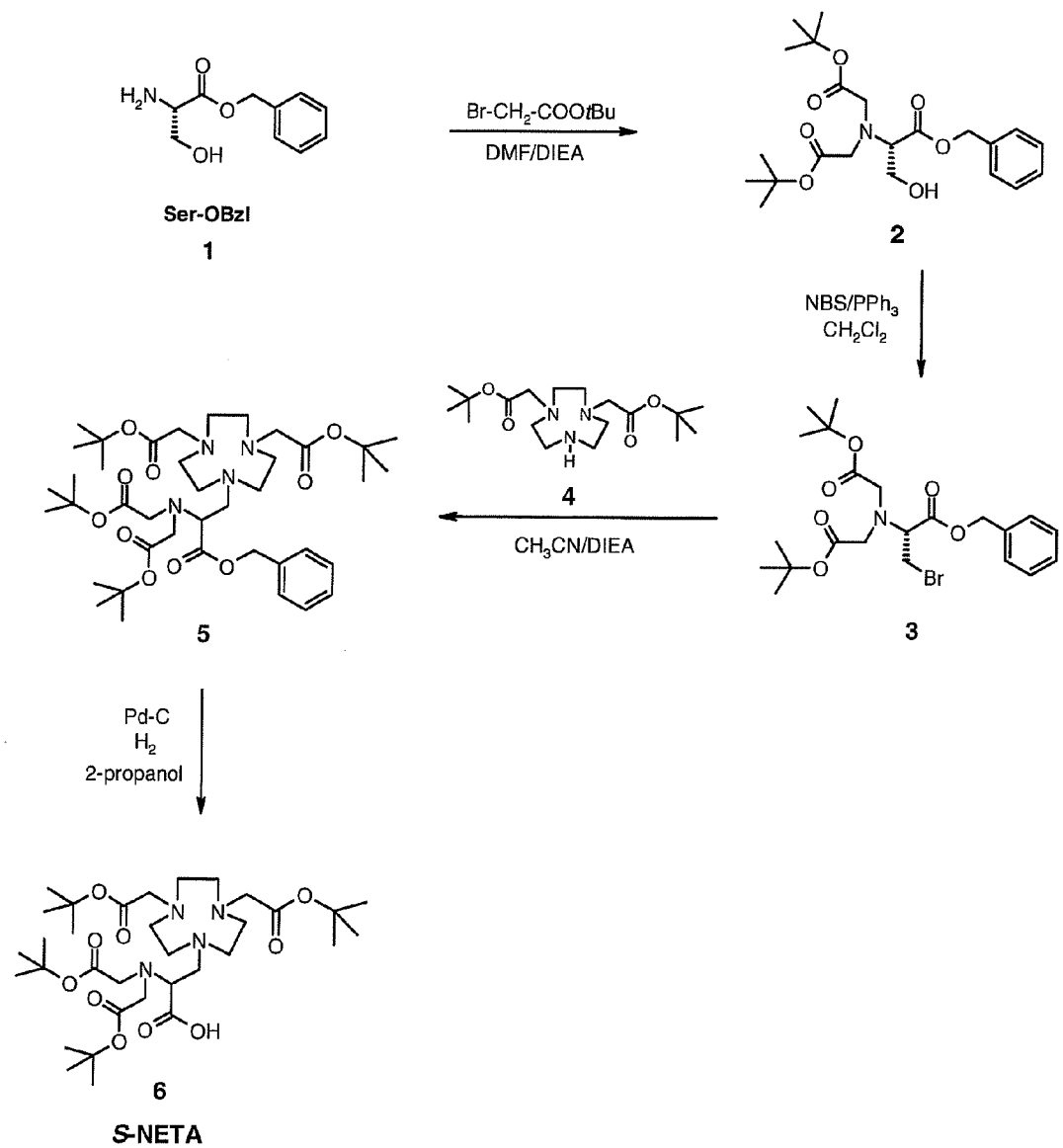
FIG. 13. Synthetic scheme for S-NETA.

An S-NETA conjugated targeting peptide, IMP 469, has been prepared, using the synthetic scheme shown in FIG. 13. The synthetic route starts with a double alkylation of 1 with t-butyl bromoacetate to yield alcohol 2. Reaction of 2 with PPh$_3$/NBS generates the bromide 3. Coupling of the bisubstituted TACN 4 in CH$_3$CN with 3 using DIEA provided the macrocycle 5. tert-butyl protected S-NETA 6 is obtained by benzyl deprotection using hydrogenation over Pd/C in near quantitative yield.

(t-BuO—CO—CH$_2$)$^2$-Ser-OBzl:

To a solution of 4.7945 g (20.70) H-Ser-OBzl.HCl in DMF (100 mL) at 0° C. were added diisopropylethylamine (50 mL) and tert-Butyl bromoacetate (9 mL, 90.90 mmol) dropwise over 2 h. The resultant mixture was stirred for 2 h at 0° C. and for 4 days at room temperature. The solvents were evaporated and the crude was dissolved in EtOAc. The EtOAc extract was washed with ABS pH 5.3, NaHCO$_3$ solution, brine, dried over anhydrous Na$_2$SO$_4$, filtered, and the filtrate concentrated under vacuum to provide 8.962 g of a yellow oil.

(t-BuO—CO—CH$_2$)$^2$-β-bromo-Ala-OBzl:

To a solution of 6.493 g (15.33 mmol) (t-BuO—CO—CH$_2$)-Ser-OBzl in anhydrous CH$_2$Cl$_2$ (100 mL) at 0° C. were added triphenylphosphine (4.0319 g, 15.37 mmol) and N-bromosuccinimide (2.7694 g, 15.56 mmol) in small portions over 1 h. The reaction mixture was stirred at for 30 min at 0° C. and 3 h at room temperature. The solvent was evaporated and the brown oil was purified using column chromatography (silica gel, 230-400 mesh) eluted with 10% EtOAc in hexanes to provide 4.778 g of a brown oil.

(t-BuO—CO—CH$_2$)$^2$-Ala(NOTA)-OBzl:

To a solution of 85.8 mg (0.240 mmol) of NO2AtBu in CH$_3$CN (3 mL) were added 100 μL diisopropylethylamine and 154 mg (0.317 mmol) (t-BuO—CO—CH$_2$)$^2$-β-bromo- Ala-OBzl and the resultant solution stirred at room temperature. After 31 h solvent was evaporated and the crude was purified by preparative RP-HPLC to yield 167.8 mg of the desired product.

t-BuO—CO—CH$_2$)$^2$-Ala(NOTA):

To a solution of 167.9 mg (0.220 mmol) of (t-BuO—CO—CH$_2$)-Ala(NOTA)-OBzl in 2-propanol (50 mL) was added 10% Pd/C catalyst (146.8 mg). The resultant solution was subjected to hydrogenolysis by agitation with H$_2$ (g) at 50 psi in a Parr hydrogenator apparatus at room temperature for 5 h. The reaction mixture was filtered through celite, and the filtrate concentrated to yield dark brown oil (115.4 mg).

Example 22

Synthesis and Labeling of IMP 465

Figure 14:
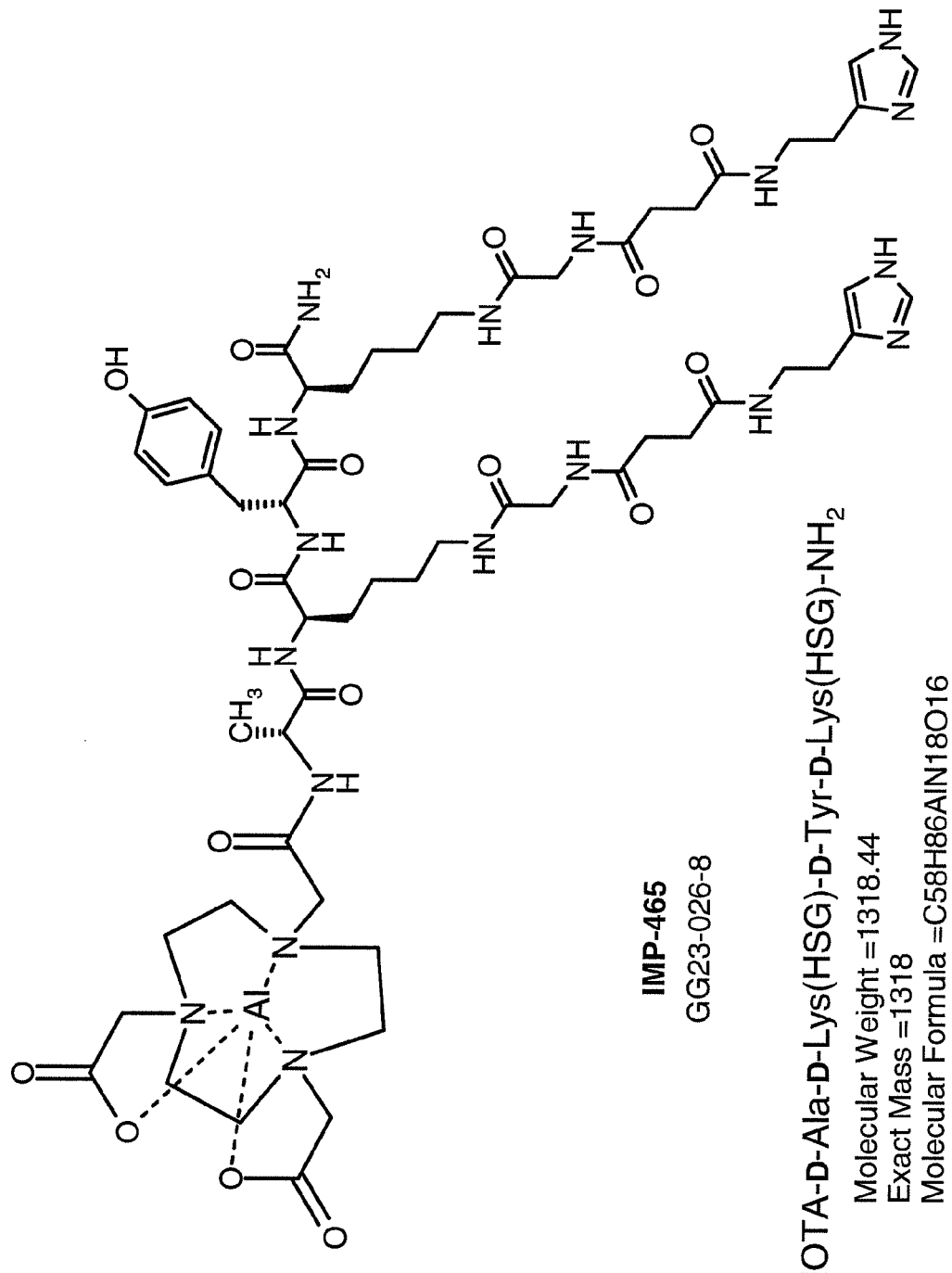
FIG. 14. Structure of IMP 465.

A HSG containing peptide (IMP-465, FIG. 14) linked to macrocyclic NOTA complexed with aluminum, was successfully labeled with F-18. F-18 incorporation using 40 nmol of IMP-465 was 13.20%. An intermediate peptide, IMP-461 NOTA-D-Ala-D-Lys(HSG)-D-Tyr-D-Lys(HSG)-NH$_2$, was made on Sieber Amide resin by adding the following amino acids to the resin in the order shown: Aloc-D-Lys(Fmoc)-OH, Trt-HSG-OH, the Aloc was cleaved Fmoc-D-Tyr(But)-OH, Aloc-D-Lys(Fmoc)-OH, Trt-HSG-OH, the Aloc was cleaved, 1,4-[Bis-(tert-butoxycarbonylmethyl)amino)-[1,4,7]triazanonan-1-yl]acetate. The peptide was then cleaved from the resin and purified by RP-HPLC to yield IMP-461.

Then 25.7 mg of IMP-461 was dissolved in 2 mL DI water to which was added 10.2 mg AlCl$_3$.3H$_2$O and the resultant solution heated to 100° C. for 1 h. The crude reaction mixture was purified by RP-HPLC to yield 19.6 mg of IMP-465. RP-HPLC analysis was performed as described above.

To prepare a 2 mM solution of IMP-465, 1.5 mg (1.14 µmol) IMP-465 (F.W. 1318.44) GG23-026-8 was dissolved in 569 µL 0.1 M NaOAc, pH 4.18

For F-18 labeling, to 3 µL 2 mM AlCl$_3$ solution was added 50 µL F-18 solution [0.702 mCi of F-18] followed by 20 µL (40 nmol) 2 mM IMP-465 solution and heated to 101° C. for 17 minutes. Reverse Phase HPLC analysis showed 15.38% (RT ~8.60 min) of the activity was attached to the peptide and 84.62% of the activity eluted at the void volume of the column (2.60 min).

TABLE 27

AlF-18 IMP 465

| Name | Retention (mins) | Height (CPM) | Area (CPM) | % ROI (%) |
| --- | --- | --- | --- | --- |
| Region 1 | 2.60 | 11380.0 | 25250.0 | 84.62 |
| Region 2 | 8.60 | 1880.0 | 4590.0 | 15.38 |
| 2 Peaks | | | 29840.0 | 100.00 |

The crude labeled peptide (377 µCi) was purified by transferring the reaction solution into a 1 cc Waters HLB column and eluting with water to remove unbound F-18 followed by 1:1 EtOH/H$_2$0 to elute the F-18 labeled peptide. The crude reaction solution was pulled through the HLB column into a 5 mL vial and the column was washed with 3×1 mL fractions of water (284 µCi). The HLB column was then placed on a new 3 mL vial and eluted with 2×200 µL 1:1 EtOH/H$_2$O to collect the labeled peptide (44.4 µCi, 13.2% of labeled peptide). The reaction vessel retained 4.54 µCi, while the column retained 3.39 µCi of activity after all of the elutions were performed. This Example demonstrates the feasibility of an alternative approach of stably complexing the metal with the chelating agent (IMP 461) and subsequently reacting the metal conjugated peptide with F-18.

Example 23

Synthesis of Folic Acid NOTA Conjugate

Folic acid is activated as described (Wang et. al. Bioconjugate Chem. 1996, 7, 56-62.) and conjugated to Boc-NH—CH$_2$—CH$_2$—NH$_2$. The conjugate is purified by chromatography. The Boc group is then removed by treatment with TFA. The amino folate derivative is then mixed with p-SCN-Bn-NOTA (Macrocyclics) in a carbonate buffer. The product is then purified by HPLC. The folate-NOTA derivative is labeled with Al—$^{18}$F as described in Example 10 and then HPLC purified. The $^{18}$F-labeled folate is injected i.v. into a subject and successfully used to image the distribution of folate receptors, for example in cancer or inflammatory diseases (see, e.g., Ke et al., Advanced Drug Delivery Reviews, 56:1143-60, 2004).

Example 24

Pretargeted PET Imaging in Humans

A patient (1.7 m$^2$ body surface area) with a suspected recurrent tumor is injected with 17 mg of bispecific monoclonal antibody (bsMab). The bsMab is allowed to localize to the target and clear from the blood. The F-18 labeled peptide (5-10 mCi on 5.7×10$^{-9}$ mol) is injected when 99% of the bsMab has cleared from the blood. PET imaging shows the presence of micrometastatic tumors.

Example 25

Imaging of Angiogenesis Receptors by F-18 Labeling

Labeled Arg-Gly-Asp (RGD) peptides have been used for imaging of angiogenesis, for example in ischemic tissues, where α$_v$β$_3$ integrin is involved. (Jeong et al., J. Nucl. Med. 2008, Apr. 15 epub). RGD is conjugated to SCN-Bz-NOTA according to Jeong et al. (2008). Al—$^{18}$F is attached to the NOTA-derivatized RGD peptide as described in Example 10 above, by mixing aluminum stock solution with F-18 and the derivatized RGD peptide and heating at 110° C. for 15 min, using an excess of peptide to drive the labeling reaction towards completion as disclosed in Example 13. The F-18 labeled RGD peptide is used for in vivo biodistribution and PET imaging as disclosed in Jeong et al. (2008). The Al—$^{18}$F conjugate of RGD-NOTA is taken up into ischemic tissues and provides PET imaging of angiogenesis.

Example 26

Imaging of Tumors Using F-18 Labeled Targetable Constructs

NOTA derivatives of peptides, polypeptides, proteins, carbohydrates, cytokines, hormones or cell receptor-binding agents are prepared according to U.S. Pat. No. 7,011,816 (incorporated herein by reference in its entirety). The NOTA-derivatized targetable constructs are labeled with Al—$^{18}$F as disclosed in Example 10. The conjugates are administered in vivo and successfully used for F-18 PET imaging of tumors.

Example 27

Imaging of Tumors Using Bispecific Antibodies

Bispecific antibodies having at least one arm that specifically binds a targeted tissue and at least one other arm that specifically binds a targetable construct are prepared according to U.S. Pat. No. 7,052,872, incorporated herein by reference in its entirety. The targetable construct comprises one or more NOTA chelating moieties. The targetable construct is labeled with Al—$^{18}$F as described in Example 13. A subject with a disease condition is injected with bispecific antibody. After allowing a sufficient time for free bispecific antibody to clear from the circulation, the subject is injected with F-18 labeled targetable construct. Imaging of the distribution of the F-18 label is performed by PET scanning.

In another exemplary embodiment, humanized or chimeric internalizing anti-CD74 antibody is prepared as described in U.S. Pat. No. 7,312,318. The p-SCN-bn-NOTA precursor is labeled with Al—$^{18}$F as described in Example 7. The Al—$^{18}$F NOTA is then conjugated to the antibody using standard techniques. Upon i.v. injection into a subject with a CD74-expressing tumor, the anti-CD74 antibody localizes to the tumor, allowing imaging of the tumor by PET scanning. In alternative embodiments, F-18 labeled antibodies are prepared using the alpha-fetoprotein binding antibody Immu31, hPAM4, cPAM4, RS7, anti-CD20, anti-CD19, anti-CEA and anti-CD22, as described in U.S. Pat. Nos. 7,300,655; 7,282, 567; 7,238,786; 7,238,785; 7,151,164; 7,109,304; 6,676,924; 6,306,393 and 6,183,744. The antibodies are conjugated to NOTA using standard techniques and labeled with Al—$^{18}$F as described for anti-CD74 antibody. The F-18 labeled antibodies are injected into subjects and provide successful imaging of tumors by PET scanning.

Example 28

Use of $^{18}$F-Labeled NOTA for Renal Flow Imaging

Aluminum stock solution (20 µL 0.05 M in pH 4 NaOAc buffer) is mixed with 200 µL of QMA purified F-18 (as in Example 10). The AlF-18 solution is then mixed with 500 µL pH 4, 0.2 M NOTA and heated for 15 min. The sample is then diluted in 5 mL PBS for injection. The F-18 labeled NOTA is used directly for successful renal flow imaging.

Example 29

Further Peptide Labeling Studies with Al—$^{18}$F

IMP 460 NODA-Ga-D-Ala-D-Lys(HSG)-D-Tyr-D-Lys (HSG)-NH$_2$ was synthesized in a similar manner as described above for IMP 361. The NODA-Ga ligand was purchased from CHEMATECH® and attached on the peptide synthesizer like the other amino acids. The crude peptide was purified to afford the desired peptide MH+ 1366.

Radiolabeling of IMP 460

IMP 460 (0.0020 g) was dissolved in 732 µL, pH 4, 0.1 M NaOAc. The F-18 was purified as described in Example 10, neutralized with glacial acetic acid and mixed with the Al solution. The peptide solution, 20 µL was then added and the solution was heated at 99° C. for 25 min. The crude product was then purified on a WATERS® HLB column as described above. The Al—F-18 labeled peptide was in the 1:1 EtOH/H$_2$O column eluent. The reverse phase HPLC trace in 0.1% TFA buffers showed a clean single HPLC peak at the expected location for the labeled peptide.

Example 30

Carbohydrate Labeling

A NOTA thiosemicarbazide derivative is prepared by reacting the p-SCN-bn-NOTA with hydrazine and then purifying the ligand by HPLC. Al—F-18 is prepared as described in Example 10 and the Al—F-18 is added to the NOTA thiosemicarbazide and heated for 15 min. Optionally the Al—F-18-thiosemicarbazide complex is purified by HPLC. The Al—F-18-thiosemicarbazide is conjugated to oxidized carbohydrates by known methods. The F-18 labeled carbohydrate is successfully used for imaging studies using PET scanning.

Example 31

Lipid Labeling

A lipid comprising an aldehyde is conjugated to the Al—F-18 NOTA thiosemicarbazide of Example 30 and the F-18 labeled lipid is used for successful imaging studies using PET scanning.

In an alternative embodiment, a lipid comprising an amino group is reacted with p-SCN-bn-NOTA. The NOTA-labeled lipid is reacted with Al—F-18 as described in the Examples above. The F-18 labeled lipid is used for successful imaging studies using PET scanning.

Example 32

Aptamer Labeling

An aptamer comprising an aldehyde is conjugated to the Al—F-18 NOTA thiosemicarbazide of Example 30. The F-18 labeled aptamer is administered to a subject and used for successful imaging studies using PET scanning.

---

What is claimed is:

1. A method of F-18 imaging by positron emission tomography (PET) comprising:
   a) reacting F-18 with a metal selected from the group consisting of aluminum, gallium, indium, lutetium or thallium to form an F-18 metal complex;
   b) attaching the F-18 metal complex to a molecule to form one or more F-18 labeled molecules;
   c) administering the F-18 labeled molecules to a subject; and
   d) imaging the distribution of the F-18 labeled molecule by PET scanning.

2. The method of claim 1, wherein the F-18 labeled molecule is administered to the subject without separating the F-18 labeled molecules from unlabeled molecules.

3. The method of claim 1, further comprising:
   e) separating the F-18 labeled molecules from unlabeled molecules to produce purified F-18 labeled molecules before the F-18 labeled molecules are administered to the subject.

4. The method of claim 1, wherein the imaged distribution of F-18 labeled molecules is indicative of the presence or absence of a disease selected from the group consisting of solid cancers, hematopoietic cancers, autoimmune disease, neurodegenerative disease and cardiovascular disease.

5. The method of claim 4, wherein the disease is selected from the group consisting of sarcomas, melanomas, gliomas, breast cancer, lung cancer, pancreatic cancer, ovarian cancer, colorectal cancer, prostate cancer, leukemias, lymphomas, myelomas Alzheimer's disease, myocardial infarction, congestive heart failure, cardiac necrosis, thrombosis, stroke, atherosclerosis, rheumatoid arthritis, lupus erythematosus; and AIDS.

6. The method of claim 1, wherein the F-18 labeled molecule is used to image receptors.

7. The method of claim 6 wherein the receptors are angiogenesis receptors and the F-18 labeled molecule is Al-18F conjugated RGD-NOTA.

8. The method of claim 1, wherein the F-18 labeled molecule is used to image tumors.

9. The method of claim 8, wherein the F-18 labeled molecule is F-18 labeled bombesin.

10. The method of claim 8, wherein the F-18 labeled molecule is an antibody or fragment thereof, selected from the group consisting of hLL1, hLL2, hImmu31, hPAM4, hRS7, hA1g, hA20, hMN-14, hMu-9, hMN-3, hMN-15 and hL243.

11. The method of claim 1, wherein the F-18 labeled molecule is F-18 labeled NOTA, C-NETA or lysine-NETA and the F-18 labeled molecule is used to image renal flow.

12. The method of claim 1, wherein the F-18 labeled molecule comprises antibody or an antibody fragment.

13. The method of claim 1, where the F-18 labeled molecule is a targetable construct that binds to a bispecific antibody.

14. The method of claim 13, further comprising:
   i) administering a bispecific antibody to a subject, said bispecific antibody having at least one binding site for the targetable construct and at least one binding site for an antigen, wherein the presence of the antigen is indicative of a disease or condition; and ii) allowing a sufficient amount of time for bispecific antibody that is not bound to the antigen to clear from circulation prior to the administration of the targetable construct.

15. The method of claim 14, wherein the antigen is a tumor-associated antigen.

16. The method of claim 14, wherein the antigen is present on a pathogenic organism.

17. The method of claim 16, wherein the pathogen is a virus, bacterium, fungus, yeast or microorganism.

18. The method of claim 17, wherein the virus is selected from the group consisting of human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus; or the bacterium is selected from the group consisting of *Streptococcus agalactiae, Legionella pneumophila, Streptococcus pyogenes, Escherichia coli, Neisseria gonorrhoeae, Neisseria meningitidis, Pneumococcus, Hemophiluis influenzae B, Treponema pallidum, Lyme disease spirochetes, Pseudomonas aeruginosa, Mycobacterium leprae, Brucella abortus, Mycobacterium tuberculosis* and *Clostridium tetani*.

19. The method of claim 15, wherein the antigen is selected from the group consisting of colon-specific antigen-p (CSAp), carcinoembryonic antigen (CEA), CD4, CDS, CD8, CD14, CD15, CD19, CD$_2$O, CD21, CD22, CD23, CD25, CD30, CD45, CD66a-d, CD67, CD74, CD79a, CD80, CD138, HLA-DR, Ia, Ii, MUC1, MUC2, MUC3, MUC4, NCA, EGFR, HER 2/neu receptor, TAG-72, EGP-1, EGP-2, A3, KS-1, Le(y), S100, PSMA, PSA, tenascin, folate receptor, VEGFR, EGFR, PDGFR, FGFR, P1GF, ILGF-1, necrosis antigens, IL-2, IL-6, T101, MAGE, or a combination of these antigens.

20. The method of claim 19, wherein the bispecific antibody comprises an antibody or fragment thereof selected from the group consisting of hLL1, hLL2, hImmu31, hPAM4, hRS7, hA19, hA20, hMN-14, hMu-9, hMN-3, hMN-15 and hL243.

21. The method of claim 1, wherein the molecule is folic acid.

22. The method of claim 1, wherein the molecule is TA138.

* * * * *

SEQUENCE LISTING

<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Lys Tyr Lys
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Tyr Lys Lys
1

<210> SEQ ID NO 3
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ile Glu Tyr Leu Ala Lys Gln Ile Val Asp Asn Ala Ile Gln Gln
1               5                   10                  15

Ala

<210> SEQ ID NO 6
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 7
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Ser Gly Gly Gly Ser Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Gly Gly Gly Gly Ser Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser Gly Gly Gly Cys Gly
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Trp Val Trp Ala Val Gly His Leu Met
1               5                   10
```

```
<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Lys Ser Cys
1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser Gly Gly Gly Gly Ser
1               5                   10
```